(12) United States Patent
Paul et al.

(10) Patent No.: US 10,941,409 B2
(45) Date of Patent: Mar. 9, 2021

(54) METHOD FOR GENE OPTIMIZATION

(71) Applicant: GENECTIVE, S.A., Saint-Beauzire (FR)

(72) Inventors: Wyatt Paul, Chappes (FR); Nora Temme, Selm (DE)

(73) Assignee: Genective, S.A., Saint-Beauzire (FR)

( * ) Notice: Subject to any disclaimer, the term of this patent is extended or adjusted under 35 U.S.C. 154(b) by 0 days.

(21) Appl. No.: 15/451,231

(22) Filed: Mar. 6, 2017

(65) Prior Publication Data

US 2017/0226524 A1     Aug. 10, 2017

Related U.S. Application Data

(63) Continuation of application No. PCT/EP2016/066045, filed on Jul. 6, 2016.

(30) Foreign Application Priority Data

Jul. 6, 2015 (EP) .................................... 15306105

(51) Int. Cl.
     *C12N 15/82*      (2006.01)
     *C07K 14/325*      (2006.01)

(52) U.S. Cl.
     CPC ........ *C12N 15/8216* (2013.01); *C07K 14/325* (2013.01); *C12N 15/8257* (2013.01); *C12N 15/8286* (2013.01); *Y02A 40/146* (2018.01)

(58) Field of Classification Search
CPC ............ C12N 15/8216; C12N 15/8257; C12N 15/8286; C07K 14/325; Y02A 40/146
See application file for complete search history.

(56) References Cited

U.S. PATENT DOCUMENTS

| 7,741,118 B1 | 6/2010 | Fischhoff et al. |
| 8,314,292 B2 | 11/2012 | Carozzi et al. |
| 2010/0005543 A1 | 1/2010 | Sampson et al. |
| 2013/0024998 A1 | 1/2013 | Paul et al. |

FOREIGN PATENT DOCUMENTS

| WO | WO 91/16432 A1 | 10/1991 |
| WO | WO 2012/131619 | 10/2012 |
| WO | WO 2012/142371 | 10/2012 |
| WO | WO 2015/109241 | 7/2015 |

OTHER PUBLICATIONS

Campbell et al, 1990, Codon usage in higher plants, green algae and cyanobacteries. Plant Physiol. 92:1-11.
Christensen et al., 1996, Ubiquitin promoter-based vectors for high-level expression of selectable and/or screenable marker genes in monocotyledonous plants, Transgenic. Res., 5 :213.
Clark et al., 1989, Mutations at the transit peptide-mature protein junction separate two cleavage events during chloroplast import of the chlorophyll a/b-binding protein. J. Biol. Chem. 264:17544-17550.
Colgan DF et al., 1997, Mechanism and regulation of mRNA polyadenylation. Genes Dev. 11(21):2755-66.
Della-Cioppa et al., 1987, Protein Trafficking in Pant Cells, Plant Physiol. 84:965-968.
Depicker et al., Nopaline Synthase: Transcript Mapping and DNA Sequence, J Mol Appl Genet 1982;1(6):561-73.
Depigny-This et al., 1992, The cruciferin gene family in radish, Plant Molecular Biology, 20 :467-479.
Graber JH et al., 1999, In silica detection of control signals: mRNA 3'-end-processing sequences in diverse species. Proc Natl Acad Sci U S A. 96:14055-60.
Ishida Y, et al., 1996, High efficiency transformation of maize (*Zea mays* L.) mediated by Agrobacterium tumefaciens. Nature Biotechnol. 14, 745-50.
Jefferson RA et al., 1987. GUS fusions: beta-glucuronidase as a sensitive and versatile gene fusion marker in higher plants. EMBO J. 6: 3901-3907.
Ji G et al., 2015, PASPA: a web server for mRNA poly(A) site predictions in plants and algae. Bioinformatics 31:1671-3.
Joshi CP, 1987, Putative polyadenylation signals in nuclear genes of higher plants: a compilation and analysis. Nucleic Acids Res. 15(23):9627-40.
Kay et al., 1987, Duplication of CaMV 35S Promoter Sequences Creates a Strong Enhancer for Plant Genes, Science, 236 :1299-1302.
Komari T et al.,1996. Vectors carrying two separate T-DNAs for co-transformation of higher plants mediated by Agrobacterium tumefaciens and segregation of transformants free from selection markers. Plant J. 10:165-74.
Leckie BM et al., 2011. Agroinfiltration as a technique for rapid assays for evaluating candidate insect resistance transgenes in plants. Plant Cell Rep. 30(3):325-34.
Lu A et al., 2015. Maize Protein Expression. In Recent Advancements in Gene Expression and Enabling Technologies in Crop Plants. Editors; Kasi Azhakanandam, Aron Silverstone, Henry Daniell and Michael R. Davey. Springer ISBN 978-1-4939-2201-7; ISBN 978-1-4939-2202-4 (eBook); DOI 10.1007/978-1-4939-2202-4.
McElroy et al., 1990, Isolation of an Efficient Actin Promoter for Use in Rice Transformation, Plant Cell, 2 :163-171.
Mogen BD et al., 1990, Upstream sequences other than AAUAAA are required for efficient messenger RNA 3'-end formation in plants. Plant Cell. 2(12):1261-72.

(Continued)

*Primary Examiner* — James D Schultz
(74) *Attorney, Agent, or Firm* — Paul M. Richter, Jr.; Devlin Law Firm LLC

(57) ABSTRACT

The invention relates to method of modifying a coding sequence encoding a non-plant protein, comprising the steps of optimizing said coding sequence by codon substitution, thereby obtaining an optimized coding sequence which encodes said non-plant protein; and re-introducing at least one wild-type polyadenylation motif sequence at its position within said optimized gene sequence.

10 Claims, 14 Drawing Sheets
Specification includes a Sequence Listing.

(56) References Cited

OTHER PUBLICATIONS

Murray EE et al., 1989, Codon usage in plant genes. Nucleic Acids Res. 17:477-498.
Sanfaçon H et al., 1991, A dissection of the cauliflower mosaic virus polyadenylation signal. Genes Dev. 5(1):141-9.
Shah et al., 1986, Engineering Herbicide Tolerance in Transgenic Plants, Science 233:478-481.
Sheen, J. 2002, A transient expression assay using *Arabidopsis* mesophyll protoplasts. http://genetics.mgh.harvard.edu/sheenweb/.
Skinner et al, JBrowse: A next-generation genome browser, Genome Res. 2009. 19: 1630-1638.
Tzanis G et al, 2011. PolyA-iEP: A data mining method for the effective prediction of polyadenylation sites. Expert Syst. Appl. 38(10) 12398-12408.
Verdaguer B et al., 1996. Isolation and expression in transgenic tobacco and rice plants, of the cassava vein mosaic virus (CVMV) promoter. Plant Mol Biol. 31:1129-39.
Verdaguer et al., 1998, Functional organization of the cassava vein mosaic virus (CsVMV) promoter, Plant Mol Biol.37(6):1055-67.
Wu X et al (2012). Comprehensive recognition of messenger RNA polyadenylation pattern in plants. African journal of biotechnology, vol. 11(14), pp. 3215-3234.
International Search Report and Written Opinion in International Application No. PCT/EP2016/066045, dated Oct. 18, 2016.
Haffani, Y.Z. et al. Premature polyadenylation contributes to the poor expression of the Bacillus theringiensis cry3Cal gene in trangenic potato plants, Molecular and General Genetics, vol. 264, No. 1-2, Sep. 1, 2000, pp. 82-88.
Von Heijne et al., 1991, CHLPEP—A Database of Chloroplast Transit Peptides, Plant Mol. Biol. Rep. 9:104-126.
Romer et al., 1993, Expression of teh Genes Encasing the Early Carotenoid Biosynthetic Enzymes in Capsicum Annuum, Biochem. Biophys. Res. Commun. 196:1414-1421.
Guilley H et al., Transcription of Cauliflower mosaic virus DNA: detection of promoter sequences, and characterization of transcripts. Cell. 1982, 30: 763-773.
OligoCounter, 2017 (http://webhost1.mh-hannover.de/davenpart/oligacounter/, Tümmler laboratory at Hannover Medical School, Germany).
Davenport et al. 2009, Visualization of Pseudomonas genomic structure by abundant 8-14mer oligonucleotides, OligoCounter Manual, Environmental Microbiology, 2009 11:1092-1104, PMID: 19161433.

SEQUENCE LISTING

```
<160> NUMBER OF SEQ ID NOS: 33

<210> SEQ ID NO 1
<211> LENGTH: 1891
<212> TYPE: DNA
<213> ORGANISM: Artificial Sequence
<220> FEATURE:
<223> OTHER INFORMATION: Axmi028 - wild-type sequence lacking the
      C-terminal Crystal Domain (028-WT)

<400> SEQUENCE: 1
```

```
atgaatcaaa aaaactatga aattataggt gcttcaacaa acggcacaat tgaattacct      60
gaagattaca acactatagt cagcccctat gatgctccag catccgttac tacaactatt     120
gaaattactg aaccatact aagcgattta ggtgttccag gagcatcatc agttagttta     180
cttttgaata aacttataaa tctattatgg ccaaatgata ccaatactgt gtggggaca     240 ttcggaaaag aaaccgctga tcttctaaat gaagtgttat ctccagatga tccagtagta     300
aaagatgcaa ataccatttt aaaaggaata acggatccc ttaacttata tttaaatgca     360
cttgaaatat ggaaaaaaga ccccaacaac ttaactacca tagagaatgt cacagattac     420
tttcgtagtt tgaatgtggt ttttacacat gatatgcctt catttgctgt acctggatat     480
gaaacgaagt tattaacaat ttatgcacaa gctgcaaatc ttcatttact tttattaaga     540
gatgcttcta ggtttggaga aggttgggga ctgactcaag aaatcataaa tactaactat     600
aatgatcaat tacgattgac agcagaatac acggaccatt gtgtaaagtg gtacaacgca     660
ggattagaaa aattaaaagg gaatttaact ggggaaaatt ggtatactta taatagattt     720
cgtagagaaa tgacgttaat ggtgttagac gtagttgcat tatttccaaa ctacgataca     780
cgaatgtacc cgatcggaac gtcatcagaa cttacaagaa tgatctatac agatccaatt     840
gcttatacac aaagcgatcc atggtacaag ataacatctc tttctttttc aaatattgaa     900
aacagtgcga ttccaagtcc ttctttcttc aggtggctaa aatccgtttc aattaatagc     960
cagtggtggg gcagtggtcc tagtcaaacc tactattggg ttggacatga attggtatat    1020
tctaattcaa attctaatca atcacttaaa gttaaatatg gagaccctaa ttcttttatt    1080
gagccccctg attctttcag ttttttcttct acggatgttt acagaacaat atctgttgtt    1140
agaaattcag taagtaatta tatagtaagt gaagttcgat tcaattcaat tagtagtaca    1200
aatcaaatta gtgaagaaat ttataaacat caatcaaatt ggagtagaca agaaaccaaa    1260
gattcaatta cagaactatc cttagctgct aatcccccaa caacatttgg aaatgtagca    1320
gaatacagtc atagattagc atatatttca gaggcatacc aaagtcacaa cccatcaaaa    1380
tacccaacct acattcctgt attcggttgg acgcatacaa gcgtacgtta cgataataaa    1440
atcttcccgg acaaaatcac tcaaattcca gctgttaaaa gctcctcagc caaggtgga    1500 tcatggaaaa atatagtgaa aggccccggg tttactggag agatgtgac aactgcagtt    1560 tcgccagcaa ctgtaaccga cataataaaa atacaagtta ctctagatcc aaattcactt    1620
tcacaaaaat atcgtgcacg acttcgctat gcttccaatg catttgtacc agctacattg    1680
tatacaaata caagtagtaa ttataatttt gaacttaaaa aagtacaac tgaacagttt    1740 acaacatata attcatacca gtatgtagat atcccaggtt caatacaatt taataatact    1800
tctgatacag tctctgttta tttgcatatg gattcaacat ctaatgtaaa cgttcatgta    1860
gatagaattg aattcattcc aatagatgta a                                   1891
```

<210> SEQ ID NO 2
<211> LENGTH: 1890
<212> TYPE: DNA
<213> ORGANISM: Artificial
<220> FEATURE:
<223> OTHER INFORMATION: Axmi028 optimised sequence (028-opt)

<400> SEQUENCE: 2

```
atgaaccaga agaactacga gatcatcggc gcgtccacca acgggacgat cgagctgccc      60
gaggattaca acacgatcgt cagcccgtac gacgcgcctg catcagtgac aaccaccatc     120
```

| | |
|---|---|
| gagatcacgg ggacaatcct gtctgacctc ggtgtgcctg gagcaagttc agtcagcctt | 180 |
| ctgctcaaca agctgatcaa cctgctctgg ccgaacgaca ccaacaccgt gtggggtacg | 240 |
| ttcggcaagg agacggccga tctcctcaac gaggtcctgt cacctgatga cccagttgtc | 300 |
| aaggacgcta atacgatcct caaggggatc aacgggtcgc tgaacctcta cctgaacgcc | 360 |
| ctcgagatct ggaagaagga cccgaacaac ctgactacta tcgagaacgt gactgactac | 420 |
| ttccggtcac tcaacgtcgt gttcacgcac gacatgccct cgttcgccgt ccctggatac | 480 |
| gagaccaagc tgctcaccat ctacgcccag gctgcaaacc tccatctgct gttgctcagg | 540 |
| gacgcatcac gtttcggtga gggatggggt ttgacccagg agatcatcaa cacgaactac | 600 |
| aacgaccagc tccgcctcac cgccgaatac accgaccact gcgtgaagtg gtacaacgcc | 660 |
| ggcttggaga agctgaaggg caacctcacg ggtgagaact ggtacacgta caaccggttc | 720 |
| cgcagggaga tgaccctcat ggtgctggac gtggtcgcat tgttcccaaa ctacgacacc | 780 |
| cgcatgtacc cgatcgggac atcaagcgag cttacccgta tgatctacac tgaccccatc | 840 |
| gcctacaccc agtccgaccc atggtacaag atcacgtccc tgagcttctc gaacatcgag | 900 |
| aacagcgcga tcccctcccc atcgttcttc cgctggctca gtccgtcag cattaactcc | 960 |
| cagtggtggg gttccggacc ttcacaaacc tactactggg tggggcacga actggtctac | 1020 |
| agcaacagca acagcaacca gtcgctgaag gtgaagtacg gcgaccctaa cagcttcatc | 1080 |
| gagccccgg attccttctc cttcagcagc acggacgtgt acaggaccat ctcagtcgtg | 1140 |
| cgtaattccg tgtcgaacta catcgtgtcg gaggtgcggt tcaacagcat ctcctccacc | 1200 |
| aaccagatca gcgaggaaat ctacaagcac cagtctaact ggagccggca ggagacaaag | 1260 |
| gactcaatca ccgagctgag cctggccgcc aacccgccaa ccacgttcgg aaacgttgcc | 1320 |
| gagtacagtc accgcctggc ttacatctca gaggcgtacc agtctcacaa cccatctaag | 1380 |
| taccccgacct atatccccgt gttcgggtgg acccacacat ccgtgaggta cgacaacaag | 1440 |
| attttcccgg acaagatcac gcagatcccc gcggttaaga gtagctcagc tcagggggga | 1500 |
| agctggaaga atatcgtcaa ggggcccgga ttcacgggtg gagacgtgac gacggcggtt | 1560 |
| tcacctgcaa ctgttacgga tattatcaag atccaggtta cccttgatcc caacagtctg | 1620 |
| agccagaagt atcgggcacg ccttcgctac gccagcaacg ccttcgtccc ggcaacccctt | 1680 |
| tatacgaaca cctcgtcaaa ctacaacttc gaactgaaga agggcacgac tgagcagttc | 1740 |
| acgacctaca acagctacca gtacgtggac atccccggca gcatccagtt caacaatacg | 1800 |
| tccgacaccg tgtcggtcta cctgcacatg gactcaacct cgaacgtgaa cgtgcacgtg | 1860 |
| gaccggatcg agttcatccc gatcgactga | 1890 |

<210> SEQ ID NO 3
<211> LENGTH: 1890
<212> TYPE: DNA
<213> ORGANISM: Artificial
<220> FEATURE:
<223> OTHER INFORMATION: Axmi028 optimised sequence containing all
      AATAAA-like motifs present in the WT sequence (028-opt+pA)

<400> SEQUENCE: 3

| | |
|---|---|
| atgaatcaaa agaactatga atcatcggc gcgtccacca acgggacgat cgagctgccc | 60 |
| gaggattaca cacgatcgt cagcccgtac gacgcgcctg catcagtgac aaccaccatc | 120 |
| gagatcacgg ggacaatact atctgacctc ggtgtgcctg gagcaagttc agtcagcctt | 180 |
| ctgctcaata aactgatcaa cctgctctgg ccgaacgaca ccaacaccgt gtggggtacg | 240 |

```
ttcggcaagg agacggccga tctcctcaac gaggtcctgt cacctgatga cccagttgtc    300
aaggacgcta atacgatcct caagggaata acgggtcgc tgaacctcta cctgaacgcc     360
ctcgagatct ggaagaagga cccgaacaac ctgactacta tcgagaacgt gactgactac    420
ttccggtcac tcaacgtcgt gttcacgcac gacatgccct cgttcgccgt ccctggatat    480
gaaaccaagc tgctcaccat ctacgcccag gctgcaaacc tccatctgct gttgctcagg    540
gacgcatcac gtttcggtga gggatggggt tgacccagg agatcataaa tactaactac     600
aacgaccagc tccgcctcac cgccgaatac accgaccact gcgtgaagtg gtacaacgcc    660
ggcttggaga aattaaaggg caacctcacg ggtgagaact ggtacacgta caaccggttc    720
cgcagggaga tgaccctcat ggtgctggac gtggtcgcat tgttcccaaa ctacgacacc    780
cgcatgtacc cgatcgggac atcaagcgag cttacccgta tgatctacac tgaccccatc    840
gcctacaccc agtccgaccc catggtacaag atcacgtccc tgagcttctc gaacatcgag    900
aacagcgcga tccctccc atcgttcttc cgctggctca gtccgtctc aattaattcc       960 cagtggtggg gttccggacc ttcacaaacc tactactggg tggggcacga actggtctac    1020
agcaacagca acagcaatca tcgctgaag gtgaagtacg cgaccctaa cagcttcatc      1080 gagccccgg attccttctc cttcagcagc acggacgtgt acaggaccat ctcagtcgtg     1140
cgtaattccg tgtcgaacta catcgtgtcg gaggtgcggt tcaacagcat ctcctccacc    1200
aatcaaatca gcgaggaaat ctacaagcac caatcaaact ggagccggca ggaaaccaag    1260
gactcaatca ccgagctgag cctggccgcc aacccgccaa ccacgttcgg aaacgttgcc    1320
gaatacagtc accgcctggc ttacatctca gaggcgtacc agtctcacaa cccatcaaaa    1380 taccccgacct atatccccgt gttcgggtgg acccacacat ccgtgaggta cgacaataaa    1440
attttcccgg acaagatcac gcagatcccc gcggttaaga gtagctcagc tcaggggga    1500 agctggaaaa atatcgtcaa ggggcccgga ttcacgggtg gagacgtgac gacggcggtt    1560
tcacctgcaa ctgttacgga tataataaaa atacaggtta cccttgatcc caacagtctg    1620 agccaaaat atcgggcacg cctcgctac gccagcaacg ccttcgtccc ggcaacccctt     1680 tatacgaata catcgtcaaa ctacaacttc gaactgaaga agggcacgac tgagcagttc    1740
acgacatata acagctacca gtacgtggac atccccggct caatacagtt caataatacg    1800
tccgacaccg tgtcggtcta cctgcacatg gactcaacct cgaacgtgaa cgtgcacgtg    1860
gaccggatcg agttcatccc gatcgactga                                     1890
```

<210> SEQ ID NO 4
<211> LENGTH: 2040
<212> TYPE: DNA
<213> ORGANISM: Artificial
<220> FEATURE:
<223> OTHER INFORMATION: wild-type sequence lacking the C-terminal
      Crystal Domain (100-WT)

<400> SEQUENCE: 4

```
atgaatcgaa ataatcaaaa tgaatgtgaa attattgatg cccctcattg tggatgtccg     60
tcagatgatg ttgtgaaata tccttttggca agtgacccaa atgcagcgtt acaaaatatg   120
aactataaag attatttaca aacgtatgat ggagactata cagattctct tattaatcct   180
aacttatcta ttaatactag ggatgtacta caaacaggta ttactattgt gggaagaata   240
ctagggtttt taggtgttcc atttgcgggg caactagtta cttctctatac ctttctctta   300 aatcagttat ggccaactaa tgataatgca gtatgggaag cttttatgga acaaatagaa   360
```

```
gggattatcg ctcaaagaat atcggagcaa gtagtaagga atgcgcttga tgccttaact    420
ggaatacacg attattatga ggaatattta gcggcattag aggagtggct ggaaagaccg    480
agcggcgcaa gggctaactt agcttttcag aggtttgaaa atctacatca attatttgta    540
agtcagatgc caagttttgg tagtggtcct ggtagtgaaa gagatgcggt agcattgctg    600
acagtatatg cacaagcagc gaatctccat ttgttgttat aaaagatgc agaaatttat     660
ggggcgagat ggggacttca acaaggccaa attaatttat attttaatgc tcaacaagat    720
cgcactcgaa tttataccaa tcattgtgtg gcaacatata atagaggatt aggagactta    780
agaggcacaa atactgaaag ttggttaaat taccatcaat tccgtagaga gatgacatta    840
atggcaatgg atttagtggc attattccca tactataatt tacgacaata tccaaacggg    900
gcaaaccctc agcttacacg tgatgtatat acagatccga ttgtatttaa tccatcagct    960
aatgtaggat tatgtagacg ttggggcaat aacccatata atacatttc ggaacttgaa    1020
aatgccttca ttcgcccgcc acattttttt gataggttga atagtttaac aattagtaga   1080
aatagatttg acgttggatc aaactttata gagccttggt ctggacatac gttacgccgt   1140
agttttctga acacttcggc agtacaagaa gatagttatg ccaaattac taatcaaaga    1200
acaacaatta atctaccagc taatggaact gggcgagtgg agtcaacagc agtagatttt   1260
cgtagcgcgc ttgtggggat atacggcgtt aatagagctt cttttattcc cggtggtgtg   1320
tttaatggca cgactcaacc ttctactgga ggatgtagag atttgtatga ttcaagtgat   1380
gaattaccac cagaagaaag tagtggaacg tttgaacata ggttatctca tgttaccttt   1440
ttaagtttta caactaatca ggctggatcc atagccaatg cagggcgcgt ccctacttat   1500
gtctggaccc atcgagatgt ggaccttaat aacacgatta ctgcagatag aattacacac   1560
ttaccattga taaaatcaaa tgtgcaacgc agtggtcgcg cagtaaaagg accaggattt   1620
acaggaggag atgtactccg aatgtcatca agtgatgctg atatatcaat aataggaata   1680
acggcaggtg caccgctaac acaacaatat cgtataagat tgcgttatgc ttcaaatgta   1740
gatgttacta tccgtttagt gagacaggac acccaaagta atataggaag cataaactta   1800
ttacgtacaa tgaacagtgg agaggagtca aggtatgaat catatcgtac tgtagagatg   1860
cctggtaatt ttagaatgac tagtagttca gcacagattc gactatttac tcaaggactt   1920
cgagtgaatg gagaattgtt tcttgatagt cttgaattta tcccagttaa tccgacacgt   1980
gaggcggaag aggatttaga agcagcgaag aaagcggtga cgagcttgtt tacacgttaa   2040
```

<210> SEQ ID NO 5
<211> LENGTH: 2040
<212> TYPE: DNA
<213> ORGANISM: Artificial
<220> FEATURE:
<223> OTHER INFORMATION: Axmi100 optimised sequence (100-opt)

<400> SEQUENCE: 5

```
atgaacagga acaaccaaaa tgaatgtgag atcattgatg ctcctcattg tggctgccct     60
tctgatgatg tggtgaaata tcctcttgct tcagatccaa atgctgctct ccagaacatg    120
aactacaagg actacctcca acatatgat ggagactaca ccgacagctt gatcaacccc     180
aacctctcca tcaacacaag agatgtgctg caaactggca tcaccattgt tggaaggatc    240
ttgggcttcc tcggcgtccc cttcgccggc cagctggtga ccttctacac cttcctcctc    300
aaccagctat ggccaacaaa tgacaatgct gtttgggagg ccttcatgga gcagattgaa    360
ggcatcattg ctcaaaggat ctccgagcaa gtggtgagaa atgctctgga tgctctcacc    420
```

```
ggcatccatg actactacga ggagtacctc gccgcgctgg aagaatggct ggagaggcca      480
tcaggagcaa gggccaacct cgccttccaa agatttgaga acctccacca gctgttcgtg      540
agccagatgc cctccttcgg cagcggccct ggatcagaaa gagatgctgt ggcgctgctc      600
accgtctatg ctcaagctgc caacctccat ctgctgctgc tgaaggatgc tgagatttat      660
ggagctagat ggggcctcca gcaaggccag atcaacctct acttcaatgc tcagcaggac      720
aggacaagga tctacaccaa ccactgcgtc gccacctaca cagaggcct ggagatctc      780 cgcggcacca acactgaatc atggctgaac taccaccagt tcagaaggga gatgaccttg      840
atggccatga tctggtggc gctgttcccc tactacaacc tccgccaata tccaaatgga      900
gctaatcctc agctgacaag agatgtctac acagatccca tcgtgttcaa cccttctgca      960
aatgttggcc tctgccggag atggggcaac aacccctaca cacccttctc agagctggag     1020
aatgccttca tcaggccgcc gcacttcttc gaccgcctca cagcctcac catcagcagg     1080 aacagatttg atgttggaag caacttcatc gagccatgga cgcgcacac cttgaggagg     1140 agcttcctca cacctctgc tgttcaagaa gattcatatg ccagatcac caaccagagg     1200 accaccatca accttccagc aaatggaact ggaagagttg aaagcaccgc cgtggacttc     1260
agatctgctc tggtgggcat ctatggagtg aacagagctt ccttcatccc cggcggcgtg     1320
ttcaatggca ccacccagcc aagcaccggc ggctgccgag atctctatga ttcttcagat     1380
gagctgccgc cagaagaaag cagcggcacc ttcgagcacc gcctcagcca tgtcaccttc     1440
ttgagcttca ccaccaacca agctggaagc attgcaaatg ctggaagggt gccaacatat     1500
gtttggaccc acagagatgt tgatctaaac aacaccatca ccgccgacag gatcacccat     1560
cttcctctca tcaagagcaa tgttcaaaga gtggccgcg ccgtcaaggg gccaggcttc     1620
actggaggag atgtgctgag gatgagctcc tcagatgctg acatctccat catcggcatc     1680
accgccggcg ctcctctcac ccagcagtac aggatcaggc tgcgctatgc aagcaatgtt     1740
gatgtcacca tcaggctggt gaggcaggac acccaaagca acattggaag catcaacctc     1800
ctccgcacca tgaactcagg agaagaaagc agatatgaaa gctacaggac ggtggagatg     1860
ccaggaaact tcagaatgac aagcagctcg gcgcagatcc gcctcttcac ccaaggcctc     1920
cgcgtcaatg agagctgtt cctggacagc ttggagttca tccccgtcaa cccaacaaga     1980
gaagcagaag aagatctgga ggccgccaag aaggccgtca ccagcctctt caccaggtaa     2040
```

<210> SEQ ID NO 6
<211> LENGTH: 2040
<212> TYPE: DNA
<213> ORGANISM: Artificial
<220> FEATURE:
<223> OTHER INFORMATION: Axmi100 optimised sequence containing all
     AATAAA-like motifs present in the WT sequence (100-opt+pA)

<400> SEQUENCE: 6

```
atgaacagga ataatcaaaa tgaatgtgag atcattgatg ctcctcattg tggctgccct       60
tctgatgatg tggtgaaata tcctcttgct tcagatccaa atgctgctct ccaaaatatg      120
aactacaagg actacctcca aacatatgat ggagactaca ccgacagctt gattaatccc      180
aacctctcca ttaatactag agatgtgctg caaactggca tcaccattgt tggaaggata      240
ctaggcttcc tcggcgtccc cttgccggc cagctggtga ccttctacac cttcctcctc      300
aaccagctat ggccaacaaa tgacaatgct gtttgggagg ccttcatgga gcagattgaa      360
ggcatcattg ctcaaaggat ctccgagcaa gtggtgagaa atgctctgga tgctctcacc      420
```

```
ggaatacatg actactacga ggagtacctc gccgcgctgg aagaatggct ggagaggcca      480
tcaggagcaa gggccaacct cgccttccaa agatttgaga acctccacca gctgttcgtg      540
agccagatgc cctccttcgg cagcggccct ggatcagaaa gagatgctgt ggcgctgctc      600
accgtctatg ctcaagctgc caacctccat ctgctgctat aaaggatgc tgagatttat       660 ggagctagat ggggcctcca gcaaggccaa attaatctct acttcaatgc tcagcaggac      720
aggacaagga tctacaccaa ccactgcgtc gccacatata acagaggcct ggagatctc       780 cgcggcacca acactgaatc atggctgaac taccaccagt tcagaaggga gatgacatta     840
atggccatgg atctggtggc gctgttccca tactacaacc tccgccaata tccaaatgga     900
gctaatcctc agctgacaag agatgtctac acagatccca tcgtgttcaa cccttctgca     960
aatgttggcc tctgccggag atggggcaac aacccatata atacattctc agagctggag    1020
aatgccttca tcaggccgcc gcacttcttc gaccgcctca acagcctcac catcagcagg    1080
aacagatttg atgttggaag caacttcatc gagccatgga cgccacac cttgaggagg       1140 agcttcctca cacctctgc tgttcaagaa gattcatatg ccagatcac caatcaaagg      1200 accacaatta tcttccagc aaatggaact ggaagagttg aaagcaccgc cgtggacttc      1260
agatctgctc tggtgggcat ctatggagtg aacagagctt ccttcatccc cggcggcgtg    1320
ttcaatggca ccacccagcc aagcaccggc ggctgccgag atctctatga ttcttcagat    1380
gagctgccgc cagaagaaag cagcggcacc ttcgagcacc gcctcagcca tgtcaccttc   1440
ttgagcttca ccaccaacca agctggaagc attgcaaatg ctggaagggt gccaacatat    1500
gtttggaccc acagagatgt tgatctaaac aacaccatca ccgccgacag gatcacccat   1560
cttcctctca taaaatcaaa tgttcaaaga agtggccgcg ccgtcaaggg gccaggcttc   1620
actggaggag atgtgctgag gatgagctcc tcagatgctg acatctcaat aatcggcatc    1680
accgccggcg ctcctctcac ccagcagtac aggatcaggc tgcgctatgc aagcaatgtt    1740
gatgtcacca tcaggctggt gaggcaggac acccaaagca acattggaag cataaacctc    1800
ctccgcacca tgaactcagg agaagaaagc agatatgaaa gctacaggac ggtggagatg    1860 ccaggaaaact tcagaatgac aagcagctcg gcgcagatcc gcctcttcac ccaaggcctc    1920
cgcgtcaatg gagagctgtt cctggacagc ttggagttca tccccgtcaa cccaacaaga    1980
gaagcagaag aagatctgga ggccgccaag aaggccgtca ccagcctctt caccaggtaa   2040

<210> SEQ ID NO 7
<211> LENGTH: 5988
<212> TYPE: DNA
<213> ORGANISM: Artificial
<220> FEATURE:
<223> OTHER INFORMATION: pZmUbi-Axmi028(WT)-LUC-nosTerm

<400> SEQUENCE: 7
ctagagataa tgagcattgc atgtctaagt tataaaaaat taccacatat tttttttgtc       60
acacttgttt gaagtgcagt ttatctatct ttatacatat atttaaactt tactctacga      120
ataatataat ctatagtact acaataatat cagtgtttta gagaatcata taaatgaaca     180
gttagacatg gtctaaagga caattgagta ttttgacaac aggactctac agttttatct      240 tttagtgtg catgtgttct cctttttttt tttgcaaata gcttcaccta tataatactt       300
catccatttt attagtacat ccatttaggg tttagggtta atggtttta tagactaatt       360 tttttagtac atctatttta ttctattta gcctctaaat taagaaaact aaaactctat      420
```

```
tttagtttttt ttatttaata atttagatat aaaatagaat aaaataaagt gactaaaaat      480
taaacaaata cccttttaaga aattaaaaaa actaaggaaa cattttttctt gtttcgagta      540 gataatgcca gcctgttaaa cgccgtcgac gcagtctaac ggacaccaac cagcgaacca      600
gcagcgtcgc gtcgggccaa gcgaagcaga cggcacggca tctctgtcgc tgcctctgga      660
cccctctcga gagttccgct ccaccgttgg acttcgtccg ctgtcggcat ccagaaattg      720
cgtggcggag cggcagacgt gagccggcac ggcaggcggc ctcctcctcc tctcacggca      780
ccggcagcta cggggattc ctttcccacc gctccttcgc tttcccttcc tcgcccgccg      840
taataaatag acaccccctc cacaccctct ttccccaacc tcgtgttgtt cggagcgcac      900
acacacacaa ccagatctcc cccaaatcca cccgtcggca cctccgcttc aaggtacgcc      960
gctcgtcctc cccccccctc tctaccttct ctagatcggc gttccggtcc atggttaggg     1020
cccggtagtt ctacttctgt tcatgtttgt gttagatccg tgtttgtgtt agatccgtgc     1080
tgctagcgtt cgtacacgga tgcgacctgt acgtcagaca cgttctgatt gctaacttgc     1140
cagtgtttct ctttggggaa tcctgggatg gctctagccg ttccgcagac gggatcgatt     1200
tcatgatttt ttttgtttcg ttgcataggg tttggtttgc ccttttcctt tatttcaata     1260
tatgccgtgc acttgtttgt cgggtcatct tttcatgctt tttttttgtct tggttgtgat     1320 gatgtggtct ggttgggcgg tcgttctaga tcggagtaga attctgtttc aaactacctg     1380
gtggatttat taattttgga tctgtatgtg tgtgccatac atattcatag ttacgaattg     1440
aagatgatgg atggaaatat cgatctagga taggtataca tgttgatgcg ggttttactg     1500
atgcatatac agagatgctt tgttcgctt ggttgtgatg atgtggtgtg gttgggcggt     1560
cgttcattcg ttctagatcg gagtagaata ctgtttcaaa ctacctggtg tatttattaa     1620
ttttggaact gtatgtgtgt gtcatacatc ttcatagtta cgagtttaag atggatggaa     1680
atatcgatct aggataggta tacatgttga tgtgggtttt actgatgcat atacatgatg     1740
gcatatgcag catctattca tatgctctaa ccttgagtac ctatctatta taataaacaa     1800
gtatgtttta taattatttt gatcttgata tacttggatg atggcatatg cagcagctat     1860
atgtggattt ttttagccct gccttcatac gctatttatt tgcttggtac tgtttctttt     1920
gtcgatgctc accctgttgt ttggtgttac ttctgcaggt cgactctagt ggatccatga     1980
atcaaaaaaa ctatgaaatt ataggtgctt caacaaacgg cacaattgaa ttacctgaag     2040
attacaacac tatagtcagc ccctatgatg ctccagcatc cgttactaca actattgaaa     2100
ttactggaac catactaagc gatttaggtg ttccaggagc atcatcagtt agtttacttt     2160
tgaataaact tataaatcta ttatggccaa atgataccaa tactgtgtgg gggacattcg     2220
gaaaagaaac cgctgatctt ctaaatgaag tgttatctcc agatgatcca gtagtaaaag     2280
atgcaaatac cattttaaaa ggaataaacg atcccttaa cttatattta aatgcacttg     2340
aaatatggaa aaaagaccccc aacaacttaa ctaccataga gaatgtcaca gattactttc     2400
gtagtttgaa tgtggttttt acacatgata tgccttcatt tgctgtacct ggatatgaaa     2460
cgaagttatt aacaatttat gcacaagctg caaatcttca tttacttta ttaagagatg     2520 cttctaggtt tggagaaggt tggggactga ctcaagaaat cataaatact aactataatg     2580
atcaattacg attgacagca gaatacacgg accattgtgt aaagtggtac aacgcaggat     2640
tagaaaaatt aaaagggaat ttaactgggg aaaattggta tacttataat agatttcgta     2700
gagaaatgac gttaatggtg ttagacgtag ttgcattatt ccaaactac gatacacgaa     2760 tgtacccgat cggaacgtca tcagaactta caagaatgat ctatacagat ccaattgctt     2820
```

```
atacacaaag cgatccatgg tacaagataa catctctttc tttttcaaat attgaaaaca   2880
gtgcgattcc aagtccttct ttcttcaggt ggctaaaatc cgtttcaatt aatagccagt   2940
ggtgsggcag tggtcctagt caaacctact attgggttgg acatgaattg gtatattcta   3000
attcaaattc taatcaatca cttaaagtta aatatggaga ccctaattct tttattgagc   3060
cccctgattc tttcagtttt tcttctacgg atgtttacag aacaatatct gttgttagaa   3120
attcagtaag taattatata gtaagtgaag ttcgattcaa ttcaattagt agtacaaatc   3180
aaattagtga agaaatttat aaacatcaat caaattggag tagacaagaa accaaagatt   3240
caattacaga actatcctta gctgctaatc ccccaacaac atttggaaat gtagcagaat   3300
acagtcatag attagcatat atttcagagg cataccaaag tcacaaccca tcaaaatacc   3360
caacctacat tcctgtattc ggttggacgc atacaagcgt acgttacgat aataaaatct   3420
tcccggacaa aatcactcaa attccagctg ttaaaagctc ctcagcccaa ggtggatcat   3480
ggaaaaatat agtgaaaggc cccgggttta ctggaggaga tgtgacaact gcagtttcgc   3540
cagcaactgt aaccgacata ataaaaatac aagttactct agatccaaat tcactttcac   3600
aaaaatatcg tgcacgactt cgctatgctt ccaatgcatt tgtaccagct acattgtata   3660
caaatacaag tagtaattat aattttgaac ttaaaaaagg tacaactgaa cagtttacaa   3720
catataattc ataccagtat gtagatatcc caggttcaat acaatttaat aatacttctg   3780
atacagtctc tgtttatttg catatggatt caacatctaa tgtaaacgtt catgtagata   3840
gaattgaatt cattccaata gatgtaggat tgatggaaga cgccaaaaac ataaagaaag   3900
gcccggcgcc attctatccg ctagaggatg gaaccgctgg agagcaactg cataaggcta   3960
tgaagagata cgccctggtt cctgaacaa ttgcttttac agatgcacat atcgaggtga   4020
acattacgta agtttctgct tctacctttg atatatatat aataattatc attaattagt   4080
agtaatataa tatttcaaat attttttca aaataaaaga atgtagtata tagcaattgc   4140
ttttctgtag tttataagtg tgtatatttt aatttataac ttttctaata tatgaccaaa   4200
atttgttgat gtgcaggtac gcggaatact tcgaaatgtc cgttcggttg gcagaagcta   4260
tgaaacgata tgggctgaat acaaatcaca gaatcgtcgt atgcagtgaa aactctcttc   4320
aattctttat gccggtgttg ggcgcgttat ttatcggagt tgcagttgcg cccgcgaacg   4380
acatttataa tgaacgtgaa ttgctcaaca gtatgaacat ttcgcagcct accgtagtgt   4440
ttgtttccaa aaaggggttg caaaaaattt tgaacgtgca aaaaaaatta ccaataatcc   4500
agaaaattat tatcatggat tctaaaacgg attaccaggg atttcagtcg atgtacacgt   4560
tcgtcacatc tcatctacct cccggttta atgaatacga ttttgtacca gagtcctttg   4620
atcgtgacaa aacaattgca ctgataatga actcctctgg atctactggg ttacctaagg   4680
gtgtggccct tccgcataga actgcctgcg tcagattctc gcatgccaga gatcctattt   4740
ttggcaatca aatcattccg gatactgcga ttttaagtgt tgttccattc catcacggtt   4800
ttggaatgtt tactacactc ggatatttga tatgtggatt tcgagtcgtc ttaatgtata   4860
gatttgaaga agagctgttt ttacgatccc ttcaggatta caaaattcaa agtgcgttgc   4920
tagtaccaac cctattttca ttcttcgcca aaagcactct gattgacaaa tacgatttat   4980
ctaatttaca cgaaattgct tctgggggcg cacctctttc gaaagaagtc ggggaagcgg   5040
ttgcaaaacg cttccatctt ccagggatac gacaaggata tgggctcact gagactacat   5100
cagctattct gattacaccc gaggggatg ataaaccggg cgcggtcggt aaagttgttc   5160
```

| | |
|---|---|
| catttttga agcgaaggtt gtggatctgg ataccgggaa aacgctgggc gttaatcaga | 5220 |
| gaggcgaatt atgtgtcaga ggacctatga ttatgtccgg ttatgtaaac aatccggaag | 5280 |
| cgaccaacgc cttgattgac aaggatggat ggctacattc tggagacata gcttactggg | 5340 |
| acgaagacga acacttcttc atagttgacc gcttgaagtc tttaattaaa tacaaaggat | 5400 |
| accaggtggc ccccgctgaa ttggagtcga tattgttaca acaccccaac atcttcgacg | 5460 |
| cgggcgtggc aggtcttccc gacgatgacg ccggtgaact cccgccgcc gttgttgttt | 5520 |
| tggagcacgg aaagacgatg acggaaaaag agatcgtgga ttacgtcgcc agtcaagtaa | 5580 |
| caaccgcgaa aaagttgcgc ggaggagttg tgtttgtgga cgaagtaccg aaaggtctta | 5640 |
| ccggaaaact cgacgcaaga aaaatcagag agatcctcat aaaggccaag aagggcggaa | 5700 |
| agtccaaatt gtaaatgccg aatttccccg atcgttcaaa catttggcaa taaagtttct | 5760 |
| taagattgaa tcctgttgcc ggtcttgcga tgattatcat ataatttctg ttgaattacg | 5820 |
| ttaagcatgt aataattaac atgtaatgca tgacgttatt tatgagatgg ttttttatga | 5880 |
| ttagagtccc gcaattatac atttaatacg cgatagaaaa caaaatatag cgcgcaaact | 5940 |
| aggataaatt atcgcgcgcg gtgtcatcta tgttactaga tcgctcga | 5988 |

<210> SEQ ID NO 8
<211> LENGTH: 5985
<212> TYPE: DNA
<213> ORGANISM: Artificial
<220> FEATURE:
<223> OTHER INFORMATION: pZmUbi-Axmi028(opt)-LUC-nosTerm

<400> SEQUENCE: 8

| | |
|---|---|
| ctagagataa tgagcattgc atgtctaagt tataaaaaat taccacatat ttttttgtc | 60 |
| acacttgttt gaagtgcagt ttatctatct ttatacatat atttaaactt tactctacga | 120 |
| ataatataat ctatagtact acaataatat cagtgtttta gagaatcata taaatgaaca | 180 |
| gttagacatg gtctaaagga caattgagta ttttgacaac aggactctac agttttatct | 240 |
| ttttagtgtg catgtgttct ccttttttt tttgcaaata gcttcaccta tataatactt | 300 |
| catccatttt attagtacat ccatttaggg tttagggtta atggttttta tagctaatt | 360 |
| tttttagtac atctatttta ttctatttta gcctctaaat taagaaaact aaaactctat | 420 |
| tttagttttt ttatttaata atttagatat aaaatagaat aaaataaagt gactaaaaat | 480 |
| taaacaaata ccctttaaga aattaaaaaa actaaggaaa cattttttctt gtttcgagta | 540 |
| gataatgcca gcctgttaaa cgccgtcgac gcagtctaac ggacaccaac cagcgaacca | 600 |
| gcagcgtcgc gtcgggccaa gcgaagcaga cggcacggca tctctgtcgc tgcctctgga | 660 |
| ccctctcga gagttccgct ccaccgttgg acttcgtccg ctgtcggcat ccagaaattg | 720 |
| cgtggcggag cggcagacgt gagccggcac ggcaggcggc ctcctcctcc tctcacggca | 780 |
| ccggcagcta cgggggattc ctttcccacc gctccttcgc tttcccttcc tcgcccgccg | 840 |
| taataaatag acaccccctc cacaccctct ttccccaacc tcgtgttgtt cggagcgcac | 900 |
| acacacacaa ccagatctcc cccaaatcca cccgtcggca cctccgcttc aaggtacgcc | 960 |
| gctcgtcctc ccccccctc tctaccttct ctagatcggc gttccggtcc atggttaggg | 1020 |
| cccggtagtt ctacttctgt tcatgtttgt gttagatccg tgtttgtgtt agatccgtgc | 1080 |
| tgctagcgtt cgtacacgga tgcgacctgt acgtcagaca cgttctgatt gctaacttgc | 1140 |
| cagtgtttct ctttggggaa tcctgggatg gctctagccg ttccgcagac gggatcgatt | 1200 |
| tcatgatttt ttttgtttcg ttgcataggg tttggtttgc ccttttcctt tatttcaata | 1260 |

```
tatgccgtgc acttgtttgt cgggtcatct tttcatgctt ttttttgtct tggttgtgat    1320
gatgtggtct ggttgggcgg tcgttctaga tcggagtaga attctgtttc aaactacctg    1380
gtggatttat taattttgga tctgtatgtg tgtgccatac atattcatag ttacgaattg    1440
aagatgatgg atggaaatat cgatctagga taggtataca tgttgatgcg ggttttactg    1500
atgcatatac agagatgctt ttgttcgctt ggttgtgatg atgtggtgtg gttgggcggt    1560
cgttcattcg ttctagatcg gagtagaata ctgtttcaaa ctacctggtg tatttattaa    1620
ttttggaact gtatgtgtgt gtcatacatc ttcatagtta cgagtttaag atggatggaa    1680
atatcgatct aggataggta tacatgttga tgtgggtttt actgatgcat atacatgatg    1740
gcatatgcag catctattca tatgctctaa ccttgagtac ctatctatta aataaacaa     1800
gtatgtttta taattatttt gatcttgata tacttggatg atggcatatg cagcagctat    1860
atgtggattt ttttagcct gccttcatac gctatttatt tgcttggtac tgtttctttt     1920
gtcgatgctc accctgttgt ttggtgttac ttctgcaggt cgactctagt ggatccatga    1980
accagaagaa ctacgagatc atcggcgcgt ccaccaacgg gacgatcgag ctgcccgagg    2040
attacaacac gatcgtcagc ccgtacgacg cgcctgcatc agtgacaacc accatcgaga    2100
tcacggggac aatcctgtct gacctcggtg tgcctggagc aagttcagtc agccttctgc    2160
tcaacaagct gatcaacctg ctctggccga acgacaccaa caccgtgtgg ggtacgttcg    2220
gcaaggagac ggccgatctc ctcaacgagg tcctgtcacc tgatgaccca gttgtcaagg    2280
acgctaatac gatcctcaag gggatcaacg ggtcgctgaa cctctacctg aacgccctcg    2340
agatctggaa gaaggacccg aacaacctga ctactatcga gaacgtgact gactacttcc    2400
ggtcactcaa cgtcgtgttc acgcacgaca tgccctcgtt cgccgtccct ggatacgaga    2460
ccaagctgct caccatctac gcccaggctg caaacctcca tctgctgttg ctcagggacg    2520
catcacgttt cggtgaggga tggggtttga cccaggagat catcaacacg aactacaacg    2580
accagctccg cctcaccgcc gaatacaccg accactgcgt gaagtggtac aacgccggct    2640
tggagaagct gaagggcaac ctcacggggtg agaactggta cacgtacaac cggttccgca    2700
gggagatgac cctcatggtg ctggacgtgg tcgcattgtt cccaaactac gacacccgca    2760
tgtacccgat cgggacatca agcgagctta cccgtatgat ctacactgac cccatcgcct    2820
acacccagtc cgaccatgg tacaagatca cgtccctgag cttctcgaac atcgagaaca    2880
gcgcgatccc ctccccatcg ttcttccgct ggctcaagtc cgtcagcatt aactcccagt    2940
ggtggggttc cggaccttca caaacctact actgggtggg gcacgaactg gtctacagca    3000
acagcaacag caaccagtcg ctgaaggtga agtacggcga ccctaacagc ttcatcgagc    3060
ccccggattc cttctccttc agcagcacgg acgtgtacag gaccatctca gtcgtgcgta    3120
attccgtgtc gaactacatc gtgtcggagg tgcggttcaa cagcatctcc tccaccaacc    3180
agatcagcga ggaaatctac aagcaccagt ctaactggag ccggcaggag acaaaggact    3240
caatcaccga gctgagcctg ccgccaccc cgccaaccac gttcggaaac gttgccgagt     3300
acagtcaccg cctggcttac atctcagagg cgtaccagtc tcacaaccca tctaagtacc    3360
cgacctatat cccgtgttc gggtggaccc acacatccgt gaggtacgac aacaagattt     3420
tcccggacaa gatcacgcag atccccgcgg ttaagagtag ctcagctcag ggggaagct     3480
ggaagaaatat cgtcaagggg cccgattca cgggtggaga cgtgacgacg gcggttttcac     3540
ctgcaactgt tacggatatt atcaagatcc aggttaccct tgatcccaac agtctgagcc    3600
```

-continued

```
agaagtatcg ggcacgcctt cgctacgcca gcaacgcctt cgtcccggca acccttttata    3660
cgaacacctc gtcaaactac aacttcgaac tgaagaaggg cacgactgag cagttcacga    3720
cctacaacag ctaccagtac gtggacatcc ccggcagcat ccagttcaac aatacgtccg    3780
acaccgtgtc ggtctacctg cacatggact caacctcgaa cgtgaacgtg cacgtggacc    3840
ggatcgagtt catcccgatc gacggattga tggaagacgc caaaaacata aagaaaggcc    3900
cggcgccatt ctatccgcta gaggatgaaa ccgctggaga gcaactgcat aaggctatga    3960
agagatacgc cctggttcct ggaacaattg cttttacaga tgcacatatc gaggtgaaca    4020
ttacgtaagt ttctgcttct acctttgata tatatataat aattatcatt aattagtagt    4080
aatataatat ttcaaatatt tttttcaaaa taaaagaatg tagtatatag caattgcttt    4140
tctgtagttt ataagtgtgt atattttaat ttataacttt tctaatatat gaccaaaatt    4200
tgttgatgtg caggtacgcg gaatacttcg aaatgtccgt tcggttggca gaagctatga    4260
aacgatatgg gctgaataca aatcacagaa tcgtcgtatg cagtgaaaac tctcttcaat    4320
tctttatgcc ggtgttgggc gcgttattta tcggagttgc agttgcgccc gcgaacgaca    4380
tttataatga acgtgaattg ctcaacagta tgaacatttc gcagcctacc gtagtgtttg    4440
tttccaaaaa ggggttgcaa aaattttga acgtgcaaaa aaaattacca ataatccaga    4500
aaattattat catggattct aaaacggatt accagggatt tcagtcgatg tacacgttcg    4560
tcacatctca tctacctccc ggttttaatg aatacgattt tgtaccagag tcctttgatc    4620
gtgacaaaac aattgcactg ataatgaact cctctggatc tactgggtta cctaagggtg    4680
tggcccttcc gcatagaact gcctgcgtca gattctcgca tgccagagat cctattttg    4740
gcaatcaaat cattccggat actgcgattt taagtgttgt tccattccat cacggttttg    4800
gaatgtttac tacactcgga tatttgatat gtggatttcg agtcgtctta atgtatagat    4860
ttgaagaaga gctgttttta cgatcccttc aggattacaa aattcaaagt gcgttgctag    4920
taccaacccct atttcatttc ttcgccaaaa gcactctgat tgacaaatac gatttatcta    4980
atttacacga aattgcttct gggggcgcac ctctttcgaa agaagtcggg gaagcggttg    5040
caaaacgctt ccatcttcca gggatacgac aaggatatgg gctcactgag actacatcag    5100
ctattctgat tacacccgag ggggatgata aaccgggcgc ggtcggtaaa gttgttccat    5160
tttttgaagc gaaggttgtg gatctggata ccgggaaaac gctgggcgtt aatcagagag    5220
gcgaattatg tgtcagagga cctatgatta tgtccggtta tgtaaacaat ccggaagcga    5280
ccaacgcctt gattgacaag gatggatggc tacattctgg agacatagct tactgggacg    5340
aagacgaaca cttcttcata gttgaccgct tgaagtcttt aattaaatac aaaggatacc    5400
aggtggcccc cgctgaattg gagtcgatat tgttacaaca ccccaacatc ttcgacgcgg    5460
gcgtggcagg tcttcccgac gatgacgccg gtgaacttcc cgccgccgtt gttgttttgg    5520
agcacggaaa gacgatgacg gaaaagagaa tcgtggatta cgtcgccagt caagtaacaa    5580
ccgcgaaaaa gttgcgcgga ggagttgtgt ttgtggacga agtaccgaaa ggtcttaccg    5640
gaaaactcga cgcaagaaaa atcagagaga tcctcataaa ggccaagaag ggcggaaagt    5700
ccaaattgta aatgccgaat tcccccgatc gttcaaacat ttggcaataa agtttcttaa    5760
gattgaatcc tgttgccggt cttgcgatga ttatcatata atttctgttg aattacgtta    5820
agcatgtaat aattaacatg taatgcatga cgttatttat gagatgggtt tttatgatta    5880
gagtcccgca attatacatt taatacgcga tagaaaacaa aatatagcgc gcaaactagg    5940
ataaattatc gcgcgcggtg tcatctatgt tactagatcg ctcga                    5985
```

<210> SEQ ID NO 9
<211> LENGTH: 5985
<212> TYPE: DNA
<213> ORGANISM: Artificial
<220> FEATURE:
<223> OTHER INFORMATION: pZmUbi-Axmi028(opt+pA)-LUC-nosTerm

<400> SEQUENCE: 9

| | | | | | |
|---|---|---|---|---|---|
| ctagagataa | tgagcattgc | atgtctaagt | tataaaaaat | taccacatat | tttttttgtc | 60 |
| acacttgttt | gaagtgcagt | ttatctatct | ttatacatat | atttaaactt | tactctacga | 120 |
| ataatataat | ctatagtact | acaataatat | cagtgtttta | gagaatcata | taaatgaaca | 180 |
| gttagacatg | gtctaaagga | caattgagta | ttttgacaac | aggactctac | agttttatct | 240 |
| ttttagtgtg | catgtgttct | cctttttttt | tttgcaaata | gcttcaccta | tataatactt | 300 |
| catccatttt | attagtacat | ccatttaggg | tttagggtta | atggttttta | tagactaatt | 360 |
| ttttagtac | atctattta | ttctatttta | gcctctaaat | taagaaaact | aaaactctat | 420 |
| tttagttttt | ttatttaata | atttagatat | aaaatagaat | aaaataaagt | gactaaaaat | 480 |
| taaacaaata | ccctttaaga | aattaaaaaa | actaaggaaa | catttttctt | gtttcgagta | 540 |
| gataatgcca | gcctgttaaa | cgccgtcgac | gcagtctaac | ggacaccaac | cagcgaacca | 600 |
| gcagcgtcgc | gtcgggccaa | gcgaagcaga | cggcacggca | tctctgtcgc | tgcctctgga | 660 |
| cccctctcga | gagttccgct | ccaccgttgg | acttcgtccg | ctgtcggcat | ccagaaattg | 720 |
| cgtggcggag | cggcagacgt | gagccggcac | ggcaggcggc | ctcctcctcc | tctcacggca | 780 |
| ccggcagcta | cgggggattc | ctttcccacc | gctccttcgc | tttcccttcc | tcgcccgccg | 840 |
| taataaatag | acacccctc | cacaccctct | tccccaacc | tcgtgttgtt | cggagcgcac | 900 |
| acacacacaa | ccagatctcc | cccaaatcca | cccgtcggca | cctccgcttc | aaggtacgcc | 960 |
| gctcgtcctc | cccccccctc | tctaccttct | ctagatcggc | gttccggtcc | atggttaggg | 1020 |
| cccggtagtt | ctacttctgt | tcatgtttgt | gttagatccg | tgtttgtgtt | agatccgtgc | 1080 |
| tgctagcgtt | cgtacacgga | tgcgacctgt | acgtcagaca | cgttctgatt | gctaacttgc | 1140 |
| cagtgtttct | ctttggggaa | tcctgggatg | gctctagccg | ttccgcagac | gggatcgatt | 1200 |
| tcatgatttt | ttttgtttcg | ttgcataggg | tttggtttgc | ccttttcctt | tatttcaata | 1260 |
| tatgccgtgc | acttgtttgt | cgggtcatct | tttcatgctt | ttttttgtct | tggttgtgat | 1320 |
| gatgtggtct | ggttgggcgg | tcgttctaga | tcggagtaga | attctgtttc | aaactacctg | 1380 |
| gtggatttat | taattttgga | tctgtatgtg | tgtgccatac | atattcatag | ttacgaattg | 1440 |
| aagatgatgg | atggaaatat | cgatctagga | taggtataca | tgttgatgcg | ggttttactg | 1500 |
| atgcatatac | agagatgctt | tgttcgctt | ggttgtgatg | atgtggtgtg | ttgggcggt | 1560 |
| cgttcattcg | ttctagatcg | gagtagaata | ctgtttcaaa | ctacctggtg | tatttattaa | 1620 |
| ttttggaact | gtatgtgtgt | gtcatacatc | ttcatagtta | cgagtttaag | atggatggaa | 1680 |
| atatcgatct | aggataggta | tacatgttga | tgtgggtttt | actgatgcat | atacatgatg | 1740 |
| gcatatgcag | catctattca | tatgctctaa | ccttgagtac | ctatctatta | taataaacaa | 1800 |
| gtatgtttta | taattatttt | gatcttgata | tacttggatg | atggcatatg | cagcagctat | 1860 |
| atgtggattt | ttttagcccct | gccttcatac | gctatttatt | tgcttggtac | tgtttctttt | 1920 |
| gtcgatgctc | accctgttgt | ttggtgttac | ttctgcaggt | cgactctagt | ggatccatga | 1980 |
| atcaaaagaa | ctatgaaatc | atcggcgcgt | ccaccaacgg | gacgatcgag | ctgcccgagg | 2040 |

```
attcaacac gatcgtcagc ccgtacgacg cgcctgcatc agtgacaacc accatcgaga    2100
tcacggggac aatactatct gacctcggtg tgcctggagc aagttcagtc agccttctgc    2160
tcaataaact gatcaacctg ctctggccga acgacaccaa caccgtgtgg ggtacgttcg    2220
gcaaggagac ggccgatctc ctcaacgagg tcctgtcacc tgatgaccca gttgtcaagg    2280
acgctaatac gatcctcaag ggaataaacg ggtcgctgaa cctctacctg aacgccctcg    2340
agatctggaa gaaggacccg aacaacctga ctactatcga aacgtgact gactacttcc     2400 ggtcactcaa cgtcgtgttc acgcacgaca tgccctcgtt cgccgtccct ggatatgaaa    2460
ccaagctgct caccatctac gcccaggctg caaacctcca tctgctgttg ctcagggacg    2520
catcacgttt cggtgaggga tggggtttga cccaggagat cataaatact aactacaacg    2580
accagctccg cctcaccgcc gaatacaccg accactgcgt gaagtggtac aacgccggct    2640
tggagaaatt aaagggcaac ctcacggtg agaactggta cacgtacaac cggttccgca     2700
gggagatgac cctcatggtg ctggacgtgg tcgcattgtt cccaaactac gacacccgca    2760
tgtacccgat cgggacatca agcgagctta cccgtatgat ctacactgac cccatcgcct    2820
acacccagtc cgacccatgg tacaagatca cgtccctgag cttctcgaac atcgagaaca    2880
gcgcgatccc ctccccatcg ttcttccgct ggctcaagtc cgtctcaatt aattcccagt    2940
ggtggggttc cggaccttca caaacctact actgggtggg gcacgaactg gtctacagca    3000
acagcaacag caatcaatcg ctgaaggtga agtacgcga ccctaacagc ttcatcgagc     3060
ccccggattc cttctccttc agcagcacgg acgtgtacag gaccatctca gtcgtgcgta    3120
attccgtgtc gaactacatc gtgtcggagg tgcggttcaa cagcatctcc tccaccaatc    3180
aaatcagcga ggaaatctac aagcaccaat caaactggag ccggcaggaa accaaggact    3240
caatcaccga gctgagcctg gccgccaacc cgccaaccac gttcggaaac gttgccgaat    3300
acagtcaccg cctggcttac atctcagagg cgtaccagtc tcacaaccca tcaaaatacc    3360
cgacctatat cccccgtgttc gggtggaccc acacatccgt gaggtacgac aataaaattt    3420
tcccggacaa gatcacgcag atccccgcgg ttaagagtag ctcagctcag gggggaagct    3480
ggaaaaatat cgtcaagggg cccggattca cgggtggaga cgtgacgacg gcggtttcac    3540
ctgcaactgt tacggatata ataaaaatac aggttaccct tgatcccaac agtctgagcc    3600
aaaaatatcg ggcacgcctt cgctacgcca gcaacgcctt cgtcccggca acccttata     3660 cgaatacatc gtcaaactac aacttcgaac tgaagaaggg cacgactgag cagttcacga    3720
catataacag ctaccagtac gtggacatcc ccggctcaat acagttcaat aatacgtccg    3780
acaccgtgtc ggtctacctg cacatggact caacctcgaa cgtgaacgtg cacgtggacc    3840
ggatcgagtt catcccgatc gacggattga tggaagacgc caaaaacata agaaaaggcc    3900
cggcgccatt ctatccgcta gaggatggaa ccgctggaga gcaactgcat aaggctatga    3960
agagatacgc cctggttcct ggaacaattg cttttacaga tgcacatatc gaggtgaaca    4020
ttacgtaagt ttctgcttct acctttgata tatatataat aattatcatt aattagtagt    4080
aatataatat ttcaaatatt tttttcaaaa taaagaatg tagtatatag caattgcttt     4140
tctgtagttt ataagtgtgt atattttaat ttataacttt tctaatatat gaccaaaatt    4200
tgttgatgtg caggtacgcg gaatacttcg aaatgtccgt tcggttggca gaagctatga    4260
aacgatatgg gctgaataca aatcacagaa tcgtcgtatg cagtgaaaac tctcttcaat    4320
tctttatgcc ggtgttgggc gcgttatta tcggagttgc agttgcgccc gcgaacgaca     4380
tttataatga acgtgaattg ctcaacagta tgaacatttc gcagcctacc gtagtgtttg    4440
```

```
tttccaaaaa gggghttgcaa aaaatttta acgtgcaaaa aaaattacca ataatccaga      4500
aaattattat catggattct aaaacggatt accaggatt tcagtcgatg tacacgttcg       4560
tcacatctca tctacctccc ggttttaatg aatacgattt tgtaccagag tcctttgatc      4620
gtgacaaaac aattgcactg ataatgaact cctctggatc tactgggtta cctaagggtg      4680
tggcccttcc gcatagaact gcctgcgtca gattctcgca tgccagagat cctatttttg      4740
gcaatcaaat cattccggat actgcgattt taagtgttgt tccattccat cacggttttg      4800
gaatgtttac tacactcgga tatttgatat gtggatttcg agtcgtctta atgtatagat      4860
ttgaagaaga gctgttttta cgatcccttc aggattacaa aattcaaagt gcgttgctag      4920
taccaaccct attttcattc ttcgccaaaa gcactctgat tgacaaatac gatttatcta      4980
atttacacga aattgcttct gggggcgcac ctctttcgaa agaagtcggg gaagcggttg      5040
caaaacgctt ccatcttcca gggatacgac aaggatatgg gctcactgag actacatcag      5100
ctattctgat tacacccgag ggggatgata accgggcgc ggtcggtaaa gttgttccat        5160 ttttttgaagc gaaggttgtg gatctggata ccgggaaaac gctgggcgtt aatcagagag     5220
gcgaattatg tgtcagagga cctatgatta tgtccggtta tgtaaacaat ccggaagcga      5280
ccaacgcctt gattgacaag gatggatggc tacattctgg agacatagct tactgggacg     5340
aagacgaaca cttcttcata gttgaccgct tgaagtcttt aattaaatac aaaggatacc      5400
aggtggcccc cgctgaattg gagtcgatat tgttacaaca ccccaacatc ttcgacgcgg      5460
gcgtggcagg tcttcccgac gatgacgccg gtgaacttgcc cgccgccgtt gttgttttgg    5520
agcacggaaa gacgatgacg gaaaaagaga tcgtggatta cgtcgccagt caagtaacaa      5580
ccgcgaaaaa gttgcgcgga ggagttgtgt tgtggacgaa agtaccgaaa ggtcttaccg      5640
gaaaactcga cgcaagaaaa atcagagaga tcctcataaa ggccaagaag ggcggaaagt      5700
ccaaattgta aatgccgaat tcccccgatc gttcaaacat ttggcaataa agtttcttaa      5760
gattgaatcc tgttgccggt cttgcgatga ttatcatata atttctgttg aattacgtta      5820
agcatgtaat aattaacatg taatgcatga cgttatttat gagatgggtt tttatgatta     5880
gagtcccgca attatacatt taatacgcga tagaaaacaa aatatagcgc gcaaactagg      5940
ataaattatc gcgcgcggtg tcatctatgt tactagatcg ctcga                     5985
```

<210> SEQ ID NO 10
<211> LENGTH: 6135
<212> TYPE: DNA
<213> ORGANISM: Artificial
<220> FEATURE:
<223> OTHER INFORMATION: pZmUbi-Axmi100(WT)-LUC-nosTerm

<400> SEQUENCE: 10

```
ctagagataa tgagcattgc atgtctaagt tataaaaaat taccacatat tttttttgtc      60
acacttgttt gaagtgcagt ttatctatct ttatacatat atttaaactt tactctacga     120
ataatataat ctatagtact acaataatat cagtgtttta gagaatcata taaatgaaca     180
gttagacatg gtctaaagga caattgagta ttttgacaac aggactctac agttttatct     240
ttttagtgtg catgtgttct ccttttttttt ttgcaaata gcttcaccta tataatactt     300
catccatttt attagtacat ccatttaggg tttagggtta atggttttta tagactaatt     360
tttttagtac atctatttta ttctatttta gcctctaaat taagaaaact aaaactctat    420
tttagttttt ttatttaata atttgatatat aaaatagaat aaaataaagt gactaaaaat    480
```

-continued

| | |
|---|---|
| taaacaaata ccctttaaga aattaaaaaa actaaggaaa cattttttctt gtttcgagta | 540 |
| gataatgcca gcctgttaaa cgccgtcgac gcagtctaac ggacaccaac cagcgaacca | 600 |
| gcagcgtcgc gtcgggccaa gcgaagcaga cggcacggca tctctgtcgc tgcctctgga | 660 |
| ccctctcga gagttccgct ccaccgttgg acttcgtccg ctgtcggcat ccagaaattg | 720 |
| cgtggcggag cggcagacgt gagccggcac ggcaggcggc ctcctcctcc tctcacggca | 780 |
| ccggcagcta cggggattc ctttcccacc gctccttcgc tttcccttcc tcgcccgccg | 840 |
| taataaatag acacccctc cacaccctct ttccccaacc tcgtgttgtt cggagcgcac | 900 |
| acacacacaa ccagatctcc cccaaatcca cccgtcggca cctccgcttc aaggtacgcc | 960 |
| gctcgtcctc ccccccctc tctaccttct ctagatcggc gttccggtcc atggttaggg | 1020 |
| cccggtagtt ctacttctgt tcatgttttgt gttagatccg tgtttgtgtt agatccgtgc | 1080 |
| tgctagcgtt cgtacacgga tgcgacctgt acgtcagaca cgttctgatt gctaacttgc | 1140 |
| cagtgtttct ctttggggaa tcctgggatg gctctagccg ttccgcagac gggatcgatt | 1200 |
| tcatgatttt ttttgtttcg ttgcataggg tttggtttgc ccttttcctt tatttcaata | 1260 |
| tatgccgtgc acttgtttgt cgggtcatct tttcatgctt ttttttgtct tggttgtgat | 1320 |
| gatgtggtct ggttgggcgg tcgttctaga tcggagtaga attctgtttc aaactacctg | 1380 |
| gtggatttat taattttgga tctgtatgtg tgtgccatac atattcatag ttacgaattg | 1440 |
| aagatgatgg atgaaatat cgatctagga taggtataca tgttgatgcg ggttttactg | 1500 |
| atgcatatac agagatgctt ttgttcgctt ggttgtgatg atgtggtgtg gttgggcggt | 1560 |
| cgttcattcg ttctagatcg gagtagaata ctgtttcaaa ctacctggtg tatttattaa | 1620 |
| ttttggaact gtatgtgtgt gtcatacatc ttcatagtta cgagtttaag atggatggaa | 1680 |
| atatcgatct aggataggta tacatgttga tgtgggtttt actgatgcat atacatgatg | 1740 |
| gcatatgcag catctattca tatgctctaa ccttgagtac ctatctatta taataaacaa | 1800 |
| gtatgtttta taattatttt gatcttgata tacttggatg atggcatatg cagcagctat | 1860 |
| atgtggattt ttttagcccct gccttcatac gctatttatt tgcttggtac tgtttctttt | 1920 |
| gtcgatgctc accctgttgt ttggtgttac ttctgcaggt cgactctagt ggatccatga | 1980 |
| atcgaaataa tcaaaatgaa tgtgaaatta ttgatgcccc tcattgtgga tgtccgtcag | 2040 |
| atgatgttgt gaaatatcct ttggcaagtg acccaaatgc agcgttacaa aatatgaact | 2100 |
| ataaagatta tttacaaacg tatgatggag actatacaga ttctcttatt aatcctaact | 2160 |
| tatctattaa tactagggat gtactacaaa caggtattac tattgtggga agaatactag | 2220 |
| ggttttagg tgttccattt gcggggcaac tagttacttt ctataccttt tcttaaatc | 2280 |
| agttatggcc aactaatgat aatgcagtat gggaagcttt tatggaacaa atagaaggga | 2340 |
| ttatcgctca aagaatatcg gagcaagtag taaggaatgc gcttgatgcc ttaactggaa | 2400 |
| tacacgatta ttatgaggaa tatttagcgg cattagagga gtggctggaa agaccgagcg | 2460 |
| gcgcaagggc taacttagct tttcagaggt ttgaaaatct acatcaatta tttgtaagtc | 2520 |
| agatgccaag ttttggtagt ggtcctggta gtgaaagaga tgcggtagca ttgctgacag | 2580 |
| tatatgcaca agcagcgaat ctccatttgt tgttattaaa agatgcagaa atttatgggg | 2640 |
| cgagatgggg acttcaacaa ggccaaatta atttatattt taatgctcaa caagatcgca | 2700 |
| ctcgaatta taccaatcat tgtgtggcaa catataatag aggattagga gacttaagag | 2760 |
| gcacaaatac tgaaagttgg ttaaattacc atcaattccg tagagagatg acattaatgg | 2820 |
| caatggattt agtggcatta ttcccatact ataatttacg acaatatcca aacggggcaa | 2880 |

```
accctcagct tacacgtgat gtatatacag atccgattgt atttaatcca tcagctaatg    2940
taggattatg tagacgttgg ggcaataacc catataatac attttcggaa cttgaaaatg    3000
ccttcattcg cccgccacat tttttgata ggttgaatag tttaacaatt agtagaaata    3060
gatttgacgt tggatcaaac tttatagagc cttggtctgg acatacgtta cgccgtagtt    3120
ttctgaacac ttcggcagta caagaagata gttatggcca aattactaat caaagaacaa    3180
caattaatct accagctaat ggaactgggc gagtggagtc aacagcagta gattttcgta    3240
gcgcgcttgt ggggatatac ggcgttaata gagcttcttt tattcccggt ggtgtgttta    3300
atggcacgac tcaaccttct actgaggat gtagagattt gtatgattca agtgatgaat    3360
taccaccaga agaaagtagt ggaacgtttg aacataggtt atctcatgtt accttttaa    3420
gttttacaac taatcaggct ggatccatag ccaatgcagg gcgcgtccct acttatgtct    3480
ggacccatcg agatgtggac cttaataaca cgattactgc agatagaatt acacacttac    3540
cattgataaa atcaaatgtg caacgcagtg gtcgcgcagt aaaaggacca ggatttacag    3600
gaggagatgt actccgaatg tcatcaagtg atgctgatat atcaataata ggaataacgg    3660
caggtgcacc gctaacacaa caatatcgta taagattgcg ttatgcttca aatgtagatg    3720
ttactatccg tttagtgaga caggacaccc aaagtaatat aggaagcata aacttattac    3780
gtacaatgaa cagtggagag gagtcaaggt atgaatcata tcgtactgta gagatgcctg    3840
gtaattttag aatgactagt agttcagcac agattcgact atttactcaa ggacttcgag    3900
tgaatggaga attgtttctt gatagtcttg aatttatccc agttaatccg acacgtgagg    3960
cggaagagga tttagaagca gcgaagaaag cggtgacgag cttgtttaca cgtggattga    4020
tggaagacgc caaaaacata agaaaggcc cggcgccatt ctatccgcta gaggatggaa    4080
ccgctggaga gcaactgcat aaggctatga agagatacgc cctggttcct ggaacaattg    4140
ctttttacaga tgcacatatc gaggtgaaca ttacgtaagt ttctgcttct acctttgata    4200
tatatataat aattatcatt aattagtagt aatataatat ttcaaatatt tttttcaaaa    4260
taaaagaatg tagtatatag caattgcttt tctgtagttt ataagtgtgt atatttttaat    4320
ttataacttt tctaatatat gaccaaaatt tgttgatgtg caggtacgcg gaatacttcg    4380
aaatgtccgt tcggttggca gaagctatga acgatatgg gctgaataca atcacagaa    4440
tcgtcgtatg cagtgaaaac tctcttcaat tctttatgcc ggtgttgggc gcgttattta    4500
tcggagttgc agttgcgccc gcgaacgaca tttataatga acgtgaattg ctcaacagta    4560
tgaacatttc gcagcctacc gtagtgtttg ttttccaaaaa ggggttgcaa aaattttga    4620
acgtgcaaaa aaattacca ataatccaga aaattattat catggattct aaaacggatt    4680
accagggatt tcagtcgatg tacacgttcg tcacatctca tctacctccc ggttttaatg    4740
aatacgattt tgtaccagag tcctttgatc gtgacaaaac aattgcactg ataatgaact    4800
cctctggatc tactgggtta cctaagggtg tggccccttcc gcatagaact gcctgcgtca    4860
gattctcgca tgccagagat cctattttg gcaatcaaat cattccggat actgcgattt    4920
taagtgttgt tccattccat cacggttttg gaatgtttac tacactcgga tatttgatat    4980
gtggatttcg agtcgtctta atgtatagat ttgaagaaga gctgttttta cgatcccttc    5040
aggattacaa aattcaaagt gcgttgctag taccaaccct attttcattc ttcgccaaaa    5100
gcactctgat tgacaaatac gatttatcta atttacacga aattgcttct ggggcgcac    5160
ctctttcgaa agaagtcggg gaagcggttg caaaacgctt ccatcttcca gggatacgac    5220
```

```
aaggatatgg gctcactgag actacatcag ctattctgat tacacccgag ggggatgata      5280
aaccgggcgc ggtcggtaaa gttgttccat tttttgaagc gaaggttgtg gatctggata      5340
ccgggaaaac gctgggcgtt aatcagagag gcgaattatg tgtcagagga cctatgatta      5400
tgtccggtta tgtaaacaat ccggaagcga ccaacgcctt gattgacaag gatggatggc      5460
tacattctgg agacatagct tactgggacg aagacgaaca cttcttcata gttgaccgct      5520
tgaagtcttt aattaaatac aaaggatacc aggtggcccc cgctgaattg gagtcgatat      5580
tgttacaaca ccccaacatc ttcgacgcgg gcgtggcagg tcttcccgac gatgacgccg      5640
gtgaacttcc cgccgccgtt gttgttttgg agcacggaaa gacgatgacg gaaaaagaga      5700
tcgtggatta cgtcgccagt caagtaacaa ccgcgaaaaa gttgcgcgga ggagttgtgt      5760
tgtggacga agtaccgaaa ggtcttaccg gaaaactcga cgcaagaaaa atcagagaga      5820
tcctcataaa ggccaagaag ggcggaaagt ccaaattgta aatgccgaat tccccgatc       5880
gttcaaacat ttggcaataa agtttcttaa gattgaatcc tgttgccggt cttgcgatga      5940
ttatcatata atttctgttg aattacgtta agcatgtaat aattaacatg taatgcatga      6000
cgttatttat gagatgggtt tttatgatta gagtcccgca attatacatt taatacgcga      6060
tagaaaacaa aatatagcgc gcaaactagg ataaattatc gcgcgcggtg tcatctatgt      6120
tactagatcg ctcga                                                       6135
```

<210> SEQ ID NO 11
<211> LENGTH: 6135
<212> TYPE: DNA
<213> ORGANISM: Artificial
<220> FEATURE:
<223> OTHER INFORMATION: pZmUbi-Axmi100(opt)-LUC-nosTerm

<400> SEQUENCE: 11

```
ctagagataa tgagcattgc atgtctaagt tataaaaaat taccacatat ttttttttgtc      60
acacttgttt gaagtgcagt ttatctatct ttatacatat atttaaactt tactctacga     120
ataatataat ctatagtact acaataatat cagtgtttta gagaatcata taaatgaaca     180
gttagacatg gtctaaagga caattgagta ttttgacaac aggactctac agttttatct     240
ttttagtgtg catgtgttct ccttttttttt tttgcaaata gcttcaccta tataatactt     300
catccatttt attagtacat ccatttaggg tttagggtta atggttttta tagactaatt     360
ttttagtac atctatttta ttctattttta gcctctaaat taagaaaact aaaactctat     420
tttagttttt ttatttaata atttagatat aaaatagaat aaaataaagt gactaaaaat     480
taaacaaata cccctttaaga aattaaaaaa actaaggaaa cattttctcct gtttcgagta    540
gataatgcca gcctgttaaa cgccgtcgac gcagtctaac ggacaccaac cagcgaacca    600
gcagcgtcgc gtcgggccaa gcgaagcaga cggcacggca tctctgtcgc tgcctctgga    660
cccctctcga gagttccgct ccaccgttgg acttcgtccg ctgtcggcat ccagaaattg    720
cgtggcggag cggcagacgt gagccggcac ggcaggcggc ctcctcctcc tctcacggca    780
ccggcagcta cgggggattc ctttcccacc gctccttcgc tttcccttcc tcgcccgccg    840
taataaatag acccccctc cacccctct ttccccaacc tcgtgttgtt cggagcgcac    900
acacacacaa ccagatctcc cccaaatcca cccgtcggca cctccgcttc aaggtacgcc    960
gctcgtcctc cccccccctc tctaccttct ctagatcggc gttccggtcc atggttaggg   1020
cccggtagtt ctacttctgt tcatgtttgt gttagatccg tgtttgtgtt agatccgtgc   1080
tgctagcgtt cgtacacgga tgcgacctgt acgtcagaca cgttctgatt gctaacttgc   1140
```

```
cagtgtttct ctttggggaa tcctgggatg gctctagccg ttccgcagac gggatcgatt    1200
tcatgatttt ttttgtttcg ttgcataggg tttggtttgc ccttttcctt tatttcaata    1260
tatgccgtgc acttgtttgt cgggtcatct tttcatgctt tttttgtct tggttgtgat     1320 gatgtggtct ggttgggcgg tcgttctaga tcggagtaga attctgtttc aaactacctg    1380
gtggatttat taattttgga tctgtatgtg tgtgccatac atattcatag ttacgaattg    1440
aagatgatgg atggaaatat cgatctagga taggtataca tgttgatgcg ggttttactg    1500
atgcatatac agagatgctt ttgttcgctt ggttgtgatg atgtggtgtg gttgggcggt    1560
cgttcattcg ttctagatcg gagtagaata ctgtttcaaa ctacctggtg tatttattaa    1620
ttttggaact gtatgtgtgt gtcatacatc ttcatagtta cgagtttaag atggatggaa    1680
atatcgatct aggataggta tacatgttga tgtgggtttt actgatgcat atacatgatg    1740
gcatatgcag catctattca tatgctctaa ccttgagtac ctatctatta taataaacaa    1800
gtatgtttta taattatttt gatcttgata tacttggatg atggcatatg cagcagctat    1860
atgtggattt ttttagcccc gccttcatac gctatttatt tgcttggtac tgtttcttt    1920 gtcgatgctc accctgttgt ttggtgttac ttctgcaggt cgactctagt ggatccatga    1980
acaggaacaa ccaaaatgaa tgtgagatca ttgatgctcc tcattgtggc tgcccttctg    2040
atgatgtggt gaaatatcct cttgcttcag atccaaatgc tgctctccag aacatgaact    2100
acaaggacta cctccaaaca tatgatggag actacaccga cagcttgatc aaccccaacc    2160
tctccatcaa cacaagagat gtgctgcaaa ctggcatcac cattgttgga aggatcttgg    2220
gcttcctcgg cgtccccttc gccggccagc tggtgacctt ctacaccttc ctcctcaacc    2280
agctatggcc aacaaatgac aatgctgttt gggaggcctt catggagcag attgaaggca    2340
tcattgctca aaggatctcc gagcaagtgg tgagaaatgc tctggatgct ctcaccggca    2400
tccatgacta ctacgaggag tacctcgccg cgctggaaga atggctggag aggccatcag    2460
gagcaagggc caacctcgcc ttccaaagat ttgagaacct ccaccagctg ttcgtgagcc    2520
agatgccctc cttcggcagc ggccctggat cagaaagaga tgctgtggcg ctgctcaccg    2580
tctatgctca agctgccaac ctccatctgc tgctgctgaa ggatgctgag atttatggag    2640
ctagatgggg cctccagcaa ggccagatca acctctactt caatgctcag caggacagga    2700
caaggatcta caccaaccac tgcgtcgcca cctacaacag aggccttgga gatctccgcg    2760
gcaccaacac tgaatcatgg ctgaactacc accagttcag aagggagatg accttgatgg    2820
caatggatct ggtggcgctg ttcccctact acaacctccg ccaatatcca aatggagcta    2880
atcctcagct gacaagagat gtctacacag atcccatcgt gttcaaccct tctgcaaatg    2940
ttggcctctg ccgagatgg ggcaacaacc cctacaacac cttctcagag ctggagaatg    3000
ccttcatcag gccgccgcac ttcttcgacc gcctcaacag cctcaccatc agcaggaaca    3060
gatttgatgt tggaagcaac ttcatcgagc catggagcgg ccacaccttg aggaggagct    3120
tcctcaacac ctctgctgtt caagaagatt catatggcca gatcaccaac cagaggacca    3180
ccatcaacct tccagcaaat ggaactggaa gagttgaaag caccgccgtg gacttcagat    3240
ctgctctggt gggcatctat ggagtgaaca gagcttcctt catccccggc ggcgtgttca    3300
atggcaccac ccagccaagc accggcggct gccgagatct ctatgattct tcagatgagc    3360
tgccgccaga agaaagcagc ggcacccttcg agcaccgcct cagccatgtc accttcttga    3420
gcttcaccac caaccaagct ggaagcattg caaatgctgg aagggtgcca acatatgttt    3480
```

```
ggacccacag agatgttgat ctaaacaaca ccatcaccgc cgacaggatc acccatcttc    3540
ctctcatcaa gagcaatgtt caaagaagtg gccgcgccgt caaggggcca ggcttcactg    3600
gaggagatgt gctgaggatg agctcctcag atgctgacat ctccatcatc ggcatcaccg    3660
ccggcgctcc tctcacccag cagtacagga tcaggctgcg ctatgcaagc aatgttgatg    3720
tcactatcag gctggtgagg caggacaccc aaagcaacat tggaagcatc aacctcctcc    3780
gcaccatgaa ctcaggagaa gaaagcagat atgaaagcta caggacggtg gagatgccag    3840
gaaacttcag aatgacaagc agctcggcgc agatccgcct cttcacccaa ggcctccgcg    3900
tcaatggaga gctgttcctg gacagcttgg agttcatccc cgtcaaccca acaagagaag    3960
cagaagaaga tctggaggcc gccaagaagg ccgtcaccag cctcttcacc aggggattga    4020
tggaagacgc caaaaacata aagaaaggcc cggcgccatt ctatccgcta gaggatggaa    4080
ccgctggaga gcaactgcat aaggctatga agagatacgc cctggttcct ggaacaattg    4140
cttttacaga tgcacatatc gaggtgaaca ttacgtaagt ttctgcttct acctttgata    4200
tatatataat aattatcatt aattagtagt aatataaatt ttcaaatatt ttttcaaaa     4260 taaaagaatg tagtatatag caattgcttt tctgtagttt ataagtgtgt atattttaat    4320
ttataacttt tctaatatat gaccaaaatt tgttgatgtg caggtacgcg gaatacttcg    4380
aaatgtccgt tcggttggca gaagctatga acgatatgg gctgaataca aatcacagaa     4440
tcgtcgtatg cagtgaaaac tctcttcaat tcttttatgcc ggtgttgggc gcgttattta   4500
tcggagttgc agttgcgccc gcgaacgaca tttataatga acgtgaattg ctcaacagta    4560
tgaacatttc gcagcctacc gtagtgtttg tttccaaaaa ggggttgcaa aaattttga    4620 acgtgcaaaa aaattacca ataatccaga aaattattat catggattct aaaacggatt     4680
accagggatt tcagtcgatg tacacgttcg tcacatctca tctacctccc ggttttaatg    4740
aatacgattt tgtaccagag tcctttgatc gtgacaaaac aattgcactg ataatgaact    4800
cctctggatc tactgggtta cctaagggtg tggcccttcc gcatagaact gcctgcgtca    4860
gattctcgca tgccagagat cctatttttg gcaatcaaat cattccggat actgcgattt    4920
taagtgttgt tccattccat cacgttttg aatgtttac tacactcgga tatttgatat      4980
gtggatttcg agtcgtctta atgtatagat ttgaagaaga gctgttttta cgatcccttc    5040
aggattacaa aattcaaagt gcgttgctag taccaaccct attttcattc ttcgccaaaa    5100
gcactctgat tgacaaatac gatttatcta atttacacga aattgcttct ggggggcgcac   5160 ctctttcgaa agaagtcggg gaagcggttc aaaacgctt ccatcttcca gggatacgac     5220
aaggatatgg gctcactgag actacatcag ctattctgat tacacccgag ggggatgata    5280
aaccgggcgc ggtcggtaaa gttgttccat tttttgaagc gaaggttgtg gatctggata    5340
ccgggaaaac gctgggcgtt aatcagagag gcgaattatg tgtcagagga cctatgatta    5400
tgtccggtta tgtaaacaat ccggaagcga ccaacgcctt gattgacaag gatggatggc    5460
tacattctgg agacatagct tactgggacg aagacgaaca cttcttcata gttgaccgct    5520
tgaagtcttt aattaaatac aaaggatacc aggtggcccc cgctgaattg gagtcgatat    5580
tgttacaaca ccccaacatc ttcgacgcgg gcgtggcagg tcttcccgac gatgacgccg    5640
gtgaacttcc cgccgccgtt gttgttttgg agcacggaaa gacgatgacg gaaaagagag    5700
tcgtggatta cgtcgccagt caagtaacaa ccgcgaaaaa gttgcgcgga ggagttgtgt    5760
ttgtggacga agtaccgaaa ggtcttaccg gaaaactcga cgcaagaaaa atcagagaga    5820
tcctcataaa ggccaagaag ggcggaaagt ccaaattgta aatgccgaat tccccgatc    5880
```

-continued

```
gttcaaacat tggcaataa agtttcttaa gattgaatcc tgttgccggt cttgcgatga      5940
ttatcatata atttctgttg aattacgtta agcatgtaat aattaacatg taatgcatga      6000
cgttatttat gagatgggtt tttatgatta gagtcccgca attatacatt taatacgcga      6060
tagaaaacaa aatatagcgc gcaaactagg ataaattatc gcgcgcggtg tcatctatgt      6120
tactagatcg ctcga                                                       6135
```

<210> SEQ ID NO 12
<211> LENGTH: 6135
<212> TYPE: DNA
<213> ORGANISM: Artificial
<220> FEATURE:
<223> OTHER INFORMATION: pZmUbi-Axmi100(opt+pA)-LUC-nosTerm

<400> SEQUENCE: 12

```
ctagagataa tgagcattgc atgtctaagt tataaaaaat taccacatat ttttttttgtc      60 acacttgttt gaagtgcagt ttatctatct ttatacatat atttaaactt tactctacga     120
ataatataat ctatagtact acaataatat cagtgtttta gagaatcata taaatgaaca     180
gttagacatg gtctaaagga caattgagta ttttgacaac aggactctac agttttatct     240
ttttagtgtg catgtgttct ccttttttt tttgcaaata gcttcaccta tataatactt     300
catccatttt attagtacat ccatttaggg tttagggtta atggtttta tagactaatt     360 tttttagtac atctatttta ttctatttta gcctctaaat taagaaaact aaaactctat     420
tttagttttt ttatttaata atttagatat aaaatagaat aaaataaagt gactaaaaat     480
taaacaaata ccctttaaga aattaaaaaa actaaggaaa cattttttctt gtttcgagta     540 gataatgcca gcctgttaaa cgccgtcgac gcagtctaac ggacaccaac cagcgaacca     600
gcagcgtcgc gtcgggccaa gcgaagcaga cggcacggca tctctgtcgc tgcctctgga     660
cccctctcga gagttccgct ccaccgttgg acttcgtccg ctgtcggcat ccagaaattg     720
cgtggcggag cggcagacgt gagccggcac ggcaggcggc ctcctcctcc tctcacggca     780
ccggcagcta cggggattc ctttcccacc gctccttcgc tttcccttcc tcgcccgccg     840
taataaatag acaccccctc cacaccctct ttccccaacc tcgtgttgtt cggagcgcac     900
acacacacaa ccagatctcc cccaaatcca cccgtcggca cctccgcttc aaggtacgcc     960
gctcgtcctc ccccccctc tctaccttct ctagatcggc gttccggtcc atggttaggg    1020
cccggtagtt ctacttctgt tcatgtttgt gttagatccg tgtttgtgtt agatccgtgc    1080
tgctagcgtt cgtacacgga tgcgacctgt acgtcagaca cgttctgatt gctaacttgc    1140
cagtgtttct ctttggggaa tcctgggatg gctctagccg ttccgcagac gggatcgatt    1200
tcatgatttt ttttgtttcg ttgcataggg tttggtttgc ccttttcctt tatttcaata    1260
tatgccgtgc acttgtttgt cgggtcatct tttcatgctt ttttttgtct tggttgtgat    1320
gatgtggtct ggttgggcgg tcgttctaga tcggagtaga attctgtttc aaactacctg    1380
gtggatttat aattttgga tctgtatgtg tgtgccatac atattcatag ttacgaattg    1440
aagatgatgg atgaaatat cgatctagga taggtataca tgttgatgcg ggttttactg    1500
atgcatatac agagatgctt tgttcgctt ggttgtgatg atgtggtgtg gttgggcggt    1560
cgttcattcg ttctagatcg gagtagaata ctgtttcaaa ctacctggtg tatttattaa    1620
ttttggaact gtatgtgtgt gtcatacatc ttcatagtta cgagtttaag atggatggaa    1680
atatcgatct aggataggta tacatgttga tgtgggtttt actgatgcat atacatgatg    1740
```

-continued

```
gcatatgcag catctattca tatgctctaa ccttgagtac ctatctatta taataaacaa   1800
gtatgtttta taattatttt gatcttgata tacttggatg atggcatatg cagcagctat   1860
atgtggattt ttttagccct gccttcatac gctatttatt tgcttggtac tgtttctttt   1920
gtcgatgctc accctgttgt ttggtgttac ttctgcaggt cgactctagt ggatccatga   1980
acaggaataa tcaaaatgaa tgtgagatca ttgatgctcc tcattgtggc tgcccttctg   2040
atgatgtggt gaaatatcct cttgcttcag atccaaatgc tgctctccaa aatatgaact   2100
acaaggacta cctccaaaca tatgatggag actacaccga cagcttgatt aatcccaacc   2160
tctccattaa tactagagat gtgctgcaaa ctggcatcac cattgttgga aggatactag   2220
gcttcctcgg cgtccccttc gccggccagc tggtgacctt ctacaccttc ctcctcaacc   2280
agctatggcc aacaaatgac aatgctgttt gggaggcctt catggagcag attgaaggca   2340
tcattgctca aaggatctcc gagcaagtgg tgagaaatgc tctggatgct ctcaccggaa   2400
tacatgacta ctacgaggag tacctcgccg cgctggaaga atggctggag aggccatcag   2460
gagcaagggc caacctcgcc ttccaaagat ttgagaacct ccaccagctg ttcgtgagcc   2520
agatgccctc cttcggcagc ggccctggat cagaaagaga tgctgtggcg ctgctcaccg   2580
tctatgctca agctgccaac ctccatctgc tgctattaaa ggatgctgag atttatggag   2640
ctagatgggg cctccagcaa ggccaaatta atctctactt caatgctcag caggacagga   2700
caaggatcta caccaaccac tgcgtcgcca catataacag aggccttgga gatctccgcg   2760
gcaccaacac tgaatcatgg ctgaactacc accagttcag aagggagatg acattaatgg   2820
ccatggatct ggtggcgctg ttcccatact acaacctccg ccaatatcca aatggagcta   2880
atcctcagct gacaagagat gtctacacag atcccatcgt gttcaaccct tctgcaaatg   2940
ttggcctctg ccgagatggg ggcaacaacc catataatac attctcagag ctggagaatg   3000
ccttcatcag gccgccgcac ttcttcgacc gcctcaacag cctcaccatc agcaggaaca   3060
gatttgatgt tggaagcaac ttcatcgagc catggagcgg ccacaccttg aggaggagct   3120
tcctcaacac ctctgctgtt caagaagatt catatggcca gatcaccaat caaaggacca   3180
caattaatct tccagcaaat ggaactggaa gagttgaaag caccgccgtg gacttcagat   3240
ctgctctggt gggcatctat ggagtgaaca gagcttcctt catccccggc ggcgtgttca   3300
atggcaccac ccagccaagc accggcggct gccgagatct ctatgattct tcagatgagc   3360
tgccgccaga gaaagcagc ggcaccttcg agcaccgcct cagccatgtc accttcttga   3420
gcttcaccac caaccaagct ggaagcattg caaatgctgg aagggtgcca acatatgttt   3480
ggacccacag agatgttgat ctaaacaaca ccatcaccgc cgacaggatc acccatcttc   3540
ctctcataaa atcaaatgtt caagaagtg ccgcgccgt caaggggcca ggcttcactg   3600
gaggagatgt gctgaggatg agctcctcag atgctgacat ctcaataatc ggcatcaccg   3660
ccggcgctcc tctcacccag cagtacagga tcaggctgcg ctatgcaagc aatgttgatg   3720
tcaccatcag gctggtgagg caggacaccc aaagcaacat tggaagcata aacctcctcc   3780
gcaccatgaa ctcaggagaa gaaagcagat atgaaagcta caggacggtg gagatgccag   3840
gaaacttcag aatgacaagc agctcggcgc agatccgcct cttcacccaa ggcctccgcg   3900
tcaatggaga gctgttcctg gacagcttgg agttcatccc cgtcaaccca acaagagaag   3960
cagaagaaga tctggaggcc gccaagaagg ccgtcaccag cctcttcacc agggggattga   4020
tggaagacgc caaaaacata aagaaggcc cggcgccatt ctatccgcta gaggatggaa   4080
ccgctggaga gcaactgcat aaggctatga agagatacgc cctggttcct ggaacaattg   4140
```

```
cttttacaga tgcacatatc gaggtgaaca ttacgtaagt ttctgcttct acctttgata    4200
tatatataat aattatcatt aattagtagt aatataatat ttcaaatatt tttttcaaaa    4260
taaaagaatg tagtatatag caattgcttt tctgtagttt ataagtgtgt atattttaat    4320
ttataacttt tctaatatat gaccaaaatt tgttgatgtg caggtacgcg gaatacttcg    4380
aaatgtccgt tcggttggca gaagctatga acgatatgg gctgaataca aatcacagaa    4440
tcgtcgtatg cagtgaaaac tctcttcaat tctttatgcc ggtgttgggc gcgttattta    4500
tcggagttgc agttgcgccc gcgaacgaca tttataatga acgtgaattg ctcaacagta    4560
tgaacatttc gcagcctacc gtagtgtttg tttccaaaaa ggggttgcaa aaattttga    4620 acgtgcaaaa aaattacca ataatccaga aaattattat catggattct aaaacggatt    4680
accagggatt tcagtcgatg tacacgttcg tcacatctca tctacctccc ggttttaatg    4740
aatacgattt tgtaccagag tcctttgatc gtgacaaaac aattgcactg ataatgaact    4800
cctctggatc tactgggtta cctaagggtg tggcccttcc gcatagaact gcctgcgtca    4860
gattctcgca tgccagagat cctatttttg gcaatcaaat cattccggat actgcgattt    4920
taagtgttgt tccattccat cacggttttgt gaatgtttac tacactcgga tatttgatat    4980
gtggatttcg agtcgtctta atgtatagat ttgaagaaga gctgttttta cgatcccttc    5040
aggattacaa aattcaaagt gcgttgctag taccaaccct atttttcattc ttcgccaaaa    5100 gcactctgat tgacaaatac gatttatcta atttacacga aattgcttct gggggcgcac    5160
ctctttcgaa agaagtcggg gaagcggttg caaaacgctt ccatcttcca gggatacgac    5220
aaggatatgg gctcactgag actacatcag ctattctgat tacacccgag ggggatgata    5280
aaccgggcgc ggtcggtaaa gttgttccat tttttgaagc gaaggttgtg gatctgggata    5340 ccgggaaaac gctgggcgtt aatcagagag gcgaattatg tgtcagagga cctatgatta    5400
tgtccggtta tgtaaacaat ccggaagcga ccaacgcctt gattgacaag gatggatggc    5460
tacattctgg agacatagct tactgggacg aagacgaaca cttcttcata gttgaccgct    5520
tgaagtcttt aattaaatac aaaggatacc aggtggcccc cgctgaattg gagtcgatat    5580
tgttacaaca ccccaacatc ttcgacgcgg gcgtggcagg tcttcccgac gatgacgccg    5640
gtgaacttcc cgccgccgtt gttgttttgg agcacggaaa gacgatgacg gaaaagagaa    5700
tcgtggatta cgtcgccagt caagtaacaa ccgcgaaaa gttgcgcgga ggagttgtgt    5760
ttgtggacga agtaccgaaa ggtcttaccg gaaaactcga cgcaagaaaa atcagagaga    5820
tcctcataaa ggccaagaag ggcggaaagt ccaaattgta aatgccgaat tccccgatc    5880 gttcaaacat ttggcaataa agtttcttaa gattgaatcc tgttgccggt cttgcgatga    5940
ttatcatata atttctgttg aattacgtta agcatgtaat aattaacatg taatgcatga    6000
cgttatttat gagatgggtt tttatgatta gagtcccgca attatacatt taatacgcga    6060
tagaaaacaa aatatagcgc gcaaactagg ataaattatc gcgcgcggtg tcatctatgt    6120
tactagatcg ctcga                                                     6135
```

<210> SEQ ID NO 13
<211> LENGTH: 1890
<212> TYPE: DNA
<213> ORGANISM: Artificial
<220> FEATURE:
<223> OTHER INFORMATION: Axmi028 optimised sequence containing 3
      AATAAA-like motifs present in the WT sequence (028-opt+3pA)

<400> SEQUENCE: 13

```
atgaaccaga agaactacga gatcatcggc gcgtccacca acgggacgat cgagctgccc      60
gaggattaca acacgatcgt cagcccgtac gacgcgcctg catcagtgac aaccaccatc     120
gagatcacgg ggacaatcct gtctgacctc ggtgtgcctg agcaagttc agtcagcctt      180 ctgctcaaca agctgatcaa cctgctctgg ccgaacgaca ccaacaccgt gtggggtacg     240
ttcggcaagg agacggccga tctcctcaac gaggtcctgt cacctgatga cccagttgtc     300
aaggacgcta atacgatcct caaggggatc aacgggtcgc tgaacctcta cctgaacgcc     360
ctcgagatct ggaagaagga cccgaacaac ctgactacta cgagaacgt gactgactac      420 ttccggtcac tcaacgtcgt gttcacgcac gacatgccct cgttcgccgt ccctggatac     480
gagaccaagc tgctcaccat ctacgcccag gctgcaaacc tccatctgct gttgctcagg     540
gacgcatcac gtttcggtga gggatggggt ttgacccagg agatcatcaa cacgaactac     600
aacgaccagc tccgcctcac cgccgaatac accgaccact gcgtgaagtg gtacaacgcc     660
ggcttggaga agctgaaggg caacctcacg ggtgagaact ggtacacgta caaccggttc     720
cgcagggaga tgaccctcat ggtgctggac gtggtcgcat tgttcccaaa ctacgacacc     780
cgcatgtacc cgatcgggac atcaagcgag cttacccgta tgatctacac tgaccccatc     840
gcctacaccc agtccgaccc atggtacaag atcacgtccc tgagcttctc gaacatcgag     900
aacagcgcga tccctccccc atcgttcttc cgctggctca agtccgtcag cattaactcc     960
cagtggtggg gttccggacc ttcacaaacc tactactggg tggggcacga actggtctac    1020
agcaacagca cagcaatca atcgctgaag gtgaagtacg gcgaccctaa cagcttcatc     1080
gagccccggg attccttctc cttcagcagc acggacgtgt acaggaccat ctcagtcgtg    1140
cgtaattccg tgtcgaacta catcgtgtcg gaggtgcggt tcaacagcat ctcctccacc    1200
aaccagatca gcgaggaaat ctacaagcac caatcaaact ggagccggca ggagacaaag    1260
gactcaatca ccgagctgag cctggccgcc aacccgccaa ccacgttcgg aaacgttgcc    1320
gagtacagtc accgcctggc ttacatctca gaggcgtacc agtctcacaa cccatctaag    1380
tacccgacct atatccccgt gttcgggtgg acccacacat ccgtgaggta cgacaacaag    1440 atttttcccgg acaagatcac gcagatcccc gcggttaaga gtagctcagc tcaggggga     1500 agctggaaga atatcgtcaa ggggcccgga ttcacgggtg agacgtgac gacggcggtt     1560 tcacctgcaa ctgttacgga tattatcaag atccaggtta cccttgatcc caacagtctg    1620
agccagaagt atcgggcacg ccttcgctac gccagcaacg ccttcgtccc ggcaacccctt   1680 tatacgaaca cctcgtcaaa ctacaacttc gaactgaaga agggcacgac tgagcagttc    1740
acgacctaca acagctacca gtacgtggac atccccggca gcatccagtt caacaatacg    1800
tccgacaccg tgtcggtcta cctgcacatg gactcaacct cgaacgtgaa cgtgcacgtg    1860
gaccggatcg agttcatccc gatcgactga                                     1890
```

<210> SEQ ID NO 14
<211> LENGTH: 2040
<212> TYPE: DNA
<213> ORGANISM: Artificial
<220> FEATURE:
<223> OTHER INFORMATION: Axmi100 optimised sequence containing 3
      AATAAA-like motifs present in the WT sequence (100-opt+3pA)

<400> SEQUENCE: 14

```
atgaacagga acaatcaaaa tgaatgtgag atcattgatg ctcctcattg tggctgccct      60
tctgatgatg tggtgaaata tcctcttgct tcagatccaa atgctgctct ccagaacatg     120
```

```
aactacaagg actacctcca aacatatgat ggagactaca ccgacagctt gatcaacccc    180
aacctctcca tcaacacaag agatgtgctg caaactggca tcaccattgt tggaaggatc    240
ttgggcttcc tcggcgtccc cttcgccggc cagctggtga ccttctacac cttcctcctc    300
aaccagctat ggccaacaaa tgacaatgct gtttgggagg ccttcatgga gcagattgaa    360
ggcatcattg ctcaaaggat ctccgagcaa gtggtgagaa atgctctgga tgctctcacc    420
ggcatccatg actactacga ggagtacctc gccgcgctgg aagaatggct ggagaggcca    480
tcaggagcaa gggccaacct cgccttccaa agatttgaga acctccacca gctgttcgtg    540
agccagatgc cctccttcgg cagcggccct ggatcagaaa gagatgctgt ggcgctgctc    600
accgtctatg ctcaagctgc caacctccat ctgctgctgc tgaaggatgc tgagatttat    660
ggagctagat ggggcctcca gcaaggccag atcaacctct acttcaatgc tcagcaggac    720
aggacaagga tctacaccaa ccactgcgtc gccacctaca acagaggcct ggagatctc    780 cgcggcacca acactgaatc atggctgaac taccaccagt tcagaaggga gatgaccttg    840
atggccatgg atctggtggc gctgttcccc tactacaacc tccgccaata tccaaatgga    900
gctaatcctc agctgacaag agatgtctac acagatccca tcgtgttcaa cccttctgca    960
aatgttggcc tctgccggag atggggcaac aaccccctaca cacccttctc agagctggag    1020
aatgccttca tcaggccgcc gcacttcttc gaccgcctca cagcctcac catcagcagg    1080 aacagatttg atgttggaag caacttcatc gagccatgga gcggccacac cttgaggagg    1140
agcttcctca cacctctgc tgttcaagaa gattcatatg ccagatcac caatcaaagg    1200 accaccatca accttccagc aaatggaact ggaagagttg aaagcaccgc cgtggacttc    1260
agatctgctc tggtgggcat ctatggagtg aacagagctt ccttcatccc cggcggcgtg    1320
ttcaatggca ccacccagcc aagcaccggc ggctgccgag atctctatga ttcttcagat    1380
gagctgccgc cagaagaaag cagcggcacc ttcgagcacc gcctcagcca tgtcaccttc    1440
ttgagcttca ccaccaacca agctggaagc attgcaaatg ctggaagggt gccaacatat    1500
gtttggaccc cagagatgt tgatctaaac aacaccatca ccgccgacag gatcacccat    1560
cttcctctca tcaagagcaa tgttcaaaga agtggccgcg ccgtcaaggg gccaggcttc    1620
actggaggag atgtgctgag gatgagctcc tcagatgctg acatctccat catcggcatc    1680
accgccggcg ctcctctcac ccagcagtac aggatcaggt gcgctatgc aagcaatgtt    1740 gatgtcacca tcaggctggt gaggcaggac acccaaagca acattggaag catcaacctc    1800
ctccgcacca tgaactcagg agaagaaagc agatatgaaa gctacaggac ggtggagatg    1860 ccaggaaaact tcagaatgac aagcagctcg gcgcagatcc gcctcttcac ccaaggcctc    1920
cgcgtcaatg agagctgtt cctggacagc ttggagttca tccccgtcaa cccaacaaga    1980
gaagcagaag aagatctgga ggccgccaag aaggccgtca ccagcctctt caccaggtaa    2040
```

<210> SEQ ID NO 15
<211> LENGTH: 5985
<212> TYPE: DNA
<213> ORGANISM: Artificial
<220> FEATURE:
<223> OTHER INFORMATION: pZmUbi-Axmi028(opt+3pA)-LUC-nosTerm

<400> SEQUENCE: 15

```
ctagagataa tgagcattgc atgtctaagt tataaaaaat taccacatat tttttttgtc     60
acacttgttt gaagtgcagt ttatctatct ttatacatat atttaaactt tactctacga    120
```

```
ataatataat ctatagtact acaataatat cagtgtttta gagaatcata taaatgaaca    180
gttagacatg gtctaaagga caattgagta ttttgacaac aggactctac agttttatct    240 tttttagtgtg catgtgttct cctttttttt tttgcaaata gcttcaccta tataatactt    300
catccatttt attagtacat ccatttaggg tttagggtta atggttttta tagactaatt    360
tttttagtac atctatttta ttctatttta gcctctaaat taagaaaact aaaactctat    420
tttagttttt ttatttaata atttagatat aaaatagaat aaaataaagt gactaaaaat    480
taaacaaata ccctttaaga aattaaaaaa actaaggaaa catttttctt gtttcgagta    540
gataatgcca gcctgttaaa cgccgtcgac gcagtctaac ggacaccaac cagcgaacca    600
gcagcgtcgc gtcgggccaa gcgaagcaga cggcacggca tctctgtcgc tgcctctgga    660 ccctctcga gagttccgct ccaccgttgg acttcgtccg ctgtcggcat ccagaaattg    720
cgtggcggag cggcagacgt gagccggcac ggcaggcggc ctcctcctcc tctcacggca    780
ccggcagcta cgggggattc ctttcccacc gctccttcgc tttcccttcc tcgcccgccg    840
taataaatag acacccctc cacaccctct ttccccaacc tcgtgttgtt cggagcgcac    900
acacacacaa ccagatctcc cccaaatcca cccgtcggca cctccgcttc aaggtacgcc    960
gctcgtcctc cccccccctc tctaccttct ctagatcggc gttccggtcc atggttaggg    1020
cccggtagtt ctacttctgt tcatgtttgt gttagatccg tgtttgtgtt agatccgtgc    1080
tgctagcgtt cgtacacgga tgcgacctgt acgtcagaca cgttctgatt gctaacttgc    1140
cagtgtttct ctttggggaa tcctgggatg gctctagccg ttccgcagac gggatcgatt    1200
tcatgatttt ttttgtttcg ttgcataggg tttggtttgc cctttccctt tatttcaata    1260
tatgccgtgc acttgtttgt cgggtcatct tttcatgctt ttttttgtct tggttgtgat    1320
gatgtggtct ggttgggcgg tcgttctaga tcggagtaga attctgtttc aaactacctg    1380
gtggatttat taattttgga tctgtatgtg tgtgccatac atattcatag ttacgaattg    1440
aagatgatgg atggaaatat cgatctagga taggtataca tgttgatgcg ggttttactg    1500
atgcatatac agagatgctt ttgttcgctt ggttgtgatg atgtggtgtg gttgggcggt    1560
cgttcattcg ttctagatcg gagtagaata ctgtttcaaa ctacctggtg tatttattaa    1620
ttttggaact gtatgtgtgt gtcatacatc ttcatagtta cgagtttaag atggatggaa    1680
atatcgatct aggataggta tacatgttga tgtgggtttt actgatgcat atacatgatg    1740
gcatatgcag catctattca tatgctctaa ccttgagtac ctatctatta taataaacaa    1800
gtatgtttta taattatttt gatcttgata tacttggatg atggcatatg cagcagctat    1860
atgtggattt ttttagccct gccttcatac gctatttatt tgcttggtac tgtttctttt    1920
gtcgatgctc accctgttgt ttggtgttac ttctgcaggt cgactctagt ggatccatga    1980
accagaagaa ctacgagatc atcggcgcgt ccaccaacgg gacgatcgag ctgcccgagg    2040
attacaacac gatcgtcagc ccgtacgacg cgcctgcatc agtgacaacc accatcgaga    2100
tcacggggac aatcctgtct gacctcggtg tgcctggagc aagttcagtc agccttctgc    2160
tcaacaagct gatcaacctg ctctggccga acgacaccaa caccgtgtgg ggtacgttcg    2220
gcaaggagac ggccgatctc ctcaacgagg tcctgtcacc tgatgaccca gttgtcaagg    2280
acgctaatac gatcctcaag gggatcaacg ggtcgctgaa cctctacctg aacgccctcg    2340
agatctggaa gaaggacccg aacaacctga ctactatcga aacgtgact gactacttcc    2400 ggtcactcaa cgtcgtgttc acgcacgaca tgccctcgtt cgccgtccct ggatacgaga    2460
ccaagctgct caccatctac gcccaggctg caaacctcca tctgctgttg ctcagggacg    2520
```

```
catcacgttt cggtgaggga tggggtttga cccaggagat catcaacacg aactacaacg    2580
accagctccg cctcaccgcc gaatacaccg accactgcgt gaagtggtac aacgccggct    2640
tggagaagct gaagggcaac ctcacgggtg agaactggta cacgtacaac cggttccgca    2700
gggagatgac cctcatggtg ctggacgtgg tcgcattgtt cccaaactac gacacccgca    2760
tgtacccgat cgggacatca agcgagctta cccgtatgat ctacactgac cccatcgcct    2820
acacccagtc cgacccatgg tacaagatca cgtccctgag cttctcgaac atcgagaaca    2880
gcgcgatccc ctccccatcg ttcttccgct ggctcaagtc cgtcagcatt aactcccagt    2940
ggtggggttc cggaccttca caaacctact actgggtggg gcacgaactg gtctacagca    3000
acagcaacag caatcaatcg ctgaaggtga agtacggcga ccctaacagc ttcatcgagc    3060
ccccggattc cttctccttc agcagcacgg acgtgtacag gaccatctca gtcgtgcgta    3120
attccgtgtc gaactacatc gtgtcggagg tgcggttcaa cagcatctcc tccaccaacc    3180
agatcagcga ggaaatctac aagcaccaat caaactggag ccggcaggag acaaaggact    3240
caatcaccga gctgagcctg ccgccaacc cgccaaccac gttcggaaac gttgccgagt    3300
acagtcaccg cctggcttac atctcagagg cgtaccagtc tcacaaccca tctaagtacc    3360
cgacctatat ccccgtgttc gggtggaccc acacatccgt gaggtacgac aacaagattt    3420
tcccggacaa gatcacgcag atccccgcgg ttaagagtag ctcagctcag ggggaagct    3480 ggaagaatat cgtcaagggg cccggattca cgggtggaga cgtgacgacg gcggtttcac    3540
ctgcaactgt tacggatatt atcaagatcc aggttaccct tgatcccaac agtctgagcc    3600
agaagtatcg ggcacgcctt cgctacgcca gcaacgcctt cgtcccggca acctttata    3660 cgaacacctc gtcaaactac aacttcgaac tgaagaaggg cacgactgag cagttcacga    3720
cctacaacag ctaccagtac gtggacatcc ccggcagcat ccagttcaac aatacgtccg    3780
acaccgtgtc ggtctacctg cacatggact caacctcgaa cgtgaacgtg cacgtggacc    3840
ggatcgagtt catcccgatc gacggattga tggaagacgc caaaaacata aagaaaggcc    3900
cggcgccatt ctatccgcta gaggatggaa ccgctggaga gcaactgcat aaggctatga    3960
agagatacgc cctggttcct ggaacaattg ctttttacaga tgcacatatc gaggtgaaca    4020
ttacgtaagt ttctgcttct acctttgata tatatataat aattatcatt aattagtagt    4080
aatataatat ttcaaatatt tttttcaaaa taaaagaatg tagtatatag caattgcttt    4140
tctgtagttt ataagtgtgt atattttaat ttataacttt tctaatatat gaccaaaatt    4200
tgttgatgtg caggtacgcg gaatacttcg aaatgtccgt tcggttggca gaagctatga    4260
aacgatatgg gctgaataca aatcacagaa tcgtcgtatg cagtgaaaac tctcttcaat    4320
tctttatgcc ggtgttgggc gcgttattta tcggagttgc agttgcgccc gcgaacgaca    4380
tttataatga acgtgaattg ctcaacagta tgaacatttc gcagcctacc gtagtgtttg    4440
tttccaaaaa ggggttgcaa aaattttga acgtgcaaaa aaattacca ataatccaga    4500 aaattattat catggattct aaaacggatt accagggatt tcagtcgatg tacacgttcg    4560
tcacatctca tctacctccc ggttttaatg aatacgattt tgtaccagag tcctttgatc    4620
gtgacaaaac aattgcactg ataatgaact cctctggatc tactgggtta cctaagggtg    4680
tggcccttcc gcatagaact gcctgcgtca gattctcgca tgccagagat cctatttttg    4740
gcaatcaaat cattccggat actgcgattt taagtgttgt tccattccat cacggttttg    4800
gaatgtttac tacactcgga tatttgatat gtggatttcg agtcgtctta atgtatagat    4860
```

```
ttgaagaaga gctgttttta cgatcccttc aggattacaa aattcaaagt gcgttgctag    4920
taccaaccct attttcattc ttcgccaaaa gcactctgat tgacaaatac gatttatcta    4980
atttacacga aattgcttct gggggcgcac ctctttcgaa agaagtcggg gaagcggttg    5040
caaaacgctt ccatcttcca gggatacgac aaggatatgg gctcactgag actacatcag    5100
ctattctgat tacacccgag ggggatgata aaccgggcgc ggtcggtaaa gttgttccat    5160
tttttgaagc gaaggttgtg gatctggata ccgggaaaac gctgggcgtt aatcagagag    5220
gcgaattatg tgtcagagga cctatgatta tgtccggtta tgtaaacaat ccggaagcga    5280
ccaacgcctt gattgacaag gatggatggc tacattctgg agacatagct tactgggacg    5340
aagacgaaca cttcttcata gttgaccgct tgaagtcttt aattaaatac aaaggatacc    5400
aggtggcccc cgctgaattg gagtcgatat tgttacaaca ccccaacatc ttcgacgcgg    5460
gcgtggcagg tcttcccgac gatgacgccg gtgaacttcc cgccgccgtt gttgttttgg    5520
agcacggaaa gacgatgacg gaaaaagaga tcgtggatta cgtcgccagt caagtaacaa    5580
ccgcgaaaaa gttgcgcgga ggagttgtgt tgtggacga agtaccgaaa ggtcttaccg    5640
gaaaactcga cgcaagaaaa atcagagaga tcctcataaa ggccaagaag ggcggaaagt    5700
ccaaattgta aatgccgaat tccccgatc gttcaaacat ttggcaataa agtttcttaa    5760
gattgaatcc tgttgccggt cttgcgatga ttatcatata atttctgttg aattacgtta    5820
agcatgtaat aattaacatg taatgcatga cgttatttat gagatgggtt tttatgatta    5880
gagtcccgca attatacatt taatacgcga tagaaaacaa aatatagcgc gcaaactagg    5940
ataaattatc gcgcgcggtg tcatctatgt tactagatcg ctcga                    5985

<210> SEQ ID NO 16
<211> LENGTH: 6135
<212> TYPE: DNA
<213> ORGANISM: Artificial
<220> FEATURE:
<223> OTHER INFORMATION: pZmUbi-Axmi100(opt+3pA)-LUC-nosTerm

<400> SEQUENCE: 16
ctagagataa tgagcattgc atgtctaagt tataaaaaat taccacatat ttttttttgtc      60 acacttgttt gaagtgcagt ttatctatct ttatacatat atttaaactt tactctacga    120
ataatataat ctatagtact acaataatat cagtgtttta gagaatcata taaatgaaca    180
gttagacatg gtctaaagga caattgagta ttttgacaac aggactctac agttttatct    240
ttttagtgtg catgtgttct cctttttttt tttgcaaata gcttcaccta tataatactt    300
catccatttt attagtacat ccatttaggg tttagggtta atggttttta tagactaatt    360
tttttagtac atctatttta ttctatttta gcctctaaat taagaaaact aaaactctat    420
tttagttttt ttatttaata atttagatat aaaatagaat aaaataaagt gactaaaaat    480
taaacaaata ccctttaaga aattaaaaaa actaaggaaa catttttctt gtttcgagta    540
gataatgcca gcctgttaaa cgccgtcgac gcagtctaac ggacaccaac cagcgaacca    600
gcagcgtcgc gtcgggccaa gcgaagcaga cggcacggca tctctgtcgc tgcctctgga    660
cccctctcga gagttccgct ccaccgttgg acttcgtccg ctgtcggcat ccagaaattg    720
cgtggcggag cggcagacgt gagccggcac ggcaggcggc ctcctcctcc tctcacggca    780
ccggcagcta cggggggattc ctttcccacc gctccttcgc tttcccttcc tcgcccgccg    840 taataaaatag acccccctc cacaccctct ttccccaacc tcgtgttgtt cggagcgcac    900
acacacacaa ccagatctcc cccaaatcca cccgtcggca cctccgcttc aaggtacgcc    960
```

```
gctcgtcctc cccccccctc tctaccttct ctagatcggc gttccggtcc atggttaggg      1020
cccggtagtt ctacttctgt tcatgtttgt gttagatccg tgtttgtgtt agatccgtgc      1080
tgctagcgtt cgtacacgga tgcgacctgt acgtcagaca cgttctgatt gctaacttgc      1140
cagtgtttct ctttggggaa tcctgggatg gctctagccg ttccgcagac gggatcgatt      1200
tcatgatttt ttttgtttcg ttgcataggg tttggtttgc ccttttcctt tatttcaata      1260
tatgccgtgc acttgtttgt cgggtcatct tttcatgctt tttttgtct tggttgtgat       1320 gatgtggtct ggttgggcgg tcgttctaga tcggagtaga attctgtttc aaactacctg      1380
gtggatttat taattttgga tctgtatgtg tgtgccatac atattcatag ttacgaattg      1440
aagatgatgg atggaaatat cgatctagga taggtataca tgttgatgcg ggttttactg      1500
atgcatatac agagatgctt ttgttcgctt ggttgtgatg atgtggtgtg gttgggcggt      1560
cgttcattcg ttctagatcg gagtagaata ctgtttcaaa ctacctggtg tatttattaa      1620
ttttggaact gtatgtgtgt gtcatacatc ttcatagtta cgagtttaag atggatggaa      1680
atatcgatct aggataggta tacatgttga tgtgggtttt actgatgcat atacatgatg      1740
gcatatgcag catctattca tatgctctaa ccttgagtac ctatctatta taataaacaa      1800
gtatgtttta taattatttt gatcttgata tacttggatg atggcatatg cagcagctat      1860
atgtggattt ttttagccct gccttcatac gctatttatt tgcttggtac tgtttctttt      1920
gtcgatgctc accctgttgt ttggtgttac ttctgcaggt cgactctagt ggatccatga      1980
acaggaacaa tcaaaatgaa tgtgagatca ttgatgctcc tcattgtggc tgcccttctg      2040
atgatgtggt gaaatatcct cttgcttcag atccaaatgc tgctctccag aacatgaact      2100
acaaggacta cctccaaaca tatgatggag actacaccga cagcttgatc aaccccaacc      2160
tctccatcaa cacaagagat gtgctgcaaa ctggcatcac cattgttgga aggatcttgg      2220
gcttcctcgg cgtcccccttc gccggccagc tggtgacctt ctacaccttc ctcctcaacc      2280
agctatggcc aacaaatgac aatgctgttt gggaggcctt catggagcag attgaaggca      2340
tcattgctca aggatctcc gagcaagtgg tgagaaatgc tctggatgct ctcaccggca      2400
tccatgacta ctacgaggag tacctcgccg cgctggaaga atggctggag aggccatcag      2460
gagcaagggc caacctcgcc ttccaaagat tgagaacct ccaccagctg ttcgtgagcc       2520
agatgccctc cttcggcagc ggccctggat cagaaagaga tgctgtggcg ctgctcaccg      2580
tctatgctca agctgccaac ctccatctgc tgctgctgaa ggatgctgag atttatggag      2640
ctagatgggg cctccagcaa ggccagatca acctctactt caatgctcag caggacagga      2700
caaggatcta caccaaccac tgcgtcgcca cctacaacag aggccttgga gatctccgcg      2760
gcaccaacac tgaatcatgg ctgaactacc accagttcag aagggagatg accttgatgg      2820
ccatggatct ggtggcgctg ttcccctact acaacctccg ccaatatcca aatggagcta      2880
atcctcagct gacaagagat gtctacacag atcccatcgt gttcaaccct tctgcaaatg      2940
ttggcctctg ccggagatgg ggcaacaacc cctacaacac cttctcagag ctggagaatg      3000
ccttcatcag gccgccgcac ttcttcgacc gcctcaacag cctcaccatc agcaggaaca      3060
gatttgatgt tggaagcaac ttcatcgagc catggagcgg ccacaccttg aggaggagct      3120
tcctcaacac ctctgctgtt caagaagatt catatggcca gatcaccaat caaaggacca      3180
ccatcaacct tccagcaaat ggaactggaa gagttgaaag caccgccgtg gacttcgat     3240 ctgctctggt gggcatctat ggagtgaaca gagcttcctt catccccggc ggcgtgttca      3300
```

```
atggcaccac ccagccaagc accggcggct gccgagatct ctatgattct tcagatgagc    3360
tgccgccaga agaaagcagc ggcacccttcg agcaccgcct cagccatgtc accttcttga    3420
gcttcaccac caaccaagct ggaagcattg caaatgctgg aagggtgcca acatatgttt    3480
ggacccacag agatgttgat ctaaacaaca ccatcaccgc cgacaggatc acccatcttc    3540
ctctcatcaa gagcaatgtt caaagaagtg gccgcgccgt caaggggcca ggcttcactg    3600
gaggagatgt gctgaggatg agctcctcag atgctgacat ctccatcatc ggcatcaccg    3660
ccggcgctcc tctcacccag cagtacagga tcaggctgcg ctatgcaagc aatgttgatg    3720
tcaccatcag gctggtgagg caggacaccc aaagcaacat tggaagcatc aacctcctcc    3780
gcaccatgaa ctcaggagaa gaaagcagat atgaaagcta caggacggtg agatgccag    3840
gaaacttcag aatgacaagc agctcggcgc agatccgcct cttcacccaa ggcctccgcg    3900
tcaatggaga gctgttcctg gacagcttgg agttcatccc cgtcaaccca acaagagaag    3960
cagaagaaga tctggaggcc gccaagaagg ccgtcaccag cctcttcacc aggggattga    4020
tggaagacgc caaaaacata agaaaggcc cggcgccatt ctatccgcta gaggatggaa    4080
ccgctggaga gcaactgcat aaggctatga agagatacgc cctggttcct ggaacaattg    4140
cttttacaga tgcacatatc gaggtgaaca ttacgtaagt ttctgcttct acctttgata    4200
tatatataat aattatcatt aattagtagt aatataatat ttcaaatatt tttttcaaaa    4260
taaaagaatg tagtatatag caattgcttt tctgtagttt ataagtgtgt atattttaat    4320
ttataacttt tctaatatat gaccaaaatt tgttgatgtg caggtacgcg aatacttcg    4380
aaatgtccgt tcggttggca gaagctatga acgatatgg gctgaataca atcacagaa    4440
tcgtcgtatg cagtgaaaac tctcttcaat tctttatgcc ggtgttgggc gcgttattta    4500
tcggagttgc agttgcgccc gcgaacgaca tttataatga acgtgaattg ctcaacagta    4560
tgaacatttc gcagcctacc gtagtgtttg tttccaaaaa ggggttgcaa aaattttga    4620
acgtgcaaaa aaattacca ataatccaga aaattattat catggattct aaaacggatt    4680
accagggatt tcagtcgatg tacacgttcg tcacatctca tctacctccc ggttttaatg    4740
aatacgattt tgtaccagag tcctttgatc gtgacaaaac aattgcactg ataatgaact    4800
cctctggatc tactgggtta cctaagggtg tggcccttcc gcatagaact gcctgcgtca    4860
gattctcgca tgccagagat cctattttg gcaatcaaat cattccggat actgcgattt    4920
taagtgttgt tccattccat cacggttttg gaatgtttac tacactcgga tatttgatat    4980
gtggatttcg agtcgtctta atgtatagat ttgaagaaga ctgttttta cgatcccttc    5040
aggattacaa aattcaaagt gcgttgctag taccaacct attttcattc ttcgccaaaa    5100
gcactctgat tgacaaatac gatttatcta atttacacga aattgcttct ggggcgcac    5160
ctctttcgaa agaagtcggg gaagcggttg caaaacgctt ccatcttcca gggatacgac    5220
aaggatatgg gctcactgag actacatcag ctattctgat tacacccgag ggggatgata    5280
aaccgggcgc ggtcggtaaa gttgttccat tttttgaagc gaaggttgtg gatctggata    5340
ccgggaaaac gctgggcgtt aatcagagag gcgaattatg tgtcagagga cctatgatta    5400
tgtccggtta tgtaaacaat ccggaagcga ccaacgcctt gattgacaag gatggatggc    5460
tacattctgg agacatagct tactgggacg aagacgaaca cttcttcata gttgaccgct    5520
tgaagtcttt aattaaatac aaaggatacc aggtggcccc cgctgaattg gagtcgatat    5580
tgttacaaca ccccaacatc ttcgacgcgg gcgtggcagg tcttcccgac gatgacgccg    5640
gtgaacttcc cgccgccgtt gttgttttgg agcacggaaa gacgatgacg gaaaaagaga    5700
```

```
tcgtggatta cgtcgccagt caagtaacaa ccgcgaaaaa gttgcgcgga ggagttgtgt      5760
ttgtggacga agtaccgaaa ggtcttaccg gaaaactcga cgcaagaaaa atcagagaga      5820
tcctcataaa ggccaagaag ggcggaaagt ccaaattgta aatgccgaat ttccccgatc      5880
gttcaaacat ttggcaataa agtttcttaa gattgaatcc tgttgccggt cttgcgatga      5940
ttatcatata atttctgttg aattacgtta agcatgtaat aattaacatg taatgcatga      6000
cgttatttat gagatggggtt tttatgatta gagtcccgca attatacatt taatacgcga     6060
tagaaaacaa aatatagcgc gcaaactagg ataaattatc gcgcgcggtg tcatctatgt      6120
tactagatcg ctcga                                                      6135

<210> SEQ ID NO 17
<211> LENGTH: 1956
<212> TYPE: DNA
<213> ORGANISM: Artificial
<220> FEATURE:
<223> OTHER INFORMATION: Axmi028 h(WT)m

<400> SEQUENCE: 17
atggcacatc accaccacca tcacggatcc accatgaatc aaaaaaacta tgaaattata       60
ggtgcttcaa caaacggcac aattgaatta cctgaagatt acaacactat agtcagcccc      120
tatgatgctc cagcatccgt tactacaact attgaaatta ctggaaccat actaagcgat      180
ttaggtgttc caggagcatc atcagttagt ttacttttga ataaacttat aaatctatta      240
tggccaaatg ataccaatac tgtgtggggg acattcggaa agaaaccgc tgatcttcta      300 aatgaagtgt tatctccaga tgatccagta gtaaaagatg caaataccat tttaaaagga      360
ataaacggat cccttaactt atatttaaat gcacttgaaa tatggaaaaa agaccccaac      420
aacttaacta ccatagagaa tgtcacagat tactttcgta gtttgaatgt ggtttttaca      480
catgatatgc cttcatttgc tgtacctgga tatgaaacga agttattaac aatttatgca      540
caagctgcaa atcttcattt actttttatta agagatgctt ctaggtttgg agaaggttgg      600
ggactgactc aagaaatcat aaatactaac tataatgatc aattacgatt gacagcagaa      660
tacacggacc attgtgtaaa gtggtacaac gcaggattag aaaaattaaa agggaattta      720
actggggaaa attggtatac ttataatagat tttcgtagag aaatgacgtt aatggtgtta      780
gacgtagttg cattatttcc aaactacgat acacgaatgt acccgatcgg aacgtcatca      840
gaacttacaa gaatgatcta tacagatcca attgcttata cacaaagcga tccatggtac      900
aagataacat ctctttcttt ttcaaatatt gaaaacagtg cgattccaag tccttctttc      960
ttcaggtggc taaaatccgt ttcaattaat agccagtggt ggggcagtgg tcctagtcaa     1020
acctactatt gggttggaca tgaattggta tattctaatt caaattctaa tcaatcactt     1080
aaagttaaat atggagaccc taattctttt attgagcccc ctgattcttt cagttttttct    1140 tctacggatg tttacagaac aatatctgtt gttagaaatt cagtaagtaa ttatatagta     1200
agtgaagttc gattcaattc aattagtagt acaaatcaaa ttagtgaaga aatttataaa     1260
catcaatcaa attggagtag acaagaaacc aaagattcaa ttacagaact atccttagct    1320
gctaatcccc caacaacatt tggaaatgta gcagaataca gtcatagatt agcatatatt     1380
tcagaggcat accaaagtca caacccatca aaataccca cctacattcc tgtattcggt      1440
tggacgcata caagcgtacg ttacgataat aaaatcttcc cggacaaaat cactcaaatt     1500
ccagctgtta aaagctcctc agcccaaggt ggatcatgga aaaatatagt gaaaggcccc     1560
```

-continued

| | |
|---|---|
| gggtttactg gaggagatgt gacaactgca gtttcgccag caactgtaac cgacataata | 1620 |
| aaaatacaag ttactctaga tccaaattca ctttcacaaa aatatcgtgc acgacttcgc | 1680 |
| tatgcttcca atgcatttgt accagctaca ttgtatacaa atacaagtag taattataat | 1740 |
| tttgaactta aaaaaggtac aactgaacag tttacaacat ataattcata ccagtatgta | 1800 |
| gatatcccag gttcaataca atttaataat acttctgata cagtctctgt ttatttgcat | 1860 |
| atggattcaa catctaatgt aaacgttcat gtagatagaa ttgaattcat tccaatagat | 1920 |
| gagcagaagc tgatctccga agaggacctc taatga | 1956 |

<210> SEQ ID NO 18
<211> LENGTH: 1956
<212> TYPE: DNA
<213> ORGANISM: Artificial
<220> FEATURE:
<223> OTHER INFORMATION: Axmi028 h(opt)m

<400> SEQUENCE: 18

| | |
|---|---|
| atggcacatc accaccacca tcacggatcc accatgaacc agaagaacta cgagatcatc | 60 |
| ggcgcgtcca ccaacgggac gatcgagctg cccgaggatt acaacacgat cgtcagcccg | 120 |
| tacgacgcgc ctgcatcagt gacaaccacc atcgagatca cggggacaat cctgtctgac | 180 |
| ctcggtgtgc ctggagcaag ttcagtcagc cttctgctca acaagctgat caacctgctc | 240 |
| tggccgaacg acaccaacac cgtgtggggt acgttcggca aggagacggc cgatctcctc | 300 |
| aacgaggtcc tgtcacctga tgacccagtt gtcaaggacg ctaatacgat cctcaagggg | 360 |
| atcaacgggt cgctgaacct ctacctgaac gccctcgaga tctggaagaa ggaccccgaac | 420 |
| aacctgacta ctatcgagaa cgtgactgac tacttccggt cactcaacgt cgtgttcacg | 480 |
| cacgacatgc cctcgttcgc cgtccctgga tacgagacca agctgctcac catctacgcc | 540 |
| caggctgcaa acctccatct gctgttgctc agggacgcat acgtttcgg tgagggatgg | 600 |
| ggtttgaccc aggagatcat caacacgaac tacaacgacc agctccgcct caccgccgaa | 660 |
| tacaccgacc actgcgtgaa gtggtacaac gccggcttgg agaagctgaa gggcaacctc | 720 |
| acgggtgaga ctggtacac gtacaaccgg ttccgcaggg agatgaccct catggtgctg | 780 |
| gacgtggtcg cattgttccc aaactacgac acccgcatgt acccgatcgg acatcaagc | 840 |
| gagcttaccc gtatgatcta cactgacccc atcgcctaca cccagtccga cccatggtac | 900 |
| aagatcacgt ccctgagctt ctcgaacatc gagaacagcg cgatcccctc ccatcgttc | 960 |
| ttccgctggc tcaagtccgt cagcattaac tcccagtggt ggggttccgg accttcacaa | 1020 |
| acctactact gggtggggca cgaactggtc tacagcaaca gcaacagcaa ccagtcgctg | 1080 |
| aaggtgaagt acggcgaccc taacagcttc atcgagcccc cggattcctt ctccttcagc | 1140 |
| agcacggacg tgtacaggac catctcagtc gtgcgtaatt ccgtgtcgaa ctacatcgtg | 1200 |
| tcggaggtgc ggttcaacag catctcctcc accaaccaga tcagcgagga aatctacaag | 1260 |
| caccagtcta actggagccg gcaggagaca aaggactcaa tcaccgagct gagcctggcc | 1320 |
| gccaaccccg caaccacgtt cggaaacgtt gccgagtaca gtcaccgcct ggcttacatc | 1380 |
| tcagaggcgt accagtctca aacccatct aagtacccga cctatatccc cgtgttcggg | 1440 |
| tggacccaca catccgtgag gtacgacaac aagatttttcc cggacaagat cacgcagatc | 1500 |
| cccgcggtta agagtagctc agctcagggg ggaagctgga agaatatcgt caaggggccc | 1560 |
| ggattcacgg gtgagacgt gacgacgcg gtttcacctg caactgttac ggatattatc | 1620 |
| aagatccagg ttaccttga tcccaacagt ctgagccaga agtatcgggc acgccttcgc | 1680 |

```
tacgccagca acgccttcgt cccggcaacc ctttatacga acacctcgtc aaactacaac    1740
ttcgaactga agaagggcac gactgagcag ttcacgacct acaacagcta ccagtacgtg    1800
gacatccccg gcagcatcca gttcaacaat acgtccgaca ccgtgtcggt ctacctgcac    1860
atggactcaa cctcgaacgt gaacgtgcac gtggaccgga tcgagttcat cccgatcgac    1920
gagcagaagc tgatctccga agaggacctc taatga                              1956
```

<210> SEQ ID NO 19
<211> LENGTH: 1956
<212> TYPE: DNA
<213> ORGANISM: Artificial
<220> FEATURE:
<223> OTHER INFORMATION: Axmi028 h(opt+pA)m

<400> SEQUENCE: 19

```
atggcacatc accaccacca tcacggatcc accatgaatc aaaagaacta tgaaatcatc    60
ggcgcgtcca ccaacgggac gatcgagctg cccgaggatt acaacacgat cgtcagcccg    120
tacgacgcgc ctgcatcagt gacaaccacc atcgagatca cggggacaat actatctgac    180
ctcggtgtgc ctggagcaag ttcagtcagc cttctgctca ataaactgat caacctgctc    240
tggccgaacg acaccaacac cgtgtggggt acgttcggca aggagacggc cgatctcctc    300
aacgaggtcc tgtcacctga tgacccagtt gtcaaggacg ctaatacgat cctcaaggga    360
ataaacgggt cgctgaacct ctacctgaac gccctcgaga tctggaagaa ggacccgaac    420
aacctgacta ctatcgagaa cgtgactgac tacttccggt cactcaacgt cgtgttcacg    480
cacgacatgc cctcgttcgc cgtccctgga tatgaaacca agctgctcac catctacgcc    540
caggctgcaa acctccatct gctgttgctc agggacgcat cacgtttcgg tgagggatgg    600
ggtttgaccc aggagatcat aaatactaac tacaacgacc agctccgcct caccgccgaa    660
tacaccgacc actgcgtgaa gtggtacaac gccggcttgg agaaattaaa gggcaacctc    720
acgggtgaga actggtacac gtacaaccgg ttccgcaggg agatgaccct catggtgctg    780
gacgtggtcg cattgttccc aaactacgac cccgcatgt acccgatcgg acatcaagc    840 gagcttaccc gtatgatcta cactgacccc atcgcctaca cccagtccga cccatggtac    900
aagatcacgt ccctgagctt ctcgaacatc gagaacagcg cgatcccctc cccatcgttc    960
ttccgctggc tcaagtccgt ctcaattaat cccagtggtc ggggttccgg accttcacaa    1020
acctactact gggtggggca cgaactggtc tacagcaaca gcaacagcaa tcaatcgctg    1080
aaggtgaagt acgcgacccc taacagcttc atcgagcccc cggattcctt ctccttcagc    1140
agcacggacg tgtacaggac catctcagtc gtgcgtaatt ccgtgtcgaa ctacatcgtg    1200
tcggaggtgc ggttcaacag catctcctcc accaatcaaa tcagcgagga aatctacaag    1260
caccaatcaa actggagccg gcaggaaacc aaggactcaa tcaccgagct gagcctggcc    1320
gccaacccgc caaccacgtt cggaaacgtt gccgaataca gtcaccgcct ggcttacatc    1380
tcagaggcgt accagtctca caacccatca aaatacccga cctatatccc cgtgttcggg    1440
tggacccaca catccgtgag gtacgacaat aaaatttttcc cggacaagat cacgcagatc    1500
cccgcggtta agagtagctc agctcagggg ggaagctgga aaaatatcgt caagggggccc    1560 ggattcacgg gtggagacgt gacgacggcg gtttcacctg caactgttac ggatataata    1620
aaaatacagg ttaccccttga tcccaacagt ctgagccaaa aatatcgggc acgccttcgc    1680
tacgccagca acgccttcgt cccggcaacc ctttatacga atacatcgtc aaactacaac    1740
```

```
ttcgaactga agaagggcac gactgagcag ttcacgacat ataacagcta ccagtacgtg      1800
gacatccccg gctcaataca gttcaataat acgtccgaca ccgtgtcggt ctacctgcac      1860
atggactcaa cctcgaacgt gaacgtgcac gtggaccgga tcgagttcat cccgatcgac      1920
gagcagaagc tgatctccga agaggacctc taatga                                1956

<210> SEQ ID NO 20
<211> LENGTH: 2106
<212> TYPE: DNA
<213> ORGANISM: Artificial
<220> FEATURE:
<223> OTHER INFORMATION: Axmi100 h(WT)m

<400> SEQUENCE: 20
atggcacatc accaccacca tcacggatcc accatgaatc gaataatca aaatgaatgt         60 gaaattattg atgcccctca ttgtggatgt ccgtcagatg atgttgtgaa atatcctttg       120
gcaagtgacc caaatgcagc gttacaaaat atgaactata agattatttt acaaacgtat       180
gatggagact atacagattc tcttattaat cctaacttat ctattaatac tagggatgta       240
ctacaaacag gtattactat tgtgggaaga atactagggt ttttaggtgt tccatttgcg       300
gggcaactag ttactttcta tacctttctc ttaaatcagt tatggccaac taatgataat       360
gcagtatggg aagcttttat ggaacaaata gaagggatta cgctcaaag aatatcggag       420 caagtagtaa ggaatgcgct tgatgcctta actggaatac acgattatta tgaggaatat       480
ttagcggcat tagaggagtg gctggaaaga ccgagcggcg caagggctaa cttagcttt       540 cagaggtttg aaaatctaca tcaattattt gtaagtcaga tgccaagttt tggtagtggt       600
cctggtagtg aaagagatgc ggtagcattg ctgacagtat atgcacaagc agcgaatctc       660
catttgttgt tattaaaaga tgcagaaatt tatggggcga gatggggact tcaacaaggc       720
caaattaatt tatattttaa tgctcaacaa gatcgcactc gaatttatac caatcattgt       780
gtggcaacat ataatagagg attaggagac ttaagaggca caaatactga agttggtta        840 aattaccatc aattccgtag agagatgaca ttaatggcaa tggatttagt ggcattattc       900
ccatactata atttacgaca atatccaaac ggggcaaacc ctcagcttac acgtgatgta       960
tatacagatc cgattgtatt taatccatca gctaatgtag gattatgtag acgttgggc       1020 aataacccat ataatacatt ttcggaactt gaaaatgcct tcattcgccc gccacatttt       1080
tttgataggt tgaatagttt aacaattagt agaaatagat ttgacgttgg atcaaacttt       1140
atagagcctt ggtctggaca tacgttacgc cgtagttttc tgaacacttc ggcagtacaa       1200
gaagatagtt atggccaaat tactaatcaa agaacaacaa ttaatctacc agctaatgga       1260
actgggcgag tggagtcaac agcagtagat tttcgtagcg cgcttgtggg gatatacggc       1320
gttaatagag cttctttat tcccggtggt gtgtttaatg gcacgactca accttctact       1380
ggaggatgta gagatttgta tgattcaagt gatgaattac caccagaaga agtagtggaa       1440
acgtttgaac ataggttatc tcatgttacc tttttaagtt ttacaactaa tcaggctgga       1500
tccatagcca atgcagggcg cgtccctact tatgtctgga cccatcgaga tgtggacctt       1560
aataacacga ttactgcaga tagaattaca cacttaccat tgataaaatc aaatgtgcaa       1620
cgcagtggtc gcgcagtaaa aggaccagga tttacaggag gagatgtact ccgaatgtca       1680
tcaagtgatg ctgatatatc aataatagga ataacggcag gtgcaccgct aacacaacaa       1740
tatcgtataa gattgcgtta tgcttcaaat gtagatgtta ctatccgttt agtgagacag       1800
gacacccaaa gtaatatagg aagcataaac ttattacgta caatgaacag tggagaggag       1860
```

```
tcaaggtatg aatcatatcg tactgtagag atgcctggta attttagaat gactagtagt    1920
tcagcacaga ttcgactatt tactcaagga cttcgagtga atggagaatt gtttcttgat    1980
agtcttgaat ttatcccagt taatccgaca cgtgaggcgg aagaggattt agaagcagcg    2040
aagaaagcgg tgacgagctt gtttacacgt gagcagaagc tgatctccga agaggacctc    2100
taatga                                                               2106

<210> SEQ ID NO 21
<211> LENGTH: 2106
<212> TYPE: DNA
<213> ORGANISM: Artificial
<220> FEATURE:
<223> OTHER INFORMATION: Axmi100 h(opt)m

<400> SEQUENCE: 21
atggcacatc accaccacca tcacggatcc accatgaaca ggaacaacca aaatgaatgt      60
gagatcattg atgctcctca ttgtggctgc ccttctgatg atgtggtgaa atatcctctt     120
gcttcagatc caaatgctgc tctccagaac atgaactaca aggactacct ccaaacatat     180
gatggagact acaccgacag cttgatcaac cccaacctct ccatcaacac aagagatgtg     240
ctgcaaactg gcatcaccat tgttggaagg atcttgggct tcctcggcgt ccccttcgcc     300
ggccagctgg tgaccttcta caccttcctc ctcaaccagc tatggccaac aaatgacaat     360
gctgttgggg aggccttcat ggagcagatt gaaggcatca ttgctcaaag gatctccgag     420
caagtggtga aaatgctct ggatgctctc accggcatcc atgactacta cgaggagtac      480
ctcgccgcgc tggaagaatg gctggagagg ccatcaggag caagggccaa cctcgccttc     540
caaagatttg agaacctcca ccagctgttc gtgagccaga tgccctcctt cggcagcggc     600
cctggatcag aaagagatgc tgtggcgctg ctcaccgtct atgctcaagc tgccaacctc     660
catctgctgc tgctgaagga tgctgagatt tatggagcta gatggggcct ccagcaaggc     720
cagatcaacc tctacttcaa tgctcagcag gacaggacaa ggatctacac caaccactgc     780
gtcgccacct acaacagagg ccttggagat ctccgcggca ccaacactga atcatggctg     840
aactaccacc agttcagaag ggagatgacc ttgatggcca tggatctggt ggcgctgttc     900
ccctactaca acctccgcca atatccaaat ggagctaatc tcagctgac aagagatgtc      960 tacacagatc ccatcgtgtt caaccttct gcaaatgttg gctctgccg agatggggc      1020 aacaaccct acaacacctt ctcagagctg gagaatgcct tcatcaggcc gccgcacttc    1080
ttcgaccgcc tcaacagcct caccatcagc aggaacagat ttgatgttgg aagcaacttc    1140
atcgagccat ggagcggcca caccttgagg aggagcttcc tcaacacctc tgctgttcaa    1200
gaagattcat atggccagat caccaaccag aggaccacca tcaaccttcc agcaaatgga    1260
actggaagag ttgaaagcac cgccgtggac ttcagatctg ctctggtggg catctatgga    1320
gtgaacagag cttccttcat ccccggcggc gtgttcaatg caccaccca gccaagcacc    1380 ggcggctgcc gagatctcta tgattcttca gatgagctgc cgccagaaga aagcagcggc    1440
accttcgagc accgcctcag ccatgtcacc ttcttgagct tcaccaccaa ccaagctgga    1500
agcattgcaa atgctggaag ggtgccaaca tatgtttgga cccacagaga tgttgatcta    1560
aacaacacca tcaccgccga caggatcacc catcttcctc tcatcaagag caatgttcaa    1620
agaagtggcc gcgccgtcaa ggggccaggc ttcactggag gagatgtgct gaggatgagc    1680
tcctcagatg ctgacatctc catcatcggc atcaccgccg gcgctcctct cacccagcag    1740
```

| | |
|---|---:|
| tacaggatca ggctgcgcta tgcaagcaat gttgatgtca ccatcaggct ggtgaggcag | 1800 |
| gacacccaaa gcaacattgg aagcatcaac ctcctccgca ccatgaactc aggagaagaa | 1860 |
| agcagatatg aaagctacag gacggtggag atgccaggaa acttcagaat gacaagcagc | 1920 |
| tcggcgcaga tccgcctctt cacccaaggc ctccgcgtca atggagagct gttcctggac | 1980 |
| agcttggagt tcatccccgt caacccaaca agagaagcag aagaagatct ggaggccgcc | 2040 |
| aagaaggccg tcaccagcct cttcaccagg gagcagaagc tgatctccga agaggacctc | 2100 |
| taatga | 2106 |

<210> SEQ ID NO 22
<211> LENGTH: 2106
<212> TYPE: DNA
<213> ORGANISM: Artificial
<220> FEATURE:
<223> OTHER INFORMATION: Axmi100 h(opt+pA)m

<400> SEQUENCE: 22

| | |
|---|---:|
| atggcacatc accaccacca tcacggatcc accatgaaca ggaataatca aaatgaatgt | 60 |
| gagatcattg atgctcctca ttgtggctgc ccttctgatg atgtggtgaa atatcctctt | 120 |
| gcttcagatc caaatgctgc tctccaaaat atgaactaca ggactaccct ccaaacatat | 180 |
| gatggagact acaccgacag cttgattaat cccaacctct ccattaatac tagagatgtg | 240 |
| ctgcaaactg gcatcaccat tgttggaagg atactaggct cctcggcgt cccttcgcc | 300 |
| ggccagctgg tgaccttcta cacccttcctc ctcaaccagc tatggccaac aaatgacaat | 360 |
| gctgtttggg aggccttcat ggagcagatt gaaggcatca ttgctcaaag gatctccgag | 420 |
| caagtggtga aaatgctct ggatgctctc accggaatac atgactacta cgaggagtac | 480 |
| ctcgccgcgc tggaagaatg gctggagagg ccatcaggag caagggccaa cctcgccttc | 540 |
| caaagatttg agaacctcca ccagctgttc gtgagccaga tgccctcctt cggcagcggc | 600 |
| cctggatcag aaagagatgc tgtggcgctg ctcaccgtct atgctcaagc tgccaacctc | 660 |
| catctgctgc tattaaagga tgctgagatt tatggagcta gatggggcct ccagcaaggc | 720 |
| caaattaatc tctacttcaa tgctcagcag gacaggacaa ggatctacac caaccactgc | 780 |
| gtcgccacat ataacagagg ccttggagat ctccgcggca ccaacactga atcatggctg | 840 |
| aactaccacc agttcagaag ggagatgaca ttaatggcca tggatctggt ggcgctgttc | 900 |
| ccatactaca acctccgcca atatccaaat ggagctaatc ctcagctgac aagagatgtc | 960 |
| tacacagatc ccatcgtgtt caaccctcct gcaaatgttg cctctgccg agatggggc | 1020 |
| aacaacccat ataatacatt ctcagagctg gagaatgcct tcatcaggcc gccgcacttc | 1080 |
| ttcgaccgcc tcaacagcct caccatcagc aggaacagat ttgatgttgg aagcaacttc | 1140 |
| atcgagccat ggagcggcca caccttgagg aggagcttcc tcaacacctc tgctgttcaa | 1200 |
| gaagattcat atggccagat caccaatcaa aggaccacaa ttaatcttcc agcaaatgga | 1260 |
| actggaagag ttgaaagcac cgccgtggac ttcagatctg ctctggtggg catctatgga | 1320 |
| gtgaacagag cttccttcat ccccggcggc gtgttcaatg caccacccca gccaagcacc | 1380 |
| ggcggctgcc gagatctcta tgattcttca gatgagctgc cgccagaaga aagcagcggc | 1440 |
| accttcgagc accgcctcag ccatgtcacc ttcttgagct tcaccaccaa ccaagctgga | 1500 |
| agcattgcaa atgctggaag ggtgccaaca tatgtttgga cccacagaga tgttgatcta | 1560 |
| aacaacacca tcaccgccga caggatcacc catcttcctc tcataaaatc aaatgttcaa | 1620 |
| agaagtggcc gcgccgtcaa ggggccaggc ttcactggag agatgtgct gaggatgagc | 1680 |

-continued

```
tcctcagatg ctgacatctc aataatcggc atcaccgccg gcgctcctct cacccagcag    1740
tacaggatca ggctgcgcta tgcaagcaat gttgatgtca ccatcaggct ggtgaggcag    1800
gacacccaaa gcaacattgg aagcataaac ctcctccgca ccatgaactc aggagaagaa    1860
agcagatatg aaagctacag gacggtggag atgccaggaa acttcagaat gacaagcagc    1920
tcggcgcaga tccgcctctt cacccaaggc ctccgcgtca atggagagct gttcctggac    1980
agcttggagt tcatccccgt caacccaaca agagaagcag aagaagatct ggaggccgcc    2040
aagaaggccg tcaccagcct cttcaccagg gagcagaagc tgatctccga gaggacctc    2100 taatga                                                               2106
```

<210> SEQ ID NO 23
<211> LENGTH: 1956
<212> TYPE: DNA
<213> ORGANISM: Artificial
<220> FEATURE:
<223> OTHER INFORMATION: Axmi028 h(opt+3pA)m

<400> SEQUENCE: 23

```
atggcacatc accaccacca tcacggatcc accatgaacc agaagaacta cgagatcatc      60
ggcgcgtcca ccaacgggac gatcgagctg cccgaggatt acaacacgat cgtcagcccg     120
tacgacgcgc ctgcatcagt gacaaccacc atcgagatca cggggacaat cctgtctgac     180
ctcggtgtgc ctggagcaag ttcagtcagc cttctgctca acaagctgat caacctgctc     240
tggccgaacg acaccaacac cgtgtggggt acgttcggca aggagacggc cgatctcctc     300
aacgaggtcc tgtcacctga tgacccagtt gtcaaggacg ctaatacgat cctcaagggg     360
atcaacgggt cgctgaacct ctacctgaac gccctcgaga tctggaagaa ggacccgaac     420
aacctgacta ctatcgagaa cgtgactgac tacttccggt cactcaacgt cgtgttcacg     480
cacgacatgc cctcgttcgc cgtccctgga tacgagacca agctgctcac catctacgcc     540
caggctgcaa acctccatct gctgttgctc agggacgcat cacgtttcgg tgagggatgg     600
ggtttgaccc aggagatcat caacacgaac tacaacgacc agctccgcct caccgccgaa     660
tacaccgacc actgcgtgaa gtggtacaac gccggcttgg agaagctgaa gggcaacctc     720
acgggtgaga actggtacac gtacaaccgg ttccgcaggg agatgaccct catggtgctg     780
gacgtggtcg cattgttccc aaactacgac cccgcatgt acccgatcgg acatcaagc      840 gagcttaccc gtatgatcta cactgacccc atcgcctaca cccagtccga cccatggtac     900
aagatcacgt ccctgagctt ctcgaacatc gagaacagcg cgatcccctc cccatcgttc     960
ttccgctggc tcaagtccgt cagcattaac tcccagtggt ggggttccgg accttcacaa    1020
acctactact gggtggggca cgaactggtc tacagcaaca gcaacagcaa tcaatcgctg    1080
aaggtgaagt acggcgaccc taacagcttc atcgagcccc ggattccttc tccttcagc    1140 agcacggacg tgtacaggac catctcagtc gtgcgtaatt ccgtgtcgaa ctacatcgtg    1200
tcggaggtgc ggttcaacag catctcctcc accaaccaga tcagcgagga aatctacaag    1260
caccaatcaa actggagccg gcaggagaca aaggactcaa tcaccgagct gagcctggcc    1320
gccaacccgc caaccacgtt cggaaacgtt gccgagtaca gtcaccgcct ggcttacatc    1380
tcagaggcgt accagtctca caacccatct aagtacccga cctatatccc cgtgttcggg    1440
tggacccaca catccgtgag gtacgacaac aagattttcc cggacaagat cacgcagatc    1500
cccgcggtta agagtagctc agctcagggg ggaagctgga agaatatcgt caaggggccc    1560
```

| | |
|---|---|
| ggattcacgg gtggagacgt gacgacggcg gtttcacctg caactgttac ggatattatc | 1620 |
| aagatccagg ttaccttga tcccaacagt ctgagccaga agtatcgggc acgccttcgc | 1680 |
| tacgccagca acgccttcgt cccggcaacc ctttatacga cacctcgtc aaactacaac | 1740 |
| ttcgaactga agaagggcac gactgagcag ttcacgacct acaacagcta ccagtacgtg | 1800 |
| gacatccccg gcagcatcca gttcaacaat acgtccgaca ccgtgtcggt ctacctgcac | 1860 |
| atggactcaa cctcgaacgt gaacgtgcac gtggaccgga tcgagttcat cccgatcgac | 1920 |
| gagcagaagc tgatctccga agaggacctc taatga | 1956 |

<210> SEQ ID NO 24
<211> LENGTH: 2106
<212> TYPE: DNA
<213> ORGANISM: Artificial
<220> FEATURE:
<223> OTHER INFORMATION: Axmi100 h(opt+3pA)m

<400> SEQUENCE: 24

| | |
|---|---|
| atggcacatc accaccacca tcacggatcc accatgaaca ggaacaatca aaatgaatgt | 60 |
| gagatcattg atgctcctca ttgtggctgc ccttctgatg atgtggtgaa atatcctctt | 120 |
| gcttcagatc caaatgctgc tctccagaac atgaactaca aggactacct ccaaacatat | 180 |
| gatggagact acaccgacag cttgatcaac cccaacctct ccatcaacac aagagatgtg | 240 |
| ctgcaaactg gcatcaccat tgttggaagg atcttgggct tcctcggcgt ccccttcgcc | 300 |
| ggccagctgg tgaccttcta caccttcctc ctcaaccagc tatggccaac aaatgacaat | 360 |
| gctgtttggg aggccttcat ggagcagatt gaaggcatca ttgctcaaag gatctccgag | 420 |
| caagtggtga aaatgctct ggatgctctc accggcatcc atgactacta cgaggagtac | 480 |
| ctcgccgcgc tggaagaatg gctggagagg ccatcaggag caagggccaa cctcgccttc | 540 |
| caaagatttg agaacctcca ccagctgttc gtgagccaga tgccctcctt cggcagcggc | 600 |
| cctggatcag aaagagatgc tgtggcgctg ctcaccgtct atgctcaagc tgccaacctc | 660 |
| catctgctgc tgctgaagga tgctgagatt tatggagcta gatgggcct ccagcaaggc | 720 |
| cagatcaacc tctacttcaa tgctcagcag gacaggacaa ggatctacac caaccactgc | 780 |
| gtcgccacct acaacagagg ccttggagat ctccgcggca ccaacactga atcatggctg | 840 |
| aactaccacc agttcagaag ggagatgacc ttgatggcca tggatctggt ggcgctgttc | 900 |
| ccctactaca acctccgcca atatccaaat ggagctaatc ctcagctgac aagagatgtc | 960 |
| tacacagatc ccatcgtgtt caaccccttct gcaaatgttg gcctctgccg agatggggc | 1020 |
| aacaacccct acaacacctt ctcagagctg gagaatgcct catcaggcc gccgcacttc | 1080 |
| ttcgaccgcc tcaacagcct caccatcagc aggaacagat ttgatgttgg aagcaacttc | 1140 |
| atcgagccat ggagcggcca caccttgagg aggagcttcc tcaacacctc tgctgttcaa | 1200 |
| gaagattcat atggccagat caccaatcaa aggaccacca tcaaccttcc agcaaatgga | 1260 |
| actggaagag ttgaaagcac cgccgtgac ttcagatctg ctctggtggg catctatgga | 1320 |
| gtgaacagag cttccttcat ccccggcggc gtgttcaatg caccacccca gccaagcacc | 1380 |
| ggcggctgcc gagatctcta tgattcttca gatgagctgc cgccagaaga aagcagcggc | 1440 |
| accttcgagc accgcctcag ccatgtcacc ttcttgagct tcaccaccaa ccaagctgga | 1500 |
| agcattgcaa atgctggaag ggtgccaaca tatgtttgga cccacagaga tgttgatcta | 1560 |
| aacaaccacca tcaccgccga caggatcacc catcttcctc tcatcaagag caatgttcaa | 1620 |
| agaagtggcc gcgccgtcaa ggggccaggc ttcactggag agatgtgct gaggatgagc | 1680 |

```
tcctcagatg ctgacatctc catcatcggc atcaccgccg gcgctcctct cacccagcag    1740
tacaggatca ggctgcgcta tgcaagcaat gttgatgtca ccatcaggct ggtgaggcag    1800
gacacccaaa gcaacattgg aagcatcaac ctcctccgca ccatgaactc aggagaagaa    1860
agcagatatg aaagctacag gacggtggag atgccaggaa acttcagaat gacaagcagc    1920
tcggcgcaga tccgcctctt cacccaaggc ctccgcgtca atggagagct gttcctggac    1980
agcttggagt tcatccccgt caacccaaca agagaagcag aagaagatct ggaggccgcc    2040
aagaaggccg tcaccagcct cttcaccagg gagcagaagc tgatctccga agaggacctc    2100
taatga                                                                2106
```

<210> SEQ ID NO 25
<211> LENGTH: 20
<212> TYPE: DNA
<213> ORGANISM: Artificial
<220> FEATURE:
<223> OTHER INFORMATION: cMyc_F primer

<400> SEQUENCE: 25
gaagctgatc tccgaagagg                                                 20

<210> SEQ ID NO 26
<211> LENGTH: 20
<212> TYPE: DNA
<213> ORGANISM: Artificial
<220> FEATURE:
<223> OTHER INFORMATION: cMyc_R primer

<400> SEQUENCE: 26
tgaaccaaac gaggaagatg                                                 20

<210> SEQ ID NO 27
<211> LENGTH: 24
<212> TYPE: DNA
<213> ORGANISM: Artificial
<220> FEATURE:
<223> OTHER INFORMATION: His-tag_3_F primer

<400> SEQUENCE: 27
ttggtgtaag ctattttctt tgaa                                            24

<210> SEQ ID NO 28
<211> LENGTH: 20
<212> TYPE: DNA
<213> ORGANISM: Artificial
<220> FEATURE:
<223> OTHER INFORMATION: His-tag_3_R primer

<400> SEQUENCE: 28
gatgtgccat ggtggagata                                                 20

<210> SEQ ID NO 29
<211> LENGTH: 7211
<212> TYPE: DNA
<213> ORGANISM: Artificial
<220> FEATURE:
<223> OTHER INFORMATION: pD35-nH-cM-Axmi028-wt

<400> SEQUENCE: 29
gtgagcgcaa cgcaattaat gtgagttagc tcactcatta ggcacccag gctttacact      60 ttatgcttcc ggctcgtatg ttgtgtggaa ttgtgagcgg ataacaattt cacacaggaa    120

```
acagctatga ccatgattac gccaagctcg aaattaaccc tcactaaagg gaacaaaagc    180
tggagctcac tggatttttgg ttttaggaat tagaaatttt attgatagaa gtattttaca    240
aatacaaata catactaagg gtttcttata tgctcaacac atgagcgaaa ccctataaga    300
accctaattc ccttatctgg gaactactca cacattattc tggagaaaaa tagagagaga    360
tagatttgta gagagagact ggtgattttt gcgggtcccg ctcagaagaa ctcgtcaaga    420
aggcgataga aggcgatgcg ctgcgaatcg ggagcggcga taccgtaaag cacgaggaag    480
cggtcagccc attcgccgcc aagctcttca gcaatatcac gggtagccaa cgctatgtcc    540
tgatagcggt ccgccacacc cagccggcca cagtcgatga atccagaaaa gcggccattt    600
tccaccatga tattcggcaa gcaggcatcg ccatgggtca cgacgagatc ctcgccgtcg    660
ggcatgcgcg ccttgagcct ggcgaacagt tcggctggcg cgagccctg atgctcttcg    720 tccagatcat cctgatcgac aagaccggct tccatccgag tacgtgctcg ctcgatgcga    780
tgtttcgctt ggtggtcgaa tgggcaggta gccggatcaa gcgtatgcag ccgccgcatt    840
gcatcagcca tgatggatac tttctcggca ggagcaaggt gagatgacag gagatcctgc    900
cccggcactt cgcccaatag cagccagtcc cttcccgctt cagtgacaac gtcgagcaca    960
gctgcgcaag gaacgcccgt cgtggccagc cacgatagcc gcgctgcctc gtcctgcagt   1020
tcattcaggg caccggacag gtcggtcttg acaaaaagaa ccgggcgccc ctgcgctgac   1080
agccggaaca cggcggcatc agagcagccg attgtctgtt gtgcccagtc atagccgaat   1140
agcctctcca cccaagcggc cggagaacct gcgtgcaatc catcttgttc aatccaagct   1200
cccatggtgg ccactcgagg tgcagattat ttggattgag agtgaatatg agactctaat   1260
tggataccga ggggaattta tggaacgtca gtggagcatt tttgacaaga aatatttgct   1320
agctgatagt gaccttaggc gacttttgaa cgcgcaataa tggtttctga cgtatgtgct   1380
tagctcatta aactccagaa acccgcggct gagtggctcc ttcaacgttg cggttctgtc   1440
agttccaaac gtaaaacggc ttgtcccgcg tcatcggcgg gggtcataac gtgactccct   1500
taattctccg ctcatgatct agaggccatg gcggccgcta gatcgggcca acatggtgga   1560
gcacgacact ctcgtctact ccaagaatat caaagataca gtctcagaag accaaagggc   1620
tattgagact tttcaacaaa gggtaatatc gggaaacctc ctcggattcc attgcccagc   1680
tatctgtcac ttcatcaaaa ggacagtaga aaggaaggt ggcacctaca aatgccatca   1740
ttgcgataaa ggaaaggcta tcgttcaaga tgcctctgcc gacagtggtc ccaaagatgg   1800 accccccaccc acgaggagca tcgtggaaaa agaagacgtt ccaaccacgt cttcaaagca   1860
agtggattga tgtgaacatg gtggagcacg acactctcgt ctactccaag aatatcaaag   1920
atacagtctc agaagaccaa agggctattg agacttttca acaaagggta atatcgggaa   1980
acctcctcgg attccattgc ccagctatct gtcacttcat caaaaggaca gtagaaaagg   2040
aaggtggcac ctacaaatgc catcattgcg ataaaggaaa ggctatcgtt caagatgcct   2100
ctgccgacag tggtcccaaa gatggacccc caccacgag gagcatcgtg aaaaagaag   2160 accttccaac cacgtcttca agcaagtgg attgatgtga tatctccact gacgtaaggg   2220
atgacgcaca atcccactat ccttcgcaag acccttcctc tatataagga agttcatttc   2280
atttggagag gacacgctga atcaccagt ctctctctac aaatctatct ctctcgacta   2340
gtatgcacca ccaccatcac cacatcgata tgaatcaaaa aaactatgaa attataggtg   2400
cttcaacaaa cggcacaatt gaattacctg aagattacaa cactatagtc agcccctatg   2460
atgctccagc atccgttact acaactattg aaattactgg aaccatacta agcgatttag   2520
```

```
gtgttccagg agcatcatca gttagtttac ttttgaataa acttataaat ctattatggc    2580
caaatgatac caatactgtg tgggggacat tcggaaaaga aaccgctgat cttctaaatg    2640
aagtgttatc tccagatgat ccagtagtaa aagatgcaaa taccatttta aaaggaataa    2700
acggatccct taacttatat ttaaatgcac ttgaaatatg gaaaaaagac cccaacaact    2760
taactaccat agagaatgtc acagattact ttcgtagttt gaatgtggtt tttacacatg    2820
atatgccttc atttgctgta cctggatatg aaacgaagtt attaacaatt tatgcacaag    2880
ctgcaaatct tcatttactt ttattaagag atgcttctag gtttggagaa ggttggggac    2940
tgactcaaga aatcataaat actaactata atgatcaatt acgattgaca gcagaataca    3000
cggaccattg tgtaaagtgg tacaacgcag gattagaaaa attaaaaggg aatttaactg    3060
gggaaaattg gtatacttat aatagatttc gtagagaaat gacgttaatg gtgttagacg    3120
tagttgcatt atttccaaac tacgatacac gaatgtaccc gatcggaacg tcatcagaac    3180
ttacaagaat gatctataca gatccaattg cttatacaca aagcgatcca tggtacaaga    3240
taacatctct ttcttttttca aatattgaaa acagtgcgat tccaagtcct tctttcttca    3300
ggtggctaaa atccgtttca attaatagcc agtggtgggg cagtggtcct agtcaaacct    3360
actattgggt tggacatgaa ttggtatatt ctaattcaaa ttctaatcaa tcacttaaag    3420
ttaaatatgg agaccctaat tcttttattg agccccctga ttcttcagt ttttcttcta    3480 cggatgttta cagaacaata tctgttgtta gaaattcagt aagtaattat atagtaagtg    3540
aagttcgatt caattcaatt agtagtacaa atcaaattag tgaagaaatt tataaacatc    3600
aatcaaattg gagtagacaa gaaaccaaag attcaattac agaactatcc ttagctgcta    3660
atcccccaac aacatttgga aatgtagcag aatacagtca tagattagca tatatttcag    3720
aggcatacca aagtcacaac ccatcaaaat acccaaccta cattcctgta ttcggttgga    3780
cgcatacaag cgtacgttac gataataaaa tcttcccgga caaatcact caaattccag    3840 ctgttaaaag ctcctcagcc caaggtggat catggaaaaa tatagtgaaa ggccccgggt    3900
ttactggagg agatgtgaca actgcagttt cgccagcaac tgtaaccgac ataataaaaa    3960
tacaagttac tctagatcca aattcacttt cacaaaaata tcgtgcacga cttcgctatg    4020
cttccaatgc atttgtacca gctacattgt atacaaatac aagtagtaat tataattttg    4080
aacttaaaaa aggtacaact gaacagttta caacatataa ttcataccag tatgtagata    4140
tcccaggttc aatacaattt aataatactt ctgatacagt ctctgtttat ttgcatatgg    4200
attcaacatc taatgtaaac gttcatgtag atagaattga attcattcca atagatgtaa    4260
agcttacgga gcagaagctg atctccgagg aggacctgta acgtgtcgac cctgctttaa    4320
tgagatatgc gagacgccta tgatcgcatg atatttgctt tcaattctgt tgtgcacgtt    4380
gtaaaaaacc tgagcatgtg tagctcagat ccttaccgcc ggtttcggtt cattctaatg    4440
aatatatcac ccgttactat cgtatttta tgaataatat tctccgttca atttactgat    4500
tgtcctcgac aggccttaag ggccagatct tgggcccggt acccaattcg ccctatagtg    4560
agtcgtatta caattcactg gccgtcgttt tacaacgtcg tgactgggaa accctggcg    4620 ttacccaact taatcgcctt gcagcacatc cccctttcgc cagctggcgt aatagcgaag    4680
aggcccgcac cgatcgccct tcccaacagt tgcgcagcct gaatggcgaa tggaaattgt    4740
aagcgttaat attttgttaa aattcgcgtt aaatttttgt taaatcagct cattttttaa    4800
ccaataggcc gaaatcggca aaatccctta taaatcaaaa gaatagaccg agatagggtt    4860
```

```
gagtgttgtt ccagtttgga acaagagtcc actattaaag aacgtggact ccaacgtcaa    4920
agggcgaaaa accgtctatc agggcgatgg cccactacgt gaaccatcac cctaatcaag    4980
ttttttgggg tcgaggtgcc gtaaagcact aaatcggaac cctaaaggga gcccccgatt    5040
tagagcttga cggggaaagc cggcgaacgt ggcgagaaag gaagggaaga aagcgaaagg    5100
agcgggcgct agggcgctgg caagtgtagc ggtcacgctg cgcgtaacca ccacacccgc    5160
cgcgcttaat gcgccgctac agggcgcgtc aggtggcact tttcggggaa atgtgcgcgg    5220
aaccCctatt tgtttatttt tctaaataca ttcaaatatg tatccgctca tgagacaata    5280
accctgataa atgcttcaat aatattgaaa aaggaagagt atgagtattc aacatttccg    5340
tgtcgccctt attcccttttt tgcggcatt ttgccttcct gtttttgctc acccagaaac    5400
gctggtgaaa gtaaaagatg ctgaagatca gttgggtgca cgagtgggtt acatcgaact    5460
ggatctcaac agcggtaaga tccttgagag ttttcgcccc gaagaacgtt ttccaatgat    5520
gagcactttt aaagttctgc tatgtggcgc ggtattatcc cgtattgacg ccgggcaaga    5580
gcaactcggt cgccgcatac actattctca gaatgacttg gttgagtact caccagtcac    5640
agaaaagcat cttacggatg gcatgacagt aagagaatta tgcagtgctg ccataaccat    5700
gagtgataac actgcggcca acttacttct gacaacgatc ggaggaccga aggagctaac    5760
cgcttttttg cacaacatgg ggatcatgt aactcgcctt gatcgttggg aaccggagct    5820
gaatgaagcc ataccaaacg acgagcgtga caccacgatg cctgtagcaa tggcaacaac    5880
gttgcgcaaa ctattaactg gcgaactact tactctagct tcccggcaac aattaataga    5940
ctggatggag gcggataaag ttgcaggacc acttctgcgc tcggcccttc cggctggctg    6000
gtttattgct gataaatctg gagccggtga gcgtgggtct cgcggtatca ttgcagcact    6060
ggggccagat ggtaagccct cccgtatcgt agttatctac acgacgggga gtcaggcaac    6120
tatggatgaa cgaaatagac agatcgctga gataggtgcc tcactgatta gcattggta    6180
actgtcagac caagtttact catatatact ttagattgat ttaaaacttc attttttaatt    6240
taaaaggatc taggtgaaga tccttttttga taatctcatg accaaaatcc cttaacgtga    6300
gttttcgttc cactgagcgt cagaccccgt agaaaagatc aaaggatctt cttgagatcc    6360
ttttttttctg cgcgtaatct gctgcttgca acaaaaaaa ccaccgctac cagcggtggt    6420
ttgtttgccg gatcaagagc taccaactct ttttccgaag gtaactggct tcagcagagc    6480
gcagatacca atactgtcc ttctagtgta gccgtagtta ggccaccact tcaagaactc    6540
tgtagcaccg cctacatacc tcgctctgct aatcctgtta ccagtggctg ctgccagtgg    6600
cgataagtcg tgtcttaccg ggttggactc aagacgatag ttaccggata aggcgcagcg    6660
gtcgggctga acgggggtt cgtgcacaca gcccagcttg gagcgaacga cctacaccga    6720
actgagatac ctacagcgtg agctatgaga aagcgccacg cttcccgaag ggagaaaggc    6780
ggacaggtat ccggtaagcg gcagggtcgg aacaggagag cgcacgaggg agcttccagg    6840
gggaaacgcc tggtatcttt atagtcctgt cgggtttcgc cacctctgac ttgagcgtcg    6900
atttttgtga tgctcgtcag gggggcggag cctatggaaa aacgccagca acgcggcctt    6960
tttacggttc ctggcctttt gctggccttt tgctcacatg ttctttcctg cgttatcccc    7020
tgattctgtg gataaccgta ttaccgcctt tgagtgagct gataccgctc gccgcagccg    7080
aacgaccgag cgcagcgagt cagtgagcga ggaagcggaa gagcgcccaa tacgcaaacc    7140
gcctctcccc gcgcgttggc cgattcatta atgcagctgg cacgacaggt ttcccgactg    7200
gaaagcgggc a                                                         7211
```

<210> SEQ ID NO 30
<211> LENGTH: 7211
<212> TYPE: DNA
<213> ORGANISM: Artificial
<220> FEATURE:
<223> OTHER INFORMATION: pD35-nH-cM-Axmi028-opt

<400> SEQUENCE: 30

```
accccaggct ttacactta tgcttccggc tcgtatgttg tgtggaattg tgagcggata      60
acaatttcac acaggaaaca gctatgacca tgattacgcc aagctcgaaa ttaaccctca    120
ctaaagggaa caaagctgg agctcactgg atttttggttt taggaattag aaatttttatt    180
gatagaagta ttttacaaat acaaatacat actaagggtt tcttatatgc tcaacacatg    240
agcgaaaccc tataagaacc ctaattccct tatctgggaa ctactcacac attattctgg    300
agaaaaatag agagagatag atttgtagag agagactggt gattttttgcg ggtcccgctc    360
agaagaactc gtcaagaagg cgatagaagg cgatgcgctg cgaatcggga gcggcgatac    420
cgtaaagcac gaggaagcgg tcagcccatt cgccgccaag ctcttcagca atatcacggg    480
tagccaacgc tatgtcctga tagcggtccg ccacacccag ccggccacag tcgatgaatc    540
cagaaaagcg gccattttcc accatgatat tcggcaagca ggcatcgcca tgggtcacga    600
cgagatcctc gccgtcgggc atgcgcgcct tgagcctggc gaacagttcg ctggcgcga    660
gccctgatg ctcttcgtcc agatcatcct gatcgacaag accggcttcc atccgagtac    720
gtgctcgctc gatgcgatgt ttcgcttggt ggtcgaatgg gcaggtagcc ggatcaagcg    780
tatgcagccg ccgcattgca tcagccatga tggatacttt ctcggcagga gcaaggtgag    840
atgacaggag atcctgcccc ggcacttcgc ccaatagcag ccagtccctt cccgcttcag    900
tgacaacgtc gagcacagct gcgcaaggaa cgcccgtcgt ggccagccac gatagccgcg    960
ctgcctcgtc ctgcagttca ttcagggcac cggacaggtc ggtcttgaca aaaagaaccg   1020
ggcgcccctg cgctgacagc cggaacacgg cggcatcaga gcagccgatt gtctgttgtg   1080
cccagtcata gccgaatagc ctctccaccc aagcggccgg agaacctgcg tgcaatccat   1140
cttgttcaat ccaagctccc atggtggcca ctcgaggtgc agattatttg gattgagagt   1200
gaatatgaga ctctaattgg ataccgaggg gaatttatgg aacgtcagtg gagcattttt   1260
gacaagaaat atttgctagc tgatagtgac cttaggcgac ttttgaacgc gcaataatgg   1320
tttctgacgt atgtgcttag ctcattaaac tccagaaacc cgcggctgag tggctccttc   1380
aacgttgcgg ttctgtcagt tccaaacgta aaacggcttg tcccgcgtca tcggcggggg   1440
tcataacgtg actcccttaa ttctccgctc atgatctaga ggccatggcg gccgctagat   1500
cgggccaaca tggtggagca cgacactctc gtctactcca agaatatcaa agatacagtc   1560
tcagaagacc aaagggctat tgagactttt caacaaaggg taatatcggg aaacctcctc   1620
ggattccatt gcccagctat ctgtcacttc atcaaaagga cagtagaaaa ggaaggtggc   1680
acctacaaat gccatcattg cgataaagga aaggctatcg ttcaagatgc ctctgccgac   1740
agtggtccca agatggaccc cccacccacg aggagcatcg tggaaaaaga agacgttcca   1800
accacgtctt caaagcaagt ggattgatgt gaacatggtg gagcacgaca ctctcgtcta   1860
ctccaagaat atcaaagata cagtctcaga gaccaaagg ctattgaga cttttcaaca   1920
agggtaata tcgggaaacc tcctcggatt ccattgccca gctatctgtc acttcatcaa   1980
aaggacagta gaaaaggaag gtggcaccta caaatgccat cattgcgata aaggaaaggc   2040
```

```
tatcgttcaa gatgcctctg ccgacagtgg tcccaaagat ggacccccac ccacgaggag    2100
catcgtggaa aaagaagacc ttccaaccac gtcttcaaag caagtggatt gatgtgatat    2160
ctccactgac gtaagggatg acgcacaatc ccactatcct tcgcaagacc cttcctctat    2220
ataaggaagt tcatttcatt tggagaggac acgctgaaat caccagtctc tctctacaaa    2280
tctatctctc tcgactagta tgcaccacca ccatcaccac atcgatatga accagaagaa    2340
ctacgagatc atcggcgcgt ccaccaacgg gacgatcgag ctgcccgagg attacaacac    2400
gatcgtcagc ccgtacgacg cgcctgcatc agtgacaacc accatcgaga tcacggggac    2460
aatcctgtct gacctcggtg tgcctggagc aagttcagtc agccttctgc tcaacaagct    2520
gatcaacctg ctctggccga acgacaccaa caccgtgtgg ggtacgttcg gcaaggagac    2580
ggccgatctc ctcaacgagg tcctgtcacc tgatgaccca gttgtcaagg acgctaatac    2640
gatcctcaag gggatcaacg ggtcgctgaa cctctacctg aacgccctcg agatctggaa    2700
gaaggacccg aacaacctga ctactatcga aacgtgact gactacttcc ggtcactcaa    2760
cgtcgtgttc acgcacgaca tgccctcgtt cgccgtccct ggatacgaga ccaagctgct    2820
caccatctac gcccaggctg caaacctcca tctgctgttg ctcagggacg catcacgttt    2880
cggtgaggga tggggtttga cccaggagat catcaacacg aactacaacg accagctccg    2940
cctcaccgcc gaatacaccg accactgcgt gaagtggtac aacgccggct tggagaagct    3000
gaagggcaac ctcacgggtg agaactggta cacgtacaac cggttccgca gggagatgac    3060
cctcatggtg ctggacgtgg tcgcattgtt cccaaactac gacacccgca tgtacccgat    3120
cgggacatca agcgagctta cccgtatgat ctacactgac cccatcgcct acacccagtc    3180
cgacccatgg tacaagatca cgtccctgag cttctcgaac atcgagaaca gcgcgatccc    3240
ctccccatcg ttcttccgct ggctcaagtc cgtcagcatt aactcccagt ggtggggttc    3300
cggaccttca caaacctact actgggtggg gcacgaactg gtctacagca acagcaacag    3360
caaccagtcg ctgaaggtga agtacggcga ccctaacagc ttcatcgagc ccccggattc    3420
cttctccttc agcagcacgg acgtgtacag gaccatctca gtcgtgcgta ttccgtgtc    3480 gaactacatc gtgtcggagg tgcggttcaa cagcatctcc tccaccaacc agatcagcga    3540
ggaaatctac aagcaccagt ctaactggag ccggcaggag acaaaggact caatcaccga    3600
gctgagcctg gccgccaacc cgccaaccac gttcggaaac gttgccgagt acagtcaccg    3660
cctggcttac atctcagagg cgtaccagtc tcacaaccca tctaagtacc cgacctatat    3720
ccccgtgttc gggtggaccc acacatccgt gaggtacgac aacaagattt ccccggacaa    3780
gatcacgcag atccccgcgg ttaagagtag ctcagctcag gggggaagct ggaagaatat    3840
cgtcaagggg cccggattca cgggtggaga cgtgacgacg gcggtttcac ctgcaactgt    3900
tacggatatt atcaagatcc aggttaccct tgatcccaac agtctgagcc agaagtatcg    3960
ggcacgcctt cgctacgcca gcaacgcctt cgtcccggca acctttata cgaacacctc    4020 gtcaaactac aacttcgaac tgaagaaggg cacgactgag cagttcacga cctacaacag    4080
ctaccagtac gtggacatcc ccggcagcat ccagttcaac aatacgtccg acaccgtgtc    4140
ggtctacctg cacatggact caacctcgaa cgtgaacgtg cacgtggacc ggatcgagtt    4200
catcccgatc gacggaaagc ttacggagca gaagctgatc tccgaggagg acctgtaacg    4260
tgtcgaccct gctttaatga gatatgcgag acgcctatga tcgcatgata tttgctttca    4320
attctgttgt gcacgttgta aaaaacctga gcatgtgtag ctcagatcct taccgccggt    4380
ttcggttcat tctaatgaat atatcacccg ttactatcgt atttttatga ataatattct    4440
```

```
ccgttcaatt tactgattgt cctcgacagg ccttaagggc cagatcttgg gcccggtacc   4500
caattcgccc tatagtgagt cgtattacaa ttcactggcc gtcgttttac aacgtcgtga   4560
ctgggaaaac cctggcgtta cccaacttaa tcgccttgca gcacatcccc ctttcgccag   4620
ctggcgtaat agcgaagagg cccgcaccga tcgcccttcc caacagttgc gcagcctgaa   4680
tggcgaatgg aaattgtaag cgttaatatt ttgttaaaat tcgcgttaaa ttttttgttaa   4740
atcagctcat tttttaacca ataggccgaa atcggcaaaa tcccttataa atcaaaagaa   4800
tagaccgaga tagggttgag tgttgttcca gtttggaaca agagtccact attaagaac   4860
gtggactcca acgtcaaagg gcgaaaaacc gtctatcagg gcgatggccc actacgtgaa   4920
ccatcaccct aatcaagttt ttggggtcg aggtgccgta aagcactaaa tcggaaccct   4980
aaagggagcc cccgatttag agcttgacgg ggaaagccgg cgaacgtggc gagaaaggaa   5040
gggaagaaag cgaaaggagc gggcgctagg gcgctggcaa gtgtagcggt cacgctgcgc   5100
gtaaccacca cacccgccgc gcttaatgcg ccgctacagg gcgcgtcagg tggcactttt   5160
cggggaaatg tgcgcggaac ccctatttgt ttatttttct aaatacattc aaatatgtat   5220
ccgctcatga caataaacc ctgataaatg cttcaataat attgaaaaag gaagagtatg   5280
agtattcaac atttccgtgt cgcccttatt ccctttttg cggcattttg ccttcctgtt   5340
tttgctcacc cagaaacgct ggtgaaagta aaagatgctg aagatcagtt gggtgcacga   5400
gtgggttaca tcgaactgga tctcaacagc ggtaagatcc ttgagagttt tcgccccgaa   5460
gaacgttttc caatgatgag cacttttaaa gttctgctat gtggcgcggt attatcccgt   5520
attgacgccg ggcaagagca actcggtcgc cgcatacact attctcagaa tgacttggtt   5580
gagtactcac cagtcacaga aaagcatctt acggatggca tgacagtaag agaattatgc   5640
agtgctgcca taaccatgag tgataacact gcggccaact tacttctgac aacgatcgga   5700
ggaccgaagg agctaaccgc ttttttgcac aacatggggg atcatgtaac tcgccttgat   5760
cgttgggaac cggagctgaa tgaagccata ccaaacgacg agcgtgacac cacgatgcct   5820
gtagcaatgg caacaacgtt gcgcaaacta ttaactggcg aactacttac tctagcttcc   5880
cggcaacaat taatagactg gatggaggcg gataaagttg caggaccact tctgcgctcg   5940
gcccttccgg ctggctggtt tattgctgat aaatctggag ccggtgagcg tgggtctcgc   6000
ggtatcattg cagcactggg gccagatggt aagccctccc gtatcgtagt tatctacacg   6060
acggggagtc aggcaactat ggatgaacga atagacaga tcgctgagat aggtgcctca   6120
ctgattaagc attggtaact gtcagaccaa gtttactcat atatacttta gattgattta   6180
aaacttcatt tttaatttaa aaggatctag gtgaagatcc ttttttgataa tctcatgacc   6240
aaaatccctt aacgtgagtt ttcgttccac tgagcgtcag accccgtaga aaagatcaaa   6300
ggatcttctt gagatccttt ttttctgcgc gtaatctgct gcttgcaaac aaaaaaacca   6360
ccgctaccag cggtggtttg tttgccggat caagagctac caactctttt tccgaaggta   6420
actggcttca gcagagcgca gataccaaat actgtccttc tagtgtagcc gtagttaggc   6480
caccacttca agaactctgt agcaccgcct acatacctcg ctctgctaat cctgttacca   6540
gtggctgctg ccagtggcga taagtcgtgt cttaccgggt tggactcaag acgatagtta   6600
ccggataagg cgcagcggtc gggctgaacg gggggttcgt gcacacagcc cagcttggag   6660
cgaacgacct acaccgaact gagatacctta cagcgtgagc tatgagaaag cgccacgctt   6720
cccgaaggga gaaaggcgga caggtatccg gtaagcggca gggtcggaac aggagagcgc   6780
```

| | |
|---|---:|
| acgagggagc ttccagggggg aaacgcctgg tatctttata gtcctgtcgg gtttcgccac | 6840 |
| ctctgacttg agcgtcgatt tttgtgatgc tcgtcagggg ggcggagcct atggaaaaac | 6900 |
| gccagcaacg cggccttttt acggttcctg gccttttgct ggccttttgc tcacatgttc | 6960 |
| tttcctgcgt tatcccctga ttctgtggat aaccgtatta ccgcctttga gtgagctgat | 7020 |
| accgctcgcc gcagccgaac gaccgagcgc agcgagtcag tgagcgagga agcggaagag | 7080 |
| cgcccaatac gcaaaccgcc tctccccgcg cgttggccga ttcattaatg cagctggcac | 7140 |
| gacaggtttc ccgactggaa agcgggcagt gagcgcaacg caattaatgt gagttagctc | 7200 |
| actcattagg c | 7211 |

```
<210> SEQ ID NO 31
<211> LENGTH: 7211
<212> TYPE: DNA
<213> ORGANISM: Artificial
<220> FEATURE:
<223> OTHER INFORMATION: pD35-nH-cM-Axmi028-optpA

<400> SEQUENCE: 31
```

| | |
|---|---:|
| taaagcacta aatcggaacc ctaaagggag cccccgattt agagcttgac ggggaaagcc | 60 |
| ggcgaacgtg gcgagaaagg aagggaagaa agcgaaagga gcgggcgcta gggcgctggc | 120 |
| aagtgtagcg gtcacgctgc gcgtaaccac cacacccgcc gcgcttaatg cgccgctaca | 180 |
| gggcgcgtca ggtggcactt tcggggaaa tgtgcgcgga accccta ttt gtttattttt | 240 |
| ctaaatacat tcaaatatgt atccgctcat gagacaataa ccctgataaa tgcttcaata | 300 |
| atattgaaaa aggaagagta tgagtattca acatttccgt gtcgccctta ttcccttttt | 360 |
| tgcggcattt tgccttcctg ttttt gctca cccagaaacg ctggtgaaag taaaagatgc | 420 |
| tgaagatcag ttgggtgcac gagtgggtta catcgaactg gatctcaaca gcggtaagat | 480 |
| ccttgagagt tttcgccccg aagaacgttt tccaatgatg agcactttta aagttctgct | 540 |
| atgtggcgcg gtattatccc gtattgacgc cgggcaagag caactcggtc gccgcataca | 600 |
| ctattctcag aatgacttgg ttgagtactc accagtcaca gaaaagcatc ttacggatgg | 660 |
| catgacagta agagaattat gcagtgctgc cataaccatg agtgataaca ctgcggccaa | 720 |
| cttacttctg acaacgatcg gaggaccgaa ggagctaacc gcttttttgc acaacatggg | 780 |
| ggatcatgta actcgccttg atcgttggga accggagctg aatgaagcca taccaaacga | 840 |
| cgagcgtgac accacgatgc ctgtagcaat ggcaacaacg ttgcgcaaac tattaactgg | 900 |
| cgaactactt actctagctt cccggcaaca attaatagac tggatggagg cggataaagt | 960 |
| tgcaggacca cttctgcgct cggcccttcc ggctggctgg tttattgctg ataaatctgg | 1020 |
| agccggtgag cgtgggtctc gcggtatcat tgcagcactg gggccagatg gtaagccctc | 1080 |
| ccgtatcgta gttatctaca cgacggggag tcaggcaact atggatgaac gaaatagaca | 1140 |
| gatcgctgag ataggtgcct cactgattaa gcattggtaa ctgtcagacc aagtttactc | 1200 |
| atatatactt tagattgatt taaaacttca ttttaatttt aaaaggatct aggtgaagat | 1260 |
| cctttttgat aatctcatga ccaaaatccc ttaacgtgag ttttcgttcc actgagcgtc | 1320 |
| agaccccgta gaaaagatca aaggatcttc ttgagatcct ttttttctgc gcgtaatctg | 1380 |
| ctgcttgcaa acaaaaaaac caccgctacc agcggtggtt tgtttgccgg atcaagagct | 1440 |
| accaactctt tttccgaagg taactggctt cagcagagcg cagataccaa atactgtcct | 1500 |
| tctagtgtag ccgtagttag gccaccactt caagaactct gtagcaccgc ctacatacct | 1560 |
| cgctctgcta atcctgttac cagtggctgc tgccagtggc gataagtcgt gtcttaccgg | 1620 |

-continued

```
gttggactca agacgatagt taccggataa ggcgcagcgg tcgggctgaa cgggggttc    1680 gtgcacacag cccagcttgg agcgaacgac ctacaccgaa ctgagatacc tacagcgtga    1740
gctatgagaa agcgccacgc ttcccgaagg gagaaaggcg gacaggtatc cggtaagcgg    1800
cagggtcgga acaggagagc gcacgaggga gcttccaggg ggaaacgcct ggtatcttta    1860
tagtcctgtc gggtttcgcc acctctgact tgagcgtcga ttttttgtgat gctcgtcagg    1920 ggggcggagc ctatggaaaa acgccagcaa cgcggccttt ttacggttcc tggccttttg    1980
ctggcctttt gctcacatgt tctttcctgc gttatcccct gattctgtgg ataaccgtat    2040
taccgccttt gagtgagctg ataccgctcg ccgcagccga acgaccgagc gcagcgagtc    2100
agtgagcgag gaagcggaag agcgcccaat acgcaaaccg cctctccccg cgcgttggcc    2160
gattcattaa tgcagctggc acgacaggtt tcccgactgg aaagcgggca gtgagcgcaa    2220
cgcaattaat gtgagttagc tcactcatta ggcaccccag gctttacact ttatgcttcc    2280
ggctcgtatg ttgtgtggaa ttgtgagcgg ataacaattt cacacaggaa acagctatga    2340
ccatgattac gccaagctcg aaattaaccc tcactaaagg gaacaaaagc tggagctcac    2400
tggattttgg ttttaggaat tagaaatttt attgatagaa gtattttaca aatacaaata    2460
catactaagg gtttcttata tgctcaacac atgagcgaaa ccctataaga accctaattc    2520
ccttatctgg gaactactca cacattattc tggagaaaaa tagagagaga tagatttgta    2580
gagagagact ggtgattttt gcgggtcccg ctcagaagaa ctcgtcaaga aggcgataga    2640
aggcgatgcg ctgcgaatcg ggagcggcga taccgtaaag cacgaggaag cggtcagccc    2700
attcgccgcc aagctcttca gcaatatcac gggtagccaa cgctatgtcc tgatagcggt    2760
ccgccacacc cagccggcca cagtcgatga atccagaaaa gcggccattt tccaccatga    2820
tattcggcaa gcaggcatcg ccatgggtca cgacgagatc ctcgccgtcg gcatgcgcg    2880 ccttgagcct ggcgaacagt tcggctggcg cgagccctg atgctcttcg tccagatcat    2940
cctgatcgac aagaccggct tccatccgag tacgtgctcg ctcgatgcga tgtttcgctt    3000
ggtggtcgaa tgggcaggta gccggatcaa gcgtatgcag ccgccgcatt gcatcagcca    3060
tgatggatac tttctcggca ggagcaaggt gagatgacag gagatcctgc cccggcactt    3120
cgcccaatag cagccagtcc cttcccgctt cagtgacaac gtcgagcaca gctgcgcaag    3180
gaacgcccgt cgtggccagc cacgatagcc gcgctgcctc gtcctgcagt tcattcaggg    3240
caccggacag gtcggtcttg acaaaaagaa ccgggcgccc ctgcgctgac agccggaaca    3300
cggcggcatc agagcagccg attgtctgtt gtgcccagtc atagccgaat agcctctcca    3360
cccaagcggc cggagaacct gcgtgcaatc catcttgttc aatccaagct cccatggtgg    3420
ccactcgagg tgcagattat ttggattgag agtgaatatg agactctaat tggataccga    3480
ggggaattta tggaacgtca gtggagcatt tttgacaaga aatatttgct agctgatagt    3540
gaccttaggc gacttttgaa cgcgcaataa tggtttctga cgtatgtgct tagctcatta    3600
aactccagaa acccgcggct gagtggctcc ttcaacgttg cggttctgtc agttccaaac    3660
gtaaaacggc ttgtcccgcg tcatcggcgg gggtcataac gtgactccct taattctccg    3720
ctcatgatct agaggccatg gcggccgcta gatcgggcca acatggtgga gcacgacact    3780
ctcgtctact ccaagaatat caaagataca gtctcagaag accaaagggc tattgagact    3840
tttcaacaaa gggtaatatc gggaaacctc ctcggattcc attgcccagc tatctgtcac    3900
ttcatcaaaa ggacagtaga aaaggaaggt ggcacctaca aatgccatca ttgcgataaa    3960
```

```
ggaaaggcta tcgttcaaga tgcctctgcc gacagtggtc ccaaagatgg accccccaccc    4020 acgaggagca tcgtggaaaa agaagacgtt ccaaccacgt cttcaaagca agtggattga    4080
tgtgaacatg gtggagcacg acactctcgt ctactccaag aatatcaaag atacagtctc    4140
agaagaccaa agggctattg agacttttca acaaagggta atatcgggaa acctcctcgg    4200
attccattgc ccagctatct gtcacttcat caaaaggaca gtagaaaagg aaggtggcac    4260
ctacaaatgc catcattgcg ataaaggaaa ggctatcgtt caagatgcct ctgccgacag    4320
tggtcccaaa gatggacccc cacccacgag gagcatcgtg gaaaagaag accttccaac     4380 cacgtcttca aagcaagtgg attgatgtga tatctccact gacgtaaggg atgacgcaca    4440
atcccactat ccttcgcaag acccttcctc tatataagga agttcatttc atttggagag    4500
gacacgctga atcaccagt ctctctctac aaatctatct ctctcgacta gtatgcacca     4560
ccaccatcac cacatcgata tgaatcaaaa gaactatgaa atcatcggcg cgtccaccaa    4620
cgggacgatc gagctgcccg aggattacaa cacgatcgtc agcccgtacg acgcgcctgc    4680
atcagtgaca accaccatcg agatcacggg gacaatacta tctgacctcg gtgtgcctgg    4740
agcaagttca gtcagcctttc tgctcaataa actgatcaac ctgctctggc cgaacgacac    4800
caacaccgtg tggggtacgt tcggcaagga gacggccgat ctcctcaacg aggtcctgtc    4860
acctgatgac ccagttgtca aggacgctaa tacgatcctc aagggaataa acgggtcgct    4920
gaacctctac ctgaacgccc tcgagatctg gaagaaggac ccgaacaacc tgactactat    4980
cgagaacgtg actgactact tccggtcact caacgtcgtg ttcacgcacg acatgccctc    5040
gttcgccgtc cctggatatg aaaccaagct gctcaccatc tacgcccagg ctgcaaacct    5100
ccatctgctg ttgctcaggg acgcatcacg tttcggtgag ggatggggtt tgacccagga    5160
gatcataaat actaactaca acgaccagct ccgcctcacc gccgaataca ccgaccactg    5220
cgtgaagtgg tacaacgccg gcttggagaa attaaagggc aacctcacgg gtgagaactg    5280
gtacacgtac aaccggttcc gcagggagat gaccctcatg gtgctggacg tggtcgcatt    5340
gttcccaaac tacgacaccc gcatgtaccc gatcgggaca tcaagcgagc ttacccgtat    5400
gatctacact gaccccatcg cctacaccca gtccgaccca tggtacaaga tcacgtccct    5460
gagcttctcg aacatcgaga acagcgcgat cccctcccca tcgttcttcc gctggctcaa    5520
gtccgtctca attaattccc agtggtgggg ttccggacct tcacaaacct actactgggt    5580
ggggcacgaa ctggtctaca gcaacagcaa cagcaatcaa tcgctgaagg tgaagtacgg    5640 cgacccctaac agcttcatcg agccccggga ttccttctcc ttcagcagca cggacgtgta    5700
caggaccatc tcagtcgtgc gtaattccgt gtcgaactac atcgtgtcgg aggtgcggtt    5760
caacagcatc tcctccacca atcaaatcag cgaggaaatc tacaagcacc aatcaaactg    5820
gagccggcag gaaaccaagg actcaatcac cgagctgagc ctggccgcca acccgccaac    5880
cacgttcgga aacgttgccg aatacagtca ccgcctggct tacatctcag aggcgtacca    5940
gtctcacaac ccatcaaaat acccgaccta tatcccgtg ttcgggtgga cccacacatc     6000
cgtgaggtac gacaataaaa ttttccggga caagatcacg cagatccccg cggttaagag    6060
tagctcagct cagggggggaa gctggaaaaa tatcgtcaag gggcccggat tcacgggtgg    6120
agacgtgacg acggcggttt cacctgcaac tgttacggat ataataaaaa tacaggttac    6180
ccttgatccc aacagtctga gccaaaaata tcgggcacgc cttcgctacg ccagcaacgc    6240
cttcgtcccg gcaaccctttt atacgaatac atcgtcaaac tacaacttcg aactgaagaa    6300
gggcacgact gagcagttca cgacatataa cagctaccag tacgtggaca tccccggctc    6360
```

```
aatacagttc aataatacgt ccgacaccgt gtcggtctac ctgcacatgg actcaacctc    6420
gaacgtgaac gtgcacgtgg accggatcga gttcatcccg atcgacggaa agcttacgga    6480
gcagaagctg atctccgagg aggacctgta acgtgtcgac cctgctttaa tgagatatgc    6540
gagacgccta tgatcgcatg atatttgctt tcaattctgt tgtgcacgtt gtaaaaaacc    6600
tgagcatgtg tagctcagat ccttaccgcc ggtttcggtt cattctaatg aatatatcac    6660
ccgttactat cgtatttta tgaataatat tctccgttca atttactgat tgtcctcgac    6720
aggccttaag ggccagatct tgggcccggt acccaattcg ccctatagtg agtcgtatta    6780
caattcactg gccgtcgttt tacaacgtcg tgactgggaa aaccctggcg ttacccaact    6840
taatcgcctt gcagcacatc cccctttcgc cagctggcgt aatagcgaag aggcccgcac    6900
cgatcgcccc tcccaacagt tgcgcagcct gaatggcgaa tggaaattgt aagcgttaat    6960
attttgttaa aattcgcgtt aaattttgt taaatcagct cattttttaa ccaataggcc    7020
gaaatcggca aaatcccta taaatcaaaa gaatagaccg agataggggtt gagtgttgtt    7080 ccagtttgga acaagagtcc actattaaag aacgtggact ccaacgtcaa agggcgaaaa    7140
accgtctatc agggcgatgg cccactacgt gaaccatcac cctaatcaag ttttttgggg    7200
tcgaggtgcc g                                                         7211

<210> SEQ ID NO 32
<211> LENGTH: 7211
<212> TYPE: DNA
<213> ORGANISM: Artificial
<220> FEATURE:
<223> OTHER INFORMATION: pD35-nH-cM-Axmi028-opt3pA

<400> SEQUENCE: 32
gccgctacag ggcgcgtcag gtggcacttt tcggggaaat gtgcgcggaa cccctatttg      60 tttattttc taaatacatt caaatatgta tccgctcatg agacaataac cctgataaat     120
gcttcaataa tattgaaaaa ggaagagtat gagtattcaa catttccgtg tcgcccttat     180 tcccttttt gcggcatttt gccttcctgt ttttgctcac ccagaaacgc tggtgaaagt     240
aaaagatgct gaagatcagt tgggtgcacg agtgggttac atcgaactgg atctcaacag     300
cggtaagatc cttgagagtt ttcgccccga agaacgtttt ccaatgatga gcacttttaa     360
agttctgcta tgtggcgcgg tattatcccg tattgacgcc gggcaagagc aactcggtcg     420
ccgcatacac tattctcaga atgacttggt tgagtactca ccagtcacag aaaagcatct     480
tacggatggc atgacagtaa gagaattatg cagtgctgcc ataaccatga gtgataacac     540
tgcggccaac ttacttctga acgatcgg aggaccgaag gagctaaccg cttttttgca     600
caacatgggg gatcatgtaa ctcgccttga tcgttgggaa ccggagctga atgaagccat     660
accaaacgac gagcgtgaca ccacgatgcc tgtagcaatg gcaacaacgt tgcgcaaact     720
attaactggc gaactactta ctctagcttc ccggcaacaa ttaatagact ggatggaggc     780
ggataaagtt gcaggaccac ttctgcgctc ggcccttccg gctggctggt ttattgctga     840
taaatctgga gccggtgagc gtgggtctcg cggtatcatt gcagcactgg ggccagatgg     900
taagccctcc cgtatcgtag ttatctacac gacggggagt caggcaacta tggatgaacg     960
aaatagacag atcgctgaga taggtgcctc actgattaag cattggtaac tgtcagacca    1020
agtttactca tatatacttt agattgattt aaaacttcat ttttaattta aaaggatcta    1080
ggtgaagatc cttttgata atctcatgac caaaatccct aacgtgagt tttcgttcca    1140
```

```
ctgagcgtca gaccccgtag aaaagatcaa aggatcttct tgagatcctt ttttctgcg    1200
cgtaatctgc tgcttgcaaa caaaaaaacc accgctacca gcggtggttt gtttgccgga   1260
tcaagagcta ccaactcttt ttccgaaggt aactggcttc agcagagcgc agataccaaa   1320
tactgtcctt ctagtgtagc cgtagttagg ccaccacttc aagaactctg tagcaccgcc   1380
tacatacctc gctctgctaa tcctgttacc agtggctgct gccagtggcg ataagtcgtg   1440
tcttaccggg ttggactcaa gacgatagtt accggataag gcgcagcggt cgggctgaac   1500
ggggggttcg tgcacacagc ccagcttgga gcgaacgacc tacaccgaac tgagatacct   1560
acagcgtgag ctatgagaaa gcgccacgct tcccgaaggg agaaaggcgg acaggtatcc   1620
ggtaagcggc agggtcggaa caggagagcg cacgagggag cttccagggg gaaacgcctg   1680
gtatctttat agtcctgtcg ggtttcgcca cctctgactt gagcgtcgat ttttgtgatg   1740
ctcgtcaggg gggcggagcc tatggaaaaa cgccagcaac gcggcctttt tacggttcct   1800
ggccttttgc tggccttttg ctcacatgtt ctttcctgcg ttatccctg attctgtgga    1860
taaccgtatt accgcctttg agtgagctga taccgctcgc cgcagccgaa cgaccgagcg   1920
cagcgagtca gtgagcgagg aagcggaaga gcgcccaata cgcaaaccgc ctctccccgc   1980
gcgttggccg attcattaat gcagctgca cgacaggttt cccgactgga aagcgggcag    2040
tgagcgcaac gcaattaatg tgagttagct cactcattag gcaccccagg ctttacactt   2100
tatgcttccg gctcgtatgt tgtgtggaat tgtgagcgga taacaatttc acacaggaaa   2160
cagctatgac catgattacg ccaagctcga attaaccct cactaaaggg aacaaaagct     2220
ggagctcact ggattttggt tttaggaatt agaaatttta ttgatagaag tattttacaa   2280
atacaaatac atactaaggg tttcttatat gctcaacaca tgagcgaaac cctataagaa   2340
ccctaattcc cttatctggg aactactcac acattattct ggagaaaaat agagagagat   2400
agatttgtag agagagactg gtgattttg cgggtcccgc tcagaagaac tcgtcaagaa    2460
ggcgatagaa ggcgatgcgc tgcgaatcgg agcggcgat accgtaaagc acgaggaagc    2520
ggtcagccca ttcgccgcca agctcttcag caatatcacg ggtagccaac gctatgtcct   2580
gatagcggtc cgccacaccc agccggccac agtcgatgaa tccagaaaag cggccatttt   2640
ccaccatgat attcggcaag caggcatcgc catgggtcac gacgagatcc tcgccgtcgg   2700
gcatgcgcgc cttgagcctg gcgaacagtt cggctggcgc gagcccctga tgctcttcgt   2760
ccagatcatc ctgatcgaca agaccggctt ccatccgagt acgtgctcgc tcgatgcgat   2820
gtttcgcttg gtggtcgaat gggcaggtag ccggatcaag cgtatgcagc cgccgcattg   2880
catcagccat gatggatact ttctcggcag gagcaaggtg agatgacagg agatcctgcc   2940
ccggcacttc gcccaatagc agccagtccc ttcccgcttc agtgacaacg tcgagcacag   3000
ctgcgcaagg aacgcccgtc gtggccagcc acgatagccg cgctgcctcg tcctgcagtt   3060
cattcagggc accggacagg tcggtcttga caaaaagaac cgggcgcccc tgcgctgaca   3120
gccggaacac ggcggcatca gagcagccga ttgtctgttg tgcccagtca tagccgaata   3180
gcctctccac ccaagcggcc ggagaacctg cgtgcaatcc atcttgttca atccaagctc   3240
ccatggtggc cactcgaggt gcagattatt tggattgaga gtgaatatga gactctaatt   3300
ggataccgag gggaatttat ggaacgtcag tggagcattt ttgacaagaa atatttgcta   3360
gctgatagtg accttaggcg acttttgaac gcgcaataat ggtttctgac gtatgtgctt   3420
agctcattaa actccagaaa cccgcggctg agtggctcct tcaacgttgc ggttctgtca   3480
gttccaaacg taaaacggct tgtcccgcgt catcggcggg ggtcataacg tgactccctt   3540
```

```
aattctccgc tcatgatcta gaggccatgg cggccgctag atcgggccaa catggtggag    3600
cacgacactc tcgtctactc caagaatatc aaagatacag tctcagaaga ccaaagggct    3660
attgagactt ttcaacaaag ggtaatatcg ggaaacctcc tcggattcca ttgcccagct    3720
atctgtcact tcatcaaaag gacagtagaa aaggaaggtg gcacctacaa atgccatcat    3780
tgcgataaag gaaaggctat cgttcaagat gcctctgccg acagtggtcc caaagatgga    3840
cccccaccca cgaggagcat cgtggaaaaa gaagacgttc caaccacgtc ttcaaagcaa    3900
gtggattgat gtgaacatgg tggagcacga cactctcgtc tactccaaga atatcaaaga    3960
tacagtctca gaagaccaaa gggctattga gacttttcaa caaagggtaa tatcgggaaa    4020
cctcctcgga ttccattgcc cagctatctg tcacttcatc aaaaggacag tagaaaagga    4080
aggtggcacc tacaaatgcc atcattgcga taaaggaaag gctatcgttc aagatgcctc    4140
tgccgacagt ggtcccaaag atggaccccc acccacgagg agcatcgtgg aaaagaaga    4200 ccttccaacc acgtcttcaa agcaagtgga ttgatgtgat atctccactg acgtaaggga    4260
tgacgcacaa tcccactatc cttcgcaaga cccttcctct atataaggaa gttcatttca    4320
tttggagagg acacgctgaa atcaccagtc tctctctaca aatctatctc tctcgactag    4380
tatgcaccac caccatcacc acatcgatat gaaccagaag aactacgaga tcatcggcgc    4440
gtccaccaac gggacgatcg agctgcccga ggattacaac acgatcgtca gcccgtacga    4500
cgcgcctgca tcagtgacaa ccaccatcga gatcacgggg acaatcctgt ctgacctcgg    4560
tgtgcctgga gcaagttcag tcagccttct gctcaacaag ctgatcaacc tgctctggcc    4620
gaacgacacc aacaccgtgt ggggtacgtt cggcaaggag acggccgatc tcctcaacga    4680
ggtcctgtca cctgatgacc cagttgtcaa ggacgctaat acgatcctca agggatcaa    4740 cgggtcgctg aacctctacc tgaacgccct cgagatctgg aagaaggacc cgaacaacct    4800
gactactatc gagaacgtga ctgactactt ccggtcactc aacgtcgtgt tcacgcacga    4860
catgccctcg ttcgccgtcc ctggatacga gaccaagctg ctcaccatct acgcccaggc    4920
tgcaaacctc catctgctgt tgctcaggga cgcatcacgt ttcggtgagg gatgggttt    4980 gacccaggag atcatcaaca cgaactacaa cgaccagctc cgcctcaccg ccgaatacac    5040
cgaccactgc gtgaagtggt acaacgccgg cttggagaag ctgaagggca acctcacggg    5100
tgagaactgg tacacgtaca accggttccg cagggagatg accctcatgg tgctggacgt    5160
ggtcgcattg ttcccaaact acgacacccg catgtacccg atcgggacat caagcgagct    5220
tacccgtatg atctacactg accccatcgc ctacacccag tccgacccat ggtacaagat    5280
cacgtccctg agcttctcga acatcgagaa cagcgcgatc ccctcccat cgttcttccg    5340 ctggctcaag tccgtcagca ttaactccca gtggtgggt tccggaccctt cacaaaccta    5400 ctactgggtg gggcacgaac tggtctacag caacagcaac agcaatcaat cgctgaaggt    5460
gaagtacggc gaccctaaca gcttcatcga gcccccggat tccttctcct tcagcagcac    5520
ggacgtgtac aggaccatct cagtcgtgcg taattccgtg tcgaactaca tcgtgtcgga    5580
ggtgcggttc aacagcatct cctccaccaa ccagatcagc gaggaaatct acaagcacca    5640
atcaaactgg agcggcagg agacaaagga ctcaatcacc gagctgagcc tggccgccaa    5700
cccgccaacc acgttcggaa acgttgccga gtacagtcac cgcctggctt acatctcaga    5760
ggcgtaccag tctcacaacc catctaagta cccgacctat atcccgtgt tcgggtggac    5820 ccacacatcc gtgaggtacg acaacaagat ttttcccggac aagatcacgc agatccccgc    5880
```

```
ggttaagagt agctcagctc agggggggaag ctggaagaat atcgtcaagg ggcccggatt    5940
cacgggtgga gacgtgacga cggcggtttc acctgcaact gttacggata ttatcaagat    6000
ccaggttacc cttgatccca acagtctgag ccagaagtat cgggcacgcc ttcgctacgc    6060
cagcaacgcc ttcgtcccgg caacccttta tacgaacacc tcgtcaaact acaacttcga    6120
actgaagaag ggcacgactg agcagttcac gacctacaac agctaccagt acgtggacat    6180
ccccggcagc atccagttca acaatacgtc cgacaccgtg tcggtctacc tgcacatgga    6240
ctcaacctcg aacgtgaacg tgcacgtgga ccggatcgag ttcatcccga tcgacggaaa    6300
gcttacggag cagaagctga tctccgagga ggacctgtaa cgtgtcgacc ctgctttaat    6360
gagatatgcg agacgcctat gatcgcatga tatttgcttt caattctgtt gtgcacgttg    6420
taaaaaacct gagcatgtgt agctcagatc cttaccgccg gtttcggttc attctaatga    6480
atatatcacc cgttactatc gtatttttat gaataatatt ctccgttcaa tttactgatt    6540
gtcctcgaca ggccttaagg gccagatctt gggcccggta cccaattcgc cctatagtga    6600
gtcgtattac aattcactgg ccgtcgtttt acaacgtcgt gactgggaaa accctggcgt    6660
tacccaactt aatcgccttg cagcacatcc ccctttcgcc agctggcgta atagcgaaga    6720
ggcccgcacc gatcgccctt cccaacagtt gcgcagcctg aatggcgaat ggaaattgta    6780
agcgttaata ttttgttaaa attcgcgtta aattttttgtt aaatcagctc attttttaac    6840
caataggccg aaatcggcaa aatcccttat aaatcaaaag aatagaccga gatagggttg    6900
agtgttgttc cagtttggaa caagagtcca ctattaaaga acgtggactc caacgtcaaa    6960
gggcgaaaaa ccgtctatca gggcgatggc ccactacgtg aaccatcacc ctaatcaagt    7020
tttttggggt cgaggtgccg taaagcacta atcggaacc ctaaagggag ccccgatt     7080
agagcttgac ggggaaagcc ggcgaacgtg gcgagaaagg aagggaagaa agcgaagga    7140
gcgggcgcta gggcgctggc aagtgtagcg gtcacgctgc gcgtaaccac cacacccgcc    7200
gcgcttaatg c                                                          7211

<210> SEQ ID NO 33
<211> LENGTH: 12956
<212> TYPE: DNA
<213> ORGANISM: Artificial
<220> FEATURE:
<223> OTHER INFORMATION: p7U70SubiintrontDT

<400> SEQUENCE: 33
cggccgcgtc gagcgatcta gtaacataga tgacaccgcg cgcgataatt tatcctagtt      60
tgcgcgctat attttgtttt ctatcgcgta ttaaatgtat aattgcggga ctctaatcat     120
aaaaacccat ctcataaata acgtcatgca ttacatgtta attattacat gcttaacgta     180
attcaacaga aattatatga taatcatcgc aagaccggca acaggattca atcttaagaa     240
actttattgc caaatgtttg aacgatcggg gaaattcgag ctaattactc atgatcaggt     300
acctctagac ttgtacagct cgtccatgcc gtacaggaac aggtggtggc ggccctcgga     360
gcgctcgtac tgttccacga tggtgtagtc ctcgttgtgg gaggtgatgt ccagcttggt     420
gtccacgtag tagtagccgg gcagttgcac gggcttcttg ccatgtagat ggtcttgaa     480
ctccaccagg tagtggccgc cgtccttcag cttcagggcc tggtggatct cgcccttcag     540
cacgccgtcg cgggggtaca ggcgctcggt ggaggcctcc cagcccatgg tcttcttctg     600
cattacgggg ccgtcggggg ggaagttggt gccgcgcatc ttcaccttgt agatcagcgt     660
gccgtcctgc agggaggagt cctgggtcac ggtcaccaga ccgccgtcct cgaagttcat     720
```

```
cacgcgctcc cacttgaagc cctcggggaa ggacagcttc ttgtaatcgg ggatgtcggc    780
ggggtgcttc acgtacgcct tggagccgta catgaactgg ggggacagga tgtcccaggc    840
gaagggcagg gggccgccct tggtcacctt cagcttggcg gtctgggtgc cctcgtaggg    900
gcggccctcg ccctcgccct cgatctcgaa ctcgtggccg ttcatggagc cctccatgcg    960
caccttgaag cgcatgaact ctttgatgac ctcctcgccc ttgctcacca tggtggcggg   1020
atcgcgccct atcgttcgta aatggtgaaa attttcagaa aattgctttt gctttaaaag   1080
aaatgattta aattgctgca atagaagtag aatgcttgat tgcttgagat tcgtttgttt   1140
tgtatatgtt gtgttgagag gatcctctag agtcgacctg cagaagtaac accaaacaac   1200
agggtgagca tcgacaaaag aaacagtacc aagcaaataa atagcgtatg aaggcagggc   1260
taaaaaaatc cacatatagc tgctgcatat gccatcatcc aagtatatca agatcaaaat   1320
aattataaaa catacttgtt tattataata gataggtact caaggttaga gcatatgaat   1380
agatgctgca tatgccatca tgtatatgca tcagtaaaac ccacatcaac atgtatacct   1440
atcctagatc gatatttcca tccatcttaa actcgtaact atgaagatgt atgacacaca   1500
catacagttc caaaattaat aaatacacca ggtagtttga acagtattc tactccgatc    1560 tagaacgaat gaacgaccgc ccaaccacac cacatcatca caaccaagcg aacaaaagca   1620
tctctgtata tgcatcagta aaacccgcat caacatgtat acctatccta gatcgatatt   1680
tccatccatc atcttcaatt cgtaactatg aatatgtatg gcacacacat acagatccaa   1740
aattaataaa tccaccaggt agtttgaaac agaattctac tccgatctag aacgaccgcc   1800
caaccagacc acatcatcac aaccaagaca aaaaaagca tgaaaagatg acccgacaaa    1860
caagtgcacg gcatatattg aaataaagga aagggcaaa ccaaacccta tgcaacgaaa    1920 caaaaaaat catgaaatcg atcccgtctg cggaacggct agagccatcc caggattccc    1980
caaagagaaa cactggcaag ttagcaatca gaacgtgtct gacgtacagg tcgcatccgt   2040
gtacgaacgc tagcagcacg gatctaacac aaacacggat ctaacacaaa catgaacaga   2100
agtagaacta ccgggcccta accatggacc ggaacgccga tctagagaag gtagagaggg   2160 gggggagga cgagcggcgt accttgaagc ggaggtgccg acgggtggat ttgggggaga   2220
tccactagtt ctagagcggc cgccaccgcg gtggaattct cgaggtcctc tccaaatgaa   2280
atgaacttcc ttatatagag gaagggtctt gcgaaggata gtgggattgt gcgtcatccc   2340
ttacgtcagt ggagatatca catcaatcca cttgctttga agacgtggtt ggaacgtctt   2400 cttttccac gatgctcctc gtgggtgggg gtccatcttt gggaccactg tcggcagagg    2460
catcttgaac gatagccttt cctttatcgc aatgatggca tttgtaggtg ccaccttcct   2520
tttctactgt ccttttgatc aagtgaccga tagctgggca atggaatccg aggaggtttc   2580
ccgatattac cctttgttga aaagtctcaa tagccctttg gtcttctgag actgtatctt   2640
tgatattctt ggagtagacg agagtgtcgt gctccaccat gttatcacat caattcactt   2700
gctttgaaga cgtggttgga acgtcttctt tttccacgat gctcctcgtg ggtggggtc    2760 catctttggg accactgtcg gcagaggcat cttgaacgat agcctttcct ttatcgcaat   2820
gatggcattt gtaggtgcca ccttcctttt ctactgtcct tttgatcaag tgacagatag   2880
ctgggcaatg gaatccgagg aggtttcccg atattaccct ttgttgaaaa gtctcaatag   2940
ccctttggtc ttctgagacc tgcaggcatg caagcttgaa ttcctgcagc ccggggatc    3000 cactagtaag gccttaaggg ccagatcttg ggcccggtac ccgatcagat tgtcgtttcc   3060
```

```
cgccttcggt ttaaactatc agtgtttgac aggatatatt ggcgggtaaa cctaagagaa    3120
aagagcgttt attagaataa tcggatattt aaaagggcgt gaaaaggttt atccgttcgt    3180
ccatttgtat gtgcatgcca accacagggt tcccctcggg agtgcttggc attccgtgcg    3240
ataatgactt ctgttcaacc acccaaacgt cggaaagcct gacgacgag cagcattcca     3300
aaaagatccc ttggctcgtc tgggtcggct agaaggtcga gtgggctgct gtggcttgat    3360
ccctcaacgc ggtcgcggac gtagcgcagc gccgaaaaat cctcgatcgc aaatccgacg    3420
ctgtcgaaaa gcgtgatctg cttgtcgctc tttcggccga cgtcctggcc agtcatcacg    3480
cgccaaagtt ccgtcacagg atgatctggc gcgagttgct ggatctcgcc ttcaatccgg    3540
gtctgtggcg ggaactccac gaaaatatcc gaacgcagca agatatcgcg gtgcatctcg    3600
gtcttgcctg gcagtcgcc gccgacgccg ttgatgtgga cgccgaaaag gatctaggtg     3660
aagatccttt ttgataatct catgaccaaa atcccttaac gtgagttttc gttccactga    3720
gcgtcagacc ccgtagaaaa gatcaaagga tcttcttgag atcctttttt tctgcgcgta    3780
atctgctgct tgcaaacaaa aaaaccaccg ctaccagcgg tggtttgttt gccggatcaa    3840
gagctaccaa ctctttttcc gaaggtaact ggcttcagca gagcgcagat accaaatact    3900
gttcttctag tgtagccgta gttaggccac cacttcaaga actctgtagc accgcctaca    3960
tacctcgctc tgctaatcct gttaccagtg gctgctgcca gtggcgataa gtcgtgtctt    4020
accgggttgg actcaagacg atagttaccg gataagcgc agcggtcggg ctgaacgggg     4080
ggttcgtgca cacagcccag cttggagcga acgacctaca ccgaactgag atacctacag    4140
cgtgagctat gagaaagcgc cacgcttccc gaagggagaa aggcggacag gtatccggta    4200
agcggcaggg tcggaacagg agagcgcacg agggagcttc caggggggaaa cgcctggtat   4260
ctttatagtc ctgtcgggtt tcgccacctc tgacttgagc gtcgattttt gtgatgctcg    4320
tcagggggc ggagcctatg gaaaaacgcc agcaacgcgg ccttttacg gttcctggcc      4380
ttttgctggc cttttgctca catgttcttt cctgcgttat ccctgattc tgtggataac    4440
cgattaccgc ctttgagtga gctgataccg ctcgccgcag ccgaacgacc gagcgcagcg    4500
agtcagtgag cgaggaagcg gaagagcgcc tgatgcggta ttttctcctt acgcatctgt    4560
gcggtatttc acaccgcata tggtgcactc tcagtacaat ctgctctgat gccgcatagt    4620
taagccagta tacactccgc tatcgctacg tgactgggtc atggctgcgc ccgacaccc    4680
gccaacaccc gctgacgcgc cctgacgggc ttgtctgctc ccggcatccg cttacagaca    4740
agctgtgacc gtctccggga gctgcatgtg tcagaggttt tcaccgtcat caccgaaacg    4800
cgcgaggcag gggtacgtcg aggtcgatcc aacccctccg ctgctatagt gcagtcggct    4860
tctgacgttc agtgcagccg tcttctgaaa acgacatgtc gcacaagtcc taagttacgc    4920
gacaggctgc cgccctgccc tttcctggc gttttcttgt cgcgtgtttt agtcgcataa     4980
agtagaatac ttgcgactag aaccggagac attacgccat gaacaagagc gccgccgctg    5040
gcctgctggg ctatgcccgc gtcagcaccg acgaccagga cttgaccaac caacgggccc    5100
aactgcacgc ggccggctgc accaagctgt tttccgagaa gatcaccggc accaggcgcg    5160
accgccggga gctggccagg atgcttgacc acctacgccc tggcgacgtt gtgacagtga    5220
ccaggctaga ccgcctggcc cgcagcaccc gcgacctact ggacattgcc gagcgcatcc    5280
aggaggccgg cgcgggcctg cgtagcctgg cagagccgtg ggccgacacc accacgccgg    5340
ccggccgcat ggtgttgacc gtgttcgccg gcattgccga gttcgagcgt tccctaatca    5400
tcgaccgcac ccggagcggg cgcgaggccg ccaaggcgcg aggcgtgaag tttggccccc    5460
```

```
gccctaccct cacccccggca cagatcgcgc acgcccgcga gctgatcgac caggaaggcc    5520
gcaccgtgaa agaggcggct gcactgcttg gcgtgcatcg ctcgaccctg taccgcgcac    5580
ttgagcgcag cgaggaagtg acgcccaccg aggccaggcg gcgcggtgcc ttccgtgagg    5640
acgcattgac cgaggccgac gccctggcgg ccgccgagaa tgaacgccaa gaggaacaag    5700
catgaaaccg caccaggacg gccaggacga accgtttttc attaccgaag agatcgaggc    5760
ggagatgatc gcggccgggt acgtgttcga gccgcccgcg cacgtctcaa ccgtgcggct    5820
gcatgaaatc ctggccggtt tgtctgatgc caagctcgcg gcctggccgg cgagcttggc    5880
cgctgaagaa accgagcgcc gccgtctaaa aggtgatgt gtatttgagt aaaacagctt     5940
gcgtcatgcg gtcgctgcgt atatgatgcg atgagtaaat aaacaaatac gcaaggggaa    6000
cgcatgaagg ttatcgctgt acttaaccag aaaggcgggt caggcaagac gaccatcgca    6060
acccatctag cccgcgccct gcaactcgcc ggggccgatg ttctgttagt cgattccgat    6120
ccccagggca gtgcccgcga ttgggcggcc gtgcgggaag atcaaccgct aaccgttgtc    6180
ggcatcgacc gcccgacgat tgaccgcgac gtgaaggcca tcggccggcg cgacttcgta    6240
gtgatcgacg gagcgcccca ggcggcggac ttggctgtgt ccgcgatcaa ggcagccgac    6300
ttcgtgctga ttccggtgca gccaagccct tacgacatat gggccaccgc cgacctggtg    6360
gagctggtta agcagcgcat tgaggtcacg gatggaaggc tacaagcggc ctttgtcgtg    6420
tcgcgggcga tcaaaggcac gcgcatcggc ggtgaggttg ccgaggcgct ggccgggtac    6480
gagctgccca ttcttgagtc ccgtatcacg cagcgcgtga gctacccagg cactgccgcc    6540
gccggcacaa ccgttcttga atcagaaccc gagggcgacg ctgcccgcga ggtccaggcg    6600
ctggccgctg aaattaaatc aaaactcatt tgagttaatg aggtaaagag aaaatgagca    6660
aaagcacaaa cacgctaagt gccggccgtc cgagcgcacg cagcagcaag gctgcaacgt    6720
tggccagcct ggcagacacg ccagccatga agcgggtcaa ctttcagttg ccggcggagg    6780
atcacaccaa gctgaagatg tacgcggtac gccaaggcaa gaccattacc gagctgctat    6840
ctgaatacat cgcgcagcta ccagagtaaa tgagcaaatg aataaatgag tagatgaatt    6900
ttagcggcta aggaggcgg catggaaaat caagaacaac caggcaccga cgccgtggaa    6960
tgccccatgt gtggaggaac gggcggttgg ccaggcgtaa gcggctgggt tgtctgccgg    7020
ccctgcaatg gcactggaac cccccaagccc gaggaatcgg cgtgagcggt cgcaaaccat    7080
ccggcccggt acaaatcggc gcggcgctgg gtgatgacct ggtggagaag ttgaaggccg    7140
cgcaggccgc ccagcggcaa cgcatcgagg cagaagcacg ccccggtgaa tcgtggcaag    7200
cggccgctga tcgaatccgc aaagaatccc ggcaaccgcc ggcagccggt gcgccgtcga    7260
ttaggaagcc gcccaaggc gacgagcaac cagattttt cgttccgatg ctctatgacg    7320
tgggcacccg cgatagtcgc agcatcatgg acgtggccgt tttccgtctg tcgaagcgtg    7380
accgacgagc tggcgaggtg atccgctacg agcttccaga cgggcacgta gaggtttccg    7440
cagggccggc cggcatggcg agtgtgtggg attacgacct ggtactgatg gcggtttccc    7500
atctaaccga atccatgaac cgataccggg aagggaaggg agacaagccc ggccgcgtgt    7560
tccgtccaca cgttgcggac gtactcaagt tctgccggcg agccgatggc ggaaagcaga    7620
aagacgacct ggtagaaacc tgcattcggt taaacaccac gcacgttgcc atgcagcgta    7680
cgaagaaggc caagaacggc cgcctggtga cggtatccga gggtgaagcc ttgattagcc    7740
gctacaagat cgtaaagagc gaaaccgggc ggccggagta catcgagatc gagctagctg    7800
```

-continued

```
attggatgta ccgcgagatc acagaaggca agaacccgga cgtgctgacg gttcaccccg   7860
attacttttt gatcgatccc ggcatcggcc gttttctcta ccgcctggca cgccgcgccg   7920
caggcaaggc agaagccaga tggttgttca agacgatcta cgaacgcagt ggcagcgccg   7980
gagagttcaa gaagttctgt ttcaccgtgc gcaagctgat cgggtcaaat gacctgccgg   8040
agtacgattt gaaggaggag gcggggcagg ctggcccgat cctagtcatg cgctaccgca   8100
acctgatcga gggcgaagca tccgccggtt cctaatgtac ggagcagatg ctagggcaaa   8160
ttgccctagc aggggaaaaa ggtcgaaaag gtctctttcc tgtggatagc acgtacattg   8220
ggaacccaaa gccgtacatt gggaaccgga acccgtacat tgggaaccca agccgtaca    8280
ttgggaaccg gtcacacatg taagtgactg atataaaaga gaaaaaggc gattttccg     8340
cctaaaactc tttaaaactt attaaaactc ttaaaacccg cctggcctgt gcataactgt   8400
ctggccagcg cacagccgaa gagctgcaaa aagcgcctac ccttcggtcg ctgcgctccc   8460
tacgccccgc cgcttcgcgt cggcctatcg cggccgctgg ccgctcaaaa atggctggcc   8520
tacggccagg caatctacca gggcgcggac aagccgcgcc gtcgccactc gaccgccggc   8580
gcccacatca aggcaccggt gggtatgcct gacgatgcgt ggagaccgaa accttgcgct   8640
cgttcgccag ccaggacaga aatgcctcga cttcgctgct gcccaaggtt gccgggtgac   8700
gcacaccgtg gaaacggatg aaggcacgaa cccagtggac ataagcctgt tcggttcgta   8760
agctgtaatg caagtagcgt atgcgctcac gcaactggtc cagaaccttg accgaacgca   8820
gcggtggtaa cggcgcagtg gcggttttca tggcttgtta tgactgtttt tttggggtac   8880
agtctatgcc tcgggcatcc aagcagcaag cgcgttacgc cgtgggtcga tgtttgatgt   8940
tatggagcag caacgatgtt acgcagcagg gcagtcgccc taaaacaaag ttaaacatca   9000
tgagggaagc ggtgatcgcc gaagtatcga ctcaactatc agaggtagtt ggcgtcatcg   9060
agcgccatct cgaaccgacg ttgctggccg tacatttgta cggctccgca gtggatggcg   9120
gcctgaagcc acacagtgat attgatttgc tggttacggt gaccgtaagg cttgatgaaa   9180
caacgcggcg agctttgatc aacgaccttt tggaaacttc ggcttcccct ggagagagcg   9240
agattctccg cgctgtagaa gtcaccattg ttgtgcacga cgacatcatt ccgtggcgtt   9300
atccagctaa gcgcgaactg caatttggag aatggcagcg caatgacatt cttgcaggta   9360
tcttcgagcc agccacgatc gacattgatc tggctatctt gctgacaaaa gcaagagaac   9420
atagcgttgc cttggtaggt ccagcggcgg aggaactctt tgatccggtt cctgaacagg   9480
atctatttga ggcgctaaat gaaaccttaa cgctatggaa ctcgccgccc gactgggctg   9540
gcgatgagcg aaatgtagtg cttacgttgt cccgcatttg gtacagcgca gtaaccggca   9600
aaatcgcgcc gaaggatgtc gctgccgact gggcaatgga gcgcctgccg gcccagtatc   9660
agcccgtcat acttgaagct agacaggctt atcttggaca agaagaagat cgcttggcct   9720
cgcgcgcaga tcagttggaa gaatttgtcc actacgtgaa aggcgagatc accaaggtag   9780
tcggcaaata atgtctaaca attcgttcaa gccgacgccg cttcgcggcg cggcttaact   9840
caagcgttag atgcactaag cacataattg ctcacagcca aactatcagg tcaagtctgc   9900
ttttattatt tttaagcgtg cataataagc cctacacaaa ttgggagata tatcatgaaa   9960
ggctggcttt ttcttgttat cgcaatagtt ggcgaagtaa tcgcaacata gcttgcttgg  10020
tcgttccgcg tgaacgtcgg ctcgattgta cctgcgttca aatactttgc gatcgtgttg  10080
cgcgcctgcc cggtgcgtcg gctgatctca cggatcgact gcttctctcg caacgccatc  10140
cgacggatga tgtttaaaag tcccatgtgg atcactccgt tgccccgtcg ctcaccgtgt  10200
```

```
tgggggaag gtgcacatgg ctcagttctc aatggaaatt atctgcctaa ccggctcagt    10260
tctgcgtaga aaccaacatg caagctccac cgggtgcaaa gcggcagcgg cggcaggata    10320
tattcaattg taaatggctt catgtccggg aaatctacat ggatcagcaa tgagtatgat    10380
ggtcaatatg gagaaaaaga aagagtaatt accaattttt tttcaattca aaaatgtaga    10440
tgtccgcagc gttattataa aatgaaagta cattttgata aaacgacaaa ttacgatccg    10500
tcgtatttat aggcgaaagc aataaacaaa ttattctaat tcggaaatct ttatttcgac    10560
gtgtctacat tcacgtccaa atgggggctt agatgagaaa cttcacgatc ggctctagta    10620
gtctgcagtg cagcgtgacc cggtcgtgcc cctctctaga gataatgagc attgcatgtc    10680
taagttataa aaaattacca catattttt ttgtcacact tgtttgaagt gcagtttatc     10740
tatctttata catatattta aactttactc tacgaataat ataatctata gtactacaat    10800
aatatcagtg ttttagagaa tcatataaat gaacagttag acatggtcta aaggacaatt    10860
gagtattttg acaacaggac tctacagttt tatcttttta gtgtgcatgt gttctccttt    10920 tttttgcaa atagcttcac ctatataata cttcatccat tttattagta catccattta     10980
gggtttaggg ttaatggttt ttatagacta attttttag tacatctatt ttattctatt     11040
ttagcctcta aattaagaaa actaaaactc tattttagtt tttttattta ataatttaga    11100
tataaaatag aataaaataa agtgactaaa aattaaacaa ataccctta agaaattaaa     11160 aaaactaagg aaacattttt cttgtttcga gtagataatg ccagcctgtt aaacgccgtc    11220
gatcgacgag tctaacggac accaaccagc gaaccagcag cgtcgcgtcg ggccaagcga    11280
agcagacggc acggcatctc tgtcgctgcc tctggacccc tctcgagagt tccgctccac    11340
cgttggactt gctccgctgt cggcatccag aaattgcgtg gcggagcggc agacgtgagc    11400
cggcacggca ggcggcctcc tcctcctctc acggcaccgg cagctacggg ggattccttt    11460
cccaccgctc cttcgctttc ccttcctcgc ccgccgtaat aaatagacac ccctccaca    11520 ccctctttcc ccaacctcgt gttgttcgga gcgcacacac acacaaccag atctcccca    11580 aatccacccg tcggcacctc cgcttcaagg tacgccgctc gtcctccccc ccccccctc    11640 tctaccttct ctagatcggc gttccggtcc atggttaggg cccggtagtt ctacttctgt    11700
tcatgtttgt gttagatccg tgtttgtgtt agatccgtgc tgctagcgtt cgtacacgga    11760
tgcgacctgt acgtcagaca cgttctgatt gctaacttgc cagtgtttct ctttggggaa    11820
tcctgggatg gctctagccg ttccgcagac gggatcgatc taggataggt atacatgttg    11880
atgtgggttt tactgatgca tatacatgat ggcatatgca gcatctattc atatgctcta    11940
accttgagta cctatctatt ataataaaca agtatgtttt ataattattt tgatcttgat    12000
atacttggat gatggcatat gcagcagcta tatgtggatt ttttagccc tgccttcata     12060 cgctatttat ttgcttggta ctgtttctt tgtcgatgct caccctgttg tttggtgtta     12120
cttctgcagg tcgagtggcc accatgggcc cagaacgacg cccggccgac atccgccgtg    12180
ccaccgaggc ggacatgccg gcggtctgca ccatcgtcaa ccactacatc gagacaagca    12240
cggtcaactt ccgtaccgag ccgcaggaac cgcaggagtg gacggacgac ctcgtccgtc    12300
tgcgggagcg ctatccctgg ctcgtcgccg aggtggacgg cgaggtcgcc ggcatcgcct    12360
acgcgggccc ctggaaggca cgcaacgcct acgactggac ggccgagtcg accgtgtacg    12420
tctccccccg ccaccagcgg acgggactgg gctccacgct ctacacccac ctgctgaagt    12480
ccctggaggc acagggcttc aagagcgtgg tcgctgtcat cgggctgccc aacgacccga    12540
```

-continued

```
gcgtgcgcat gcacgaggcg ctcggatatg cccccgcgg catgctgcgg gcggccggct    12600
tcaagcacgg gaactggcat gacgtgggtt tctggcagct ggacttcagc ctgccggtac    12660
cgccccgtcc ggtcctgccc gtcaccgaga tctgagatca cgcgttctag tccgcaaaaa    12720
tcaccagtct ctctctacaa atctatctct ctctattttt ctccagaata atgtgtgagt    12780
agttcccaga taagggaatt agggttctta tagggtttcg ctcatgtgtt gagcatataa    12840
gaaaccctta gtatgtattt gtatttgtaa aatacttcta tcaataaaat ttctaattcc    12900
taaaaccaaa atccagtgac ctgcaggcat gcaagctgat ccactagagg ccatgg        12956
```

METHOD FOR GENE OPTIMIZATION

Low transgene protein expression in transgenic plants can be attributable to several factors (see Lu et al (2015) for a review). These include:
- low levels of transcription, attributable to linkage of genes to weak promoters.
- aberrant processing of transcripts including mis-splicing and premature polyadenylation giving a transcript that lacks parts of the coding region.
- low translational initiation caused by ATG initiation codons upstream of the start point and poor accessibility of the ribosome to the correct initiation site.
- low translation rates due to presence of rarely used codons in the coding region.
- post-transcriptional factors such as RNA stability, protein modifications and protein stability.

Often transgenes to be expressed in plants are derived from other plant species or non-plants. These genes are evolutionary adapted for expression in their host organism at the desired expression level in the host organism, but may be not adapted for expression in the transformed plant. Additionally some genes from the same plant as the plant to be transformed may not be adapted for high-level expression in that same plant. Different organisms have different DNA base compositions (AT % or GC %) as do different genomes within an eukaryotic cell (nucleus versus mitochondria (with also T to U) and in plant cells (plastids)). This difference in DNA base pair composition affects the frequency of the occurrence of degenerate codons coding for the same amino-acid (codon use frequency). The abundance of the cognate charged tRNAs is generally proportional to the frequency of the target codons in the genome. Thus for example genes that are rich in AT % are poorly translated in organisms that are GC % rich due to a lack of certain charged tRNAs. It is well known in the art that this problem can be overcome by recoding transgenes such that the codon usage reflects that used in the transgenic organism and if high expression is required, match the codon usage to that of highly expressed genes in that organism.

In addition to the question of codon-usage eukaryotic nuclear genes have transcript splicing and polyadenylation signals that may differ between eukaryotic organisms (eg between plants animals and insects or between dicotyledonous and monocotyledonous plants) and that may be absent in other organisms such as prokaryotes. Expression of a gene from exogenous species in a transgenic plant may thus lead to unwanted transcript processing such as mis-splicing and premature polyadenylation. In animals the polyadenylation signal has been found to be composed of 2 major elements, the AAUAAA motif positioning element (PE) located 10 to 30 bp upstream of the polyadenylation site (cleavage site (CS)) and a U or UG rich downstream element (DE) downstream of the CS (Colgan and Manley (1997)) Efforts have been made to identify DNA sequences that act as polyadenylation signals in plants. Joshi (1987) analysed 4 domains downstream of the coding region in 46 plant genomic sequences and identified putative consensus sequences upstream and downstream of the AAUAAA like motif. Graber et al (1999) compared polyadenylation signals in silico in yeast, *Arabidopsis*, rice, fruitfly, mouse and humans. They concluded that the use and conservation of the AAUAAA sequence varied between the 6 species with this signal being particularly weak in plants and yeast. They favoured a model where the polyadenylation signal consists of a series of elements where no one element is universally required. A lack of one element could be compensated by the presence of strong words in other elements. Graber et al (1999) proposed 5 sequence elements for plants, in order; the Upstream element (UE) (UUGUAU or UUGUAA), the PE (AAUAAA or AAUGAA=A rich), the U-rich (UUUUCU or UUUUUU or similar) the CS (UA or UC) and a second U-rich region. Thus plants in comparison to animals have an additional upstream element that contributes to the definition of the polyadenylation signal. Mogen et al. (1990) reported that deletions of upstream elements of the Cauliflower Mosaic Virus (CaMV) and the PeaRbsC polyadenylation regions reduced the efficiency of polyadenylation at the 'correct' site. A similar result was also reported by Sanfacon et al (2007), again on the CaMV polyadenylation signal.

Since the polyadenylation signals in plants are AT-rich and that prokaryotes lack these signals, genes from prokaryotes which are AT % rich frequently contain sequences that might be recognised as polyadenylation sequences. Thus presence of such 'cryptic' polyadenylation motifs in coding regions of transgenes has been attributed to poor expression of genes such as *Bacillus thuringiensis* genes in plants. Fischhoff et al (U.S. Pat. No. 7,741,118 B1) describes that removal of hexamer AATAAA-like motifs will improve gene expression. They provide a list of 16 potential polyadenylation motifs that should be reduced in frequency in the coding region of a transgene to improve expression in planta.

High-level expression of non-plant genes in plant is a critical agronomic issue. Therefore, there is a need to develop new methods to improve gene expression in plants notably by the provided method that introduces fewer modifications than proposed by some other gene modification methods known in the art.

DESCRIPTION OF THE INVENTION

The purpose of the invention is to provide a method for modifying a coding gene sequence, in particular when this coding gene sequence encodes a *Bacillus thuringiensis* insecticidal protein, in order to obtain in planta expression of the protein at a level significantly higher than the wild type gene sequence.

Another purpose of the invention is to provide a method for preparing a DNA construct comprising a modified gene sequence wherein the modified gene sequence is expressed at a level significantly higher than the wild type gene sequence in planta.

The present invention relates to a method of making a modified coding sequence encoding a non-plant protein, the method comprising:
  a) identifying a coding sequence that encodes a non-plant protein;
  b) identifying each polyadenylation motif sequence and its nucleic acid position in said coding sequence;
  c) optimizing said coding sequence by codon substitution wherein the optimized coding sequence encodes for said non-plant protein; and
  d) modifying said optimized coding sequence to obtain a modified gene sequence by introducing at least one polyadenylation motif sequence, as depicted in Table 1, in the optimized gene sequence, wherein the modified coding sequence comprises at least one polyadenylation motif and said modified coding sequence is encoding said non-plant protein.

The invention also relates to a method of modifying a coding sequence encoding a non-plant protein, comprising the steps of:
a) identifying each wild-type polyadenylation motif sequence and its position within said coding sequence;
b) optimizing said coding sequence by codon substitution, thereby obtaining an optimized coding sequence which encodes said non-plant protein; and
c) introducing at least one polyadenylation motif sequence as disclosed in Table 1 within said optimized gene sequence, thereby obtaining a modified coding sequence which comprises at least one polyadenylation motif and said modified coding sequence is encoding said non-plant protein.

In a preferred embodiment, and as disclosed below, the polyadenylation that is introduced in the optimized gene sequence is preferentially a weak polyadenylation motif, as defined below.

Furthermore, no strong polyadenylation, as defined below, is introduced in the optimized gene sequence.

Furthermore, the number of polyadenylation motif sequences introduced in the optimized gene sequence is such that the total number of polyadenylation motif sequences in the modified sequence is three or higher, but less than the number of polyadenylation motif sequence that were present in the wild-type sequence.

As will be described below, the modified sequence will thus contain a combination of at least three polyadenylation, identical to a polyadenylation combination that is present in the wild-type sequence, and the modified sequence will not comprise the combination of the totality of the polyadenylation motifs that are present in the wild-type sequence.

The purpose of the modification of the optimized gene sequence by reintroduction of polyadenylation motifs, as described herein, is that this would either improve or maintain expression of the sequence, as compared to the optimized sequence. The examples show, however, that re-introduction of polyadenylation motifs in the optimized sequence in order to obtain a modified sequence comprising all the polyadenylation motifs as present in the wild-type sequence may, in some instances, decrease the expression with regards to the optimized sequence. Introducing only some polyadenylation motifs, in particular the weak ones, in order to have at least 3 (and preferably at most 10 or at most 6) polyadenylation motifs in the modified sequence, but not all polyadenylation motifs shall thus make it possible to have a robust method that can be applicable to and repeated with virtually any sequence.

In this embodiment, the invention thus relates to a method of making a modified coding sequence encoding a non-plant protein, the method comprising:
a) identifying a coding sequence that encodes a non-plant protein;
b) identifying each polyadenylation motif sequence and its nucleic acid position in said coding sequence;
c) optimizing said coding sequence by codon substitution wherein the optimized coding sequence encodes for said non-plant protein; and
d) modifying said optimized coding sequence to obtain a modified gene sequence as disclosed in Table 1 by introducing at least one polyadenylation motif sequence in the optimized gene sequence, so as to obtain a modified coding sequence that comprises at least three polyadenylation motifs, but not all the polyadenylation motifs identified in step b), and said modified coding sequence is encoding said non-plant protein.

Likewise, the invention also relates to a method of modifying a coding sequence encoding a non-plant protein, comprising the steps of:
a) identifying each wild-type polyadenylation motif sequence and its position within said coding sequence;
b) optimizing said coding sequence by codon substitution, thereby obtaining an optimized coding sequence which encodes said non-plant protein; and
c) introducing at least one polyadenylation motif sequence as disclosed in Table 1 within said optimized gene sequence, so as to obtain a modified coding sequence that comprises at least three polyadenylation motifs, but not all the polyadenylation motifs identified in step a), and said modified coding sequence is encoding said non-plant protein.

These methods are preferably performed with one or more of the following characteristics, that can be implemented independently or through any combination:
the polyadenylation motif sequence introduced in step d) (or c) is not a strong polyadenylation motif sequence (as described below)
the polyadenylation motif sequence introduced in step d) (or c) is a weak polyadenylation motif sequence (as described below)
the polyadenylation motif sequence is one that has been identified in step b) and is reintroduced at its position identified in step b) (or a)
the modified sequence contains at most 6 polyadenylation motif sequences
the modified sequence contains at most 10 polyadenylation motif sequences.
All of the at least 3 polyadenylation motif sequences in the modified sequence were initially present in the wild-type sequence and are localized at the location they had in the wild-type sequence.

In a preferred embodiment, said polyadenylation motif sequence introduced within said optimized gene sequence has been identified in step a), and in this case, it is further preferred when said polyadenylation motif sequence identified in step a) is introduced at its position within said optimized gene sequence.

In a further embodiment, when more than one polyadenylation motif is introduced within the optimized sequence, each polyadenylation motif introduced within said optimized sequence is a wild-type polyadenylation motif identified in step a), which is introduced at a nucleic acid position corresponding to its position within the coding sequence.

The present invention encompasses the identification of a coding gene sequence. This coding gene sequence is the wild-type coding sequence which is isolated or identified from the organism where the protein is naturally expressed.

Specifically, the invention encompasses the use of exogenous coding sequences encoding non-plant proteins. Preferably, the non-plant protein is an insecticidal protein encoded by *Bacillus thuringiensis*.

The coding gene sequence can be a fragment of the wild-type coding gene sequence. For example, the coding gene sequence can be a sequence encoding for the toxin fragment of a *Bacillus thuringiensis* protein. Also the coding sequence can encode for a fusion between two protein fragments obtained from different wild-type proteins.

Where appropriate, the coding sequence may be optimized for increased expression in the transformed plant. There are a number of optimizations that can be performed at the DNA level, without changing the protein sequence, by conservative codon exchanges which replace one codon by another codon encoding the same amino acid.

The parameters that can be optimized are for example, codon usage, local GC content, absence of splice sites, mRNA secondary structure, polyadenylation motifs.

More specifically, the genes can be synthesized using plant-preferred codons for improved expression, or may be synthesized using codons at a plant-preferred codon usage frequency. As a consequence, the GC content of the gene will often be increased. Methods to achieve such optimization for expression are well known in the art and are notably described in Campbell and Gowri (1990) for a discussion of host-preferred codon usage and more specifically for synthesizing plant-preferred genes (WO91/16432, and Murray et al. (1989)). WO 91/16432 describes in particular a process for modifying a Bt ICP gene to improve its expression in a plant cell, transformed with the gene; the process comprising the step of: changing A and T sequences in a plurality of translational codons of the gene to corresponding G and C sequences encoding the same amino acids, so as to improve the gene's transcription to an mRNA, the nuclear accumulation of the mRNA and/or the nuclear export of the mRNA, particularly the gene's transcription, in the plant cell.

In order to perform such optimization, different algorithms are available to predict the position of polyadenylation motifs in plant genes. For example, Ji et al (2015) have developed the algorithm PASPA (PolyA Site Prediction in Plants and Algae; http://bmi.xmu.edu.cn/paspa). Other algorithms are also available like PAC (poly(A) site classifier (Wu et al 2012) and polyA-iEP (Tzanis et al (2011). The baseline of this system is that motifs are identified with a given level of probability to represent a polyadenylation motif. The polyadenylation motifs harboring a high level of probability to represent a polyadenylation sites in the wild type sequence can then be removed from the optimized sequence.

It is intended here that polyadenylation motifs in the present invention consist of the following 16 motif sequences: AAAATA, AACCAA, AAGCAT, AATAAA, AATAAT, AATACA, AATCAA, AATTAA, ATAAAA, ATACAT, ATACTA, ATATAA, ATGAAA, ATTAAA, ATTAAT and CATAAA. Each polyadenylation motif can be referred by a specific sequence as described by the polyA code in Table 1. Furthermore, each polyadenylation motif comprised in a coding sequence can be characterized not only by its sequence but also by its nucleic acid position in the coding sequence, for instance "located between nucleotide X and nucleotide Y of the coding sequence", or "whereas the first nucleotide of the polyadenylation motif is located at position X within the coding sequence".

Consequently, a coding sequence encoding for a non-plant protein can be characterized by a combination of polyadenylation motifs wherein a polyA sequence and a nucleic acid position within the coding sequence can be assigned to each polyadenylation motif identified in the coding sequence.

Optimization of a coding sequence by the methods described above can lead to the removal of one or more polyadenylation motifs as listed in Table 1. To some extent, all the polyadenylation motifs can be removed so that the optimized coding sequence is free of any polyadenylation motifs. However, complete removal of polyadenylation motifs can impose great constraints on other sequence variables, notably on the amino acid sequence (i.e. a loss of identity of the protein obtained from the optimized sequence with regards to the wild-type protein obtained from the non-optimized wild-type sequence).

The applicant has shown that surprisingly, it is possible to reintroduce polyadenylation motifs in the optimized gene sequence and that one will still observe a reduction in the level of polyadenylation motifs initially calculated and predicted from the wild type sequence for most of the polyadenylation motifs.

Without being bound by this theory of the mechanism sustaining this phenomenon, the inventors suppose that the optimization of the coding gene sequence is modifying the surrounding motifs acting in combination with polyadenylation motifs to reduce gene expression so that when the polyadenylation motifs are reintroduced in the optimized coding gene sequence, they lose their ability to reduce gene expression.

It is to be noted that the polyadenylation site(s) that is (are) introduced within the optimized sequence was (were) not necessarily present in the wild-type sequence. Furthermore, such site(s) is (are) not necessarily introduced at the same location of the wild-type polyadenylation sites in the wild-type sequence.

The person skilled in the art can determine which and how many polyadenylation motifs with a specific polyA code can introduced in the optimized coding sequence to perform the invention, while maintaining the wild type protein sequence.

In a preferred embodiment, each polyadenylation motif that is introduced in the optimized coding sequence is introduced at a nucleic acid position identical to a wild-type polyadenylation site position as identified in the wild type coding sequence. In a most preferred embodiment, the polyadenylation motif that is introduced within the optimized sequence is the wild-type polyadenylation motif, introduced at its natural (wild-type) position.

In these two embodiments, the protein encoded by the modified coding sequence is the wild-type protein, encoded by the wild-type, non-optimized sequence.

Most preferably, the method of the invention relates to a method of modifying a coding sequence wherein all the introduced polyadenylation motifs are introduced at a nucleic acid position identical to their positions as identified in the wild type coding sequence and wherein the resulting modified coding sequence comprises the same combination of polyadenylation motifs as identified in the wild type coding sequence.

In this embodiment, wild-type polyadenylation motifs as identified within the coding sequence are introduced at nucleic acid positions identical to their positions within the coding sequence, so as to obtain a modified coding sequence comprising the same combination of polyadenylation motifs as the wild type coding sequence.

Such a modified sequence is encoding the wild-type non-plant protein and is able to be expressed at a level significantly higher compared with the non-optimized wild-type sequence even though it comprises all the polyadenylation motifs as present in the wild-type coding sequence.

The method of the invention also relates to a method of modifying a coding sequence wherein all the introduced polyadenylation motifs are introduced at a nucleic acid position identical to their position as identified in the wild type coding sequence, the resulting modified coding sequence shall thus comprise a combination of one, two, or three polyadenylation motifs as identified in the wild type coding sequence. In such cases, the modified coding sequence is expected to not comprise the combination of all the polyadenylation motifs as identified in the wild-type coding sequence.

In a specific embodiment, wild-type polyadenylation motifs as identified within the coding sequence are introduced in step c) at nucleic acid position identical to their position within the coding sequence, so as to obtain a modified coding sequence comprising one polyadenylation motif present in the wild type sequence.

In another embodiment, wild-type polyadenylation motifs as identified within the coding sequence are introduced in step c) at nucleic acid position identical to their position within the coding sequence, so as to obtain a modified coding sequence comprising a combination of two polyadenylation motifs present in the wild type sequence.

It is to be noted that, in order to obtain a modified coding sequence comprising a combination of two polyadenylation motifs present in the wild type sequence, one will introduce one or two polyadenylation motifs present in the wild type sequence within the optimized sequence, depending on whether said optimized sequence already comprises one or zero of such polyadenylation motifs present in the wild type sequence.

In another embodiment, wild-type polyadenylation motifs as identified within the coding sequence are introduced in step c) at nucleic acid position identical to their position within the coding sequence, so as to obtain a modified coding sequence comprising a combination of three polyadenylation motifs present in the wild type sequence.

It is to be noted that, in order to obtain a modified coding sequence comprising a combination of three polyadenylation motifs present in the wild type sequence, one will introduce one, two or three polyadenylation motifs present in the wild type sequence within the optimized sequence, depending on whether said optimized sequence already comprises two, one or zero of such polyadenylation motifs present in the wild type sequence.

It is expected that polyadenylation motifs have different effects on the level of gene expression whatever the gene sequence considered. Polyadenylation motifs can be featured as strong or weak motifs. Weak motifs are expected to be more tolerated for the expression of the coding gene sequence than strong motifs. Advantageously, the polyadenylation motifs introduced in the optimized gene sequence are the polyadenylation motifs identified as weak motifs.

Polyadenylation motifs have been ranked from the weakest to the strongest regarding their occurrence in maize coding gene sequences and regarding their occurrence in optimized gene sequences shown to be well expressed in plants.

Preferably the weak polyadenylation motifs are chosen amongst the AAAATA, AAGCAT, AATCAA, and ATGAAA sequences. The strong motifs are chosen amongst the AATTAA, ATACAT, ATACTA, ATATAA, ATTAAA, ATTAAT and CATAAA sequences.

More preferably, the rank amongst the weak polyadenylation motifs are from the weaker to the less weak: ATGAAA, AATCAA, AAAATA and AAGCAT. The rank amongst the strong polyadenylation motifs are from the stronger to the less strong: ATACTA, ATTAAT, AATTAA, ATTAAA, CATAAA, ATATAA, ATACAT.

Most preferably, the rank from the weaker to the stronger polyadenylation motifs is provided in Table 1.

Upon comparison of the coding gene sequences from monocotyledons and dicotyledons, one can note that the common strongest polyadenylation motifs are the AATTAA, ATACTA, ATATAA, ATTAAA, ATTAAT and CATAAA motifs.

Another weak polyadenylation motif (poladenylation motif AACCAA) can also be identified.

In one embodiment of the invention, none of the strongest polyadenylation motifs AATTAA, ATACTA, ATATAA, ATTAAA, ATTAAT and CATAAA are added in the optimized sequence. It is, however, to be noted that the modified sequence may contain one (or more of these polyadenylation motifs, if they are present in the optimized sequence, after the native (wild-type) sequence has been optimized by codon substitution)

Most preferably, the polyadenylation motifs that are added to the optimized sequence are chosen in the group consisting of ATGAAA, AATCAA, AAAATA, AACCAA and AAGCAT. Consequently only these weak polyadenylation motifs are added in the optimized sequence.

In a further embodiment of the invention, the final modified sequence comprises a total of three to a few more polyadenylation motifs wherein at least three polyadenylation motifs are corresponding to a combination of three polyadenylation motifs identified in the wild-type coding sequence, and wherein the modified coding sequence does not comprise all the polyadenylation motifs identified and present in the wild-type coding sequence.

Preferably, the modified optimized sequence comprises three to ten polyadenylation motifs.

Preferably, the modified optimized sequence comprises three to six polyadenylation motifs.

The step of reintroducing polyadenylation motifs might create changes in the amino acid at the edges of the polyadenylation motifs.

It can also create additional motifs that might reduce gene expression. Additional motifs can include for example cryptic splice sites GGTAAG, GGTGAT, GTAAAA and GTAAGT and/or polyA or polyT and/or repeats of 7 or more base pairs.

The present method may thus comprises further steps of modifications of the modified gene sequence in order to make sure that the protein sequence encoded by the modified sequence is identical to the one coded by the wild-type coding gene sequence. The person skilled in the art knows the different type of motifs to be checked and, when appropriate, will modify the modified gene sequence so that the function of the protein encoded by the modified coding gene sequence is not altered compared to the function of the protein encoded by the wild type coding sequence. More preferably, the amino-acid sequence of the protein encoded by the modified coding gene sequence is identical to the amino-acid sequence of the protein encoded by the wild type coding sequence.

The present invention encompasses a modified coding sequence obtainable according to the method of making a modified coding sequence wherein polyadenylation motifs are introduced at a nucleic acid position identical to their position as identified in the wild type coding sequence and wherein the resulting modified coding sequence comprises the same combination of polyadenylation motifs as identified in the wild-type coding sequence.

It is intended in the present invention that all the steps of the method of making a modified coding sequence can be made by combining in silico sequence designing with the preparation of synthetic coding gene sequence. Most preferably, all the steps of the methods described above can be made in silico. Therefore, in such a case, the method of making an expression cassette as described below will require as a first step the synthesis of the corresponding modified coding gene sequence.

The invention thus encompasses a method making a nucleic acid molecule, comprising the steps of performing the methods as disclosed above and synthetizing the modified nucleic acid harboring the modified sequence as obtained.

Another embodiment of the invention is a method of making an expression cassette comprising a modified coding sequence encoding for a non-plant protein, the method comprising the steps of making a modified coding sequence encoding for said protein according to any method as described above and operably linking a promoter and a terminator to said modified coding sequence to obtain a construct for expression in plant.

More specifically, the invention relates to a method of making an expression cassette wherein polyadenylation motifs are introduced at a nucleic acid position identical to their position as identified in the wild type coding sequence and wherein the resulting modified coding sequence comprises the same combination of polyadenylation motifs as identified in the wild type coding sequence.

These cassettes may be obtained in silico or actually synthetized.

More preferably, the coding sequence is encoding a *Bacillus thuringiensis* insecticidal protein.

The term "operably linked" as used herein means that the promoter and the modified coding gene sequence are oriented such that the promoter directs expression of the coding sequence, generally in the 5' to 3' direction.

The constructs may also contain enhancers (such as introns) and terminators at the 3' end of the coding sequence.

A promoter "active in plants" is a promoter that is able to drive expression of a gene operably linked thereto in a plant cell.

For being expressed, a coding sequence may be present under the control of a constitutive, tissue specific, developmentally regulated or inducible promoter.

Promoters may come from the same species or from another species (heterologous promoters). Although some promoters may have the same pattern of regulation when they are used in different species, it is often preferable to use monocotyledonous promoters in monocotyledons and dicotyledonous promoters in dicotyledonous plants.

In a preferred embodiment, said construct is under the control of a constitutive promoter.

Examples of constitutive promoters useful for expression include the 35S promoter or the 19S promoter (Kay et al., 1987, Science, 236:1299-1302), the rice actin promoter (McElroy et al., 1990, Plant Cell, 2:163-171), the pCRV promoter (Depigny-This et al., 1992, Plant Molecular Biology, 20:467-479), the CsVMV promoter (Verdaguer et al., 1998, Plant Mol Biol. 6:1129-39), the ubiquitin 1 promoter of maize (Christensen et al., 1996, Transgenic. Res., 5:213), the regulatory sequences of the T-DNA of *Agrobacterium tumefaciens*, including mannopine synthase, nopaline synthase, octopine synthase.

Other suitable promoters could be used. It could be an inducible promoter or a tissue-specific promoter such as, for example, a leaf-specific promoter or a seed-specific. Numerous tissue-specific promoters are described in the literature and any one of them can be used. One can cite the promoters disclosed in US 20130024998.

In one embodiment, the protein encoded by the modified coding sequence is targeted to the chloroplast for expression. In this manner, the expression cassette will additionally contain a nucleic acid encoding a transit peptide to direct the protein to the chloroplasts. Such transit peptides are known in the art. See, for example, Von Heijne et al. (1991) Plant Mol. Biol. Rep. 9:104-126; Clark et al. (1989) J. Biol. Chem. 264:17544-17550; Della-Cioppa et al. (1987) Plant Physiol. 84:965-968; Romer et al. (1993) Biochem. Biophys. Res. Commun. 196:1414-1421; and Shah et al. (1986) Science 233:478-481.

The invention also encompasses a vector containing the expression cassette (nucleic acid construct) of the invention.

A vector, such as a plasmid, can thus be used for transforming host cells. The construction of vectors for transformation of host cells is within the capability of one skilled in the art following standard techniques.

The decision as to whether to use a vector for transforming a cell, or which vector to use, is guided by the method of transformation selected, and by the host cell selected.

Possible vectors include the Ti plasmid vectors, shuttle vectors designed merely to maximally yield high numbers of copies, episomal vectors containing minimal sequences necessary for ultimate replication once transformation has occurred, transposon vectors, including the possibility of RNA forms of the gene sequences. The selection of vectors and methods to construct them are commonly known to persons of ordinary skill in the art and are described in general technical references (Mullis, K B (1987), Methods in Enzymology).

For transformation methods within a plant cell, one can cite methods of direct transfer of genes such as direct micro-injection into plant embryos, vacuum infiltration or electroporation, direct precipitation by means of PEG or the bombardment by gun of particles covered with the DNA of interest.

It is preferred to transform the plant cell with a bacterial strain, in particular *Agrobacterium*, in particular *Agrobacterium tumefaciens*. In particular, it is possible to use the method described by Ishida et al. (Nature Biotechnology, 14, 745-750, 1996) for the transformation of Monocotyledons.

The cell can be transformed by any transient expression system, some of which are well known from the person skilled in the art.

In a specific embodiment, said expression cassette is stably integrated within the genome of said host cell. This embodiment is particularly interesting for plant host cells. Stable integration within the genome means that the expression cassette can be transmitted to the progeny of said host cell upon division.

The invention also encompasses a plant containing at least one cell containing the expression cassette as defined above, preferably stably integrated within its genome.

A part of a transgenic plant, in particular fruit, seed, grain or pollen, comprising such a cell or generated from such a cell is also encompassed by the invention. The host cell as mentioned above, part of the invention, is also considered as being a part of a transgenic plant.

It is reminded that a whole plant can be regenerated from a single transformed plant cell. Thus, in a further aspect the present invention provides transgenic plants (or parts of them) including the expression cassette according to the invention. The regeneration can proceed by known methods.

The seeds which grow by fertilization from this plant, also contain this transgene in their genome.

Said plant or part of a plant according to the invention can be a plant or a part of it from various species, notably an *Angiosperm, Monocotyledons* as *Dicotyledons.*

Said plant is preferably selected from the group consisting of maize wheat, barley, rape, sugar beet and sunflower. In a preferred embodiment, said plant is maize.

DESCRIPTION OF THE FIGURES

FIG. 1A, FIG. 1B, and FIG. 1C illustrate the steps of various embodiments to perform a wild type gene modification to express the protein at high level in plant.

FIG. 2A, FIG. 2B, FIG. 2C, and FIG. 2D illustrate the application of the method on *Bacillus thuringiensis* Axmi028 coding sequence.

FIG. 3A, FIG. 3B, FIG. 3C, and FIG. 3D illustrate the PASPA results on Axmi028

FIG. 4A, FIG. 4B, FIG. 4C, and FIG. 4D illustrate the application of the method on *Bacillus thuringiensis* Axmi100 coding sequence.

FIG. 5A, FIG. 5B, FIG. 5C, and FIG. 5D illustrate the PASPA results on Axmi100

FIG. 6A and FIG. 6B show luciferase expression levels of the Axmi028-LUC fusions (FIG. 6A) and of the Axmi100-LUC fusions (FIG. 6B) in transient assays in maize leaves.

FIG. 7A and FIG. 7B show Western Blots analysis of independent Axmi028 maize transformants using a C Myc Tag antibody (FIG. 7A) and independent Axmi100 maize transformants using a polyclonal antibody (FIG. 7B). In FIG. 7A, lane 1, molecular size markers; lane 2, non-transformed maize; lanes 3-4, 028-WT+GUS transformants; lanes 5-6, 028-opt+GUS transformants; lanes 7-8, 028-opt+pA+GUS transformants and lanes 9-10; 028-opt+3pA+GUS transformants. 10 μg protein was loaded for each plant sample.

In FIG. 7B, lanes 1, 26, 27 and 52, molecular size markers; lanes 2-11, 100-WT+GUS transformants; lanes 12 and 38, non-transformed maize; lanes 13 and 39; protein extract from a Axmi100-expressing bacterial strain; lanes 14-23, 100-opt+pA+GUS transformants; lanes 28-37, 100-opt+3pA+GUS transformants and lanes 40-49, 100-opt+GUS transformants. 5 μg protein was loaded for each plant sample.

FIG. 9A) 3' primer pair, FIG. 9B) 5' primer pair.

EXAMPLES

Example 1

Sequences for Improvement of Gene Expression Via Gene Optimization of Regions Flanking Polyadenylation Motifs Axmi028

The wild-type coding region of an AT rich gene, Axmi028 from *Bacillus thuringiensis* (U.S. Pat. No. 8,314,292 B2) lacking the C-terminal crystal domain, was analysed for the polyadenylation motifs as listed in Table 1.

Figure 2A:
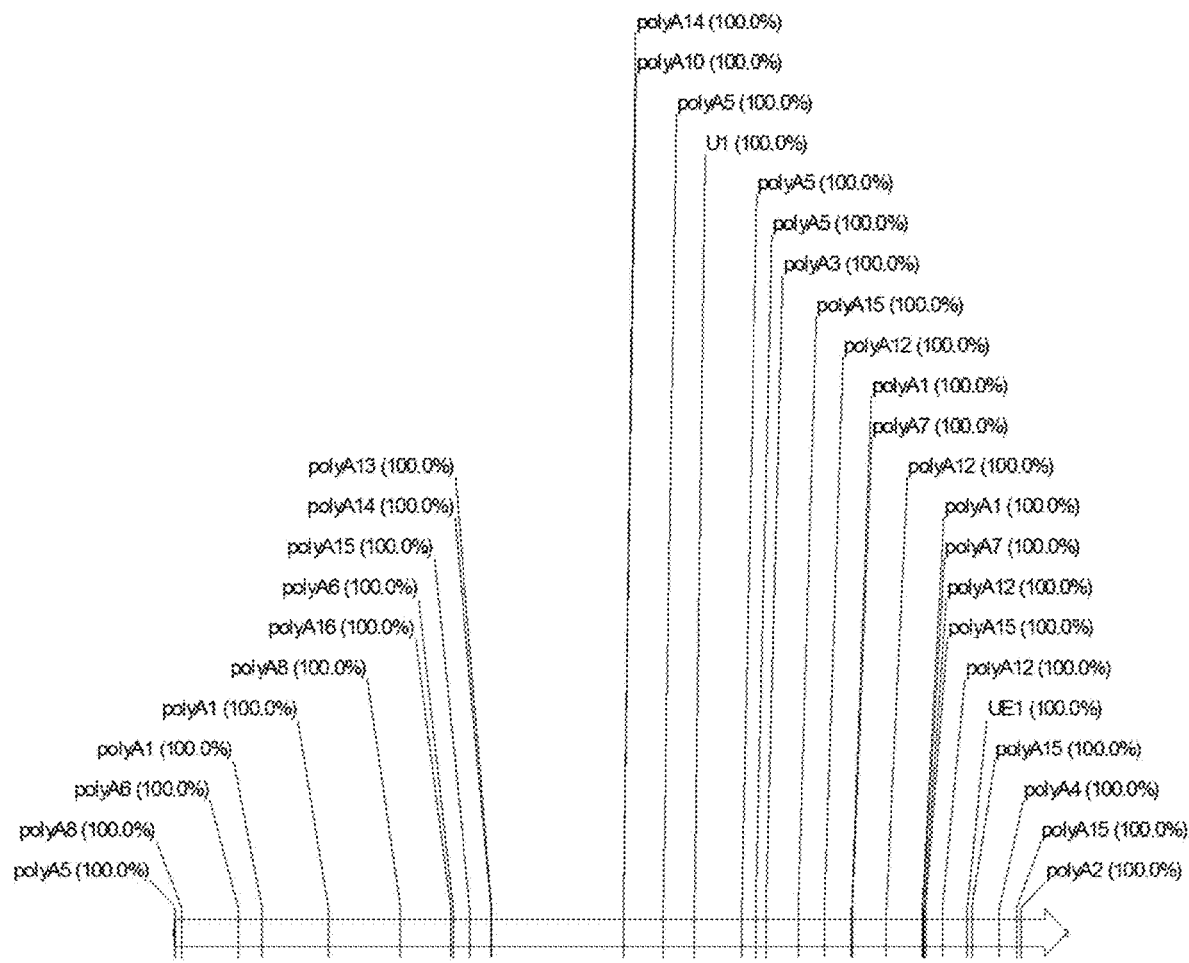
Figure 2B:
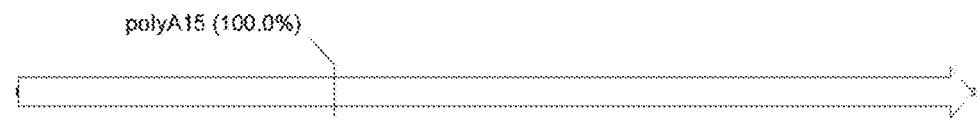
Figure 2C:
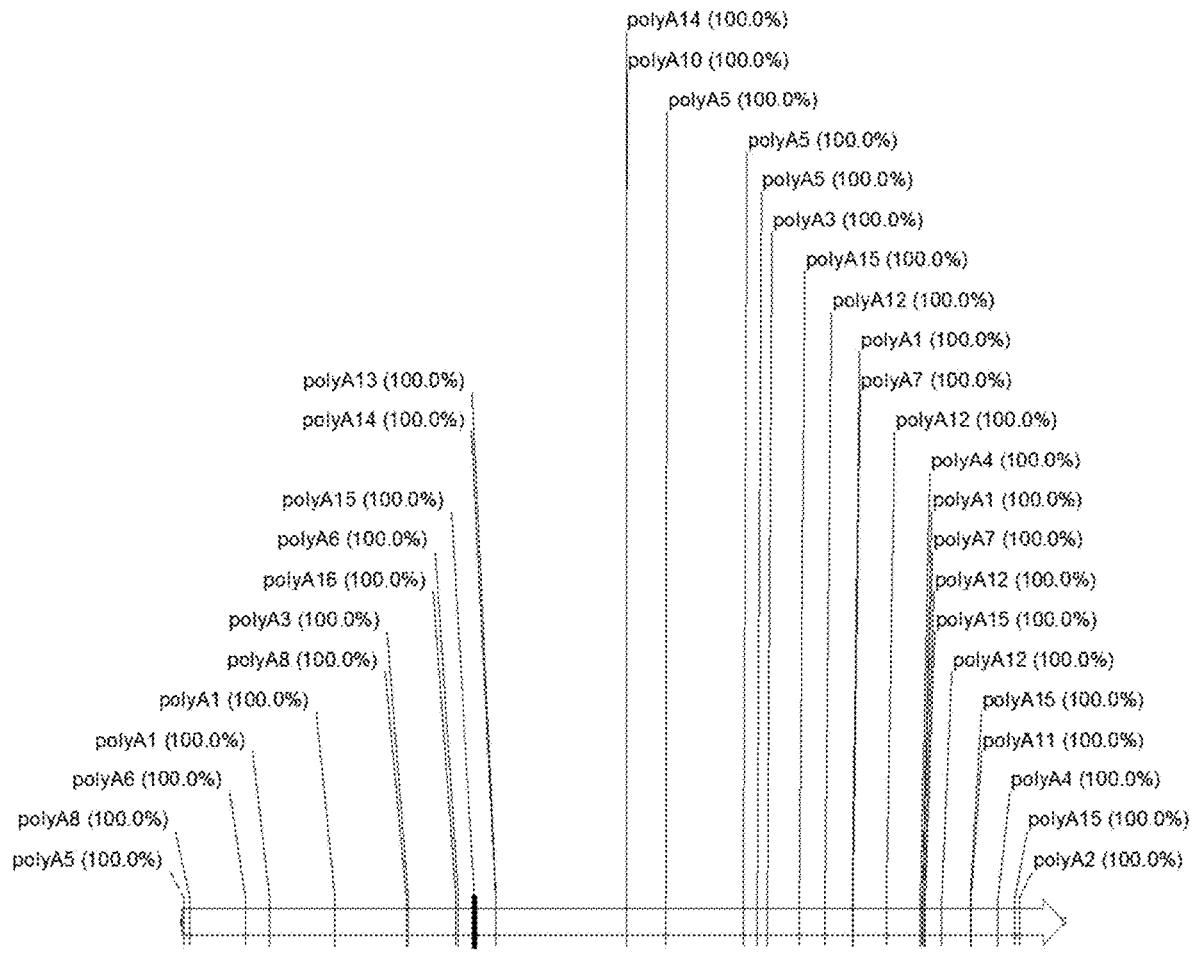

This truncated wild-type coding sequence (028-WT; SEQ ID NO: 1) contains 31 such sites (FIG. 2A). First a codon-optimized Axmi028 sequence was synthesized, as described in U.S. Pat. No. 8,314,292 B2, which lacks 30 of the 31 polyA sites as described in SEQ ID NO: 2 (028-opt FIG. 2B). This sequence was optimized for maize expression. A further sequence (028-opt+pA SEQ ID NO: 3; FIG. 2C) was designed where the 30 putative polyadenylation motif sequences were reintroduced into this optimized 028-opt sequence such that the amino-acid sequence of the Axmi028 sequence is conserved.

Figure 1A:
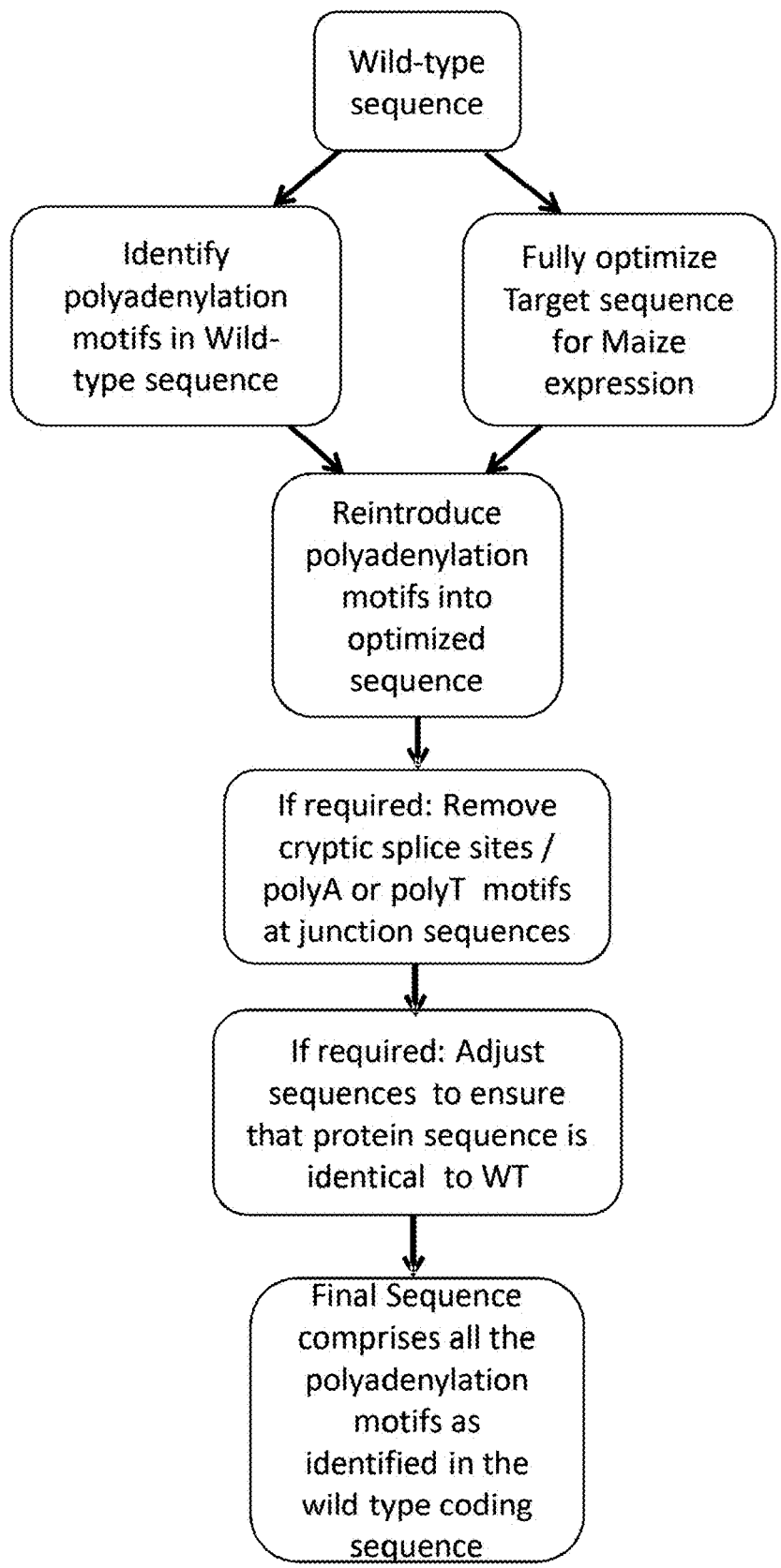

In two cases the reintroduction of the polyadenylation motif resulted in a change of the amino-acid sequence. This was corrected by introducing 3 more base pairs of wild-type sequence 5' of these polyadenylation motifs. In addition the sequence was examined for the presence of additional sequences that might reduce expression which may have been created by the juxtaposition of the optimized and polyadenylation motifs (cryptic splice sites GGTAAG, GGTGAT, GTAAAA and GTAAGT and/or polyA and polyT sequences and/or 7 or more repeated base pairs). No such motifs were found in the 028-opt+pA sequence. This process is outlined in FIG. 1A.

Figure 3A:
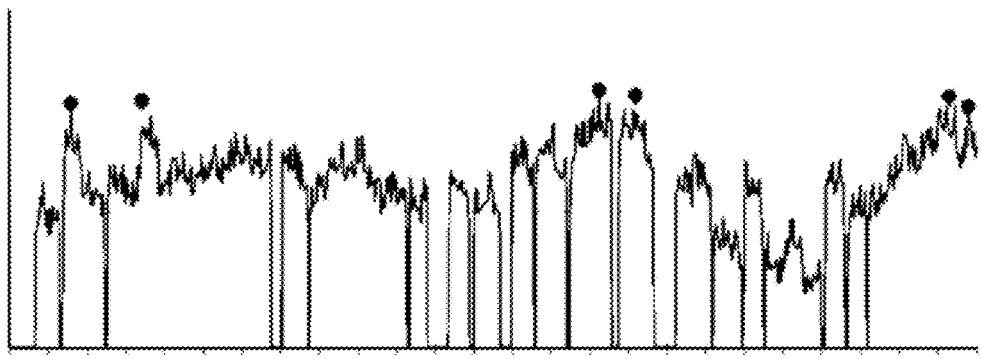
Figure 3B:
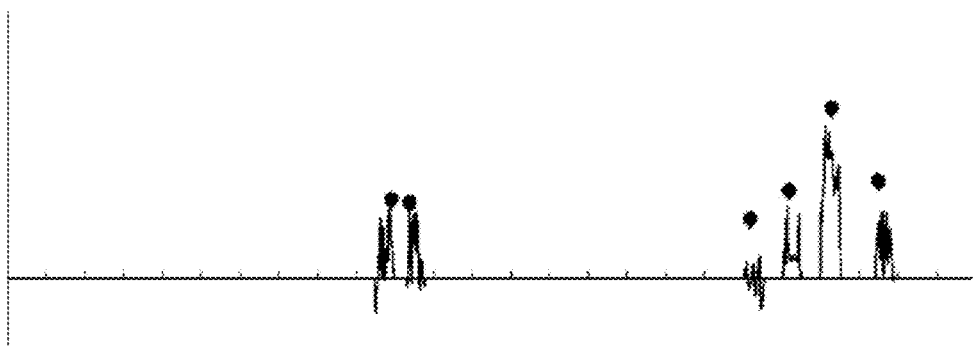
Figure 3C:
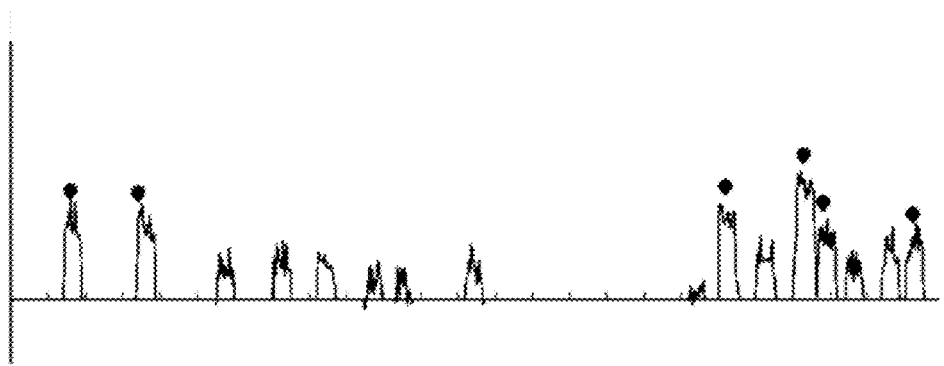
Figure 3D:
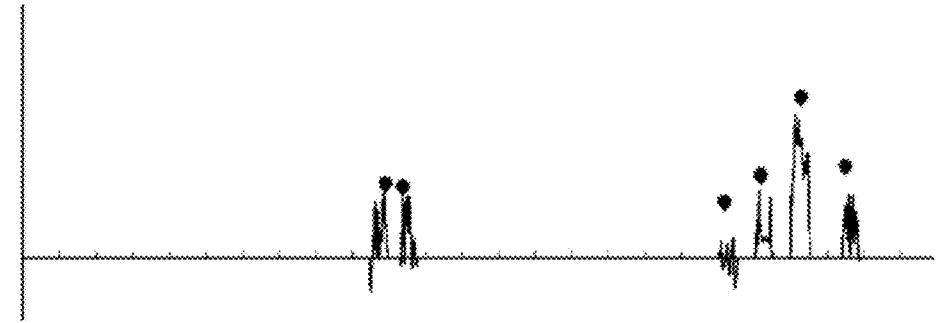

Several attempts have been made in the art to predict the position of polyadenylation sites in plant genes. Ji et al (2015) have developed the algorithm PASPA (PolyA Site Prediction in Plants and Algae; http://bmi.xmu.edu.cn/paspa). This algorithm was applied to the 028-WT, 028-opt and 028-opt+pA sequences using parameters defined for Rice. FIGS. 3A through 3D show the output of this analysis. It can be seen that the likelihood of premature polyadenylation as predicted by PASPA is greatest for the 028-WT sequence (FIG. 3A) and least for the 028-opt sequence (FIG. 3B). The 028-opt+pA sequence (FIG. 3C) has a significant reduction in the likelihood of premature polyadenylation compared to the 028-WT sequence.

Axmi100

Figure 4A:
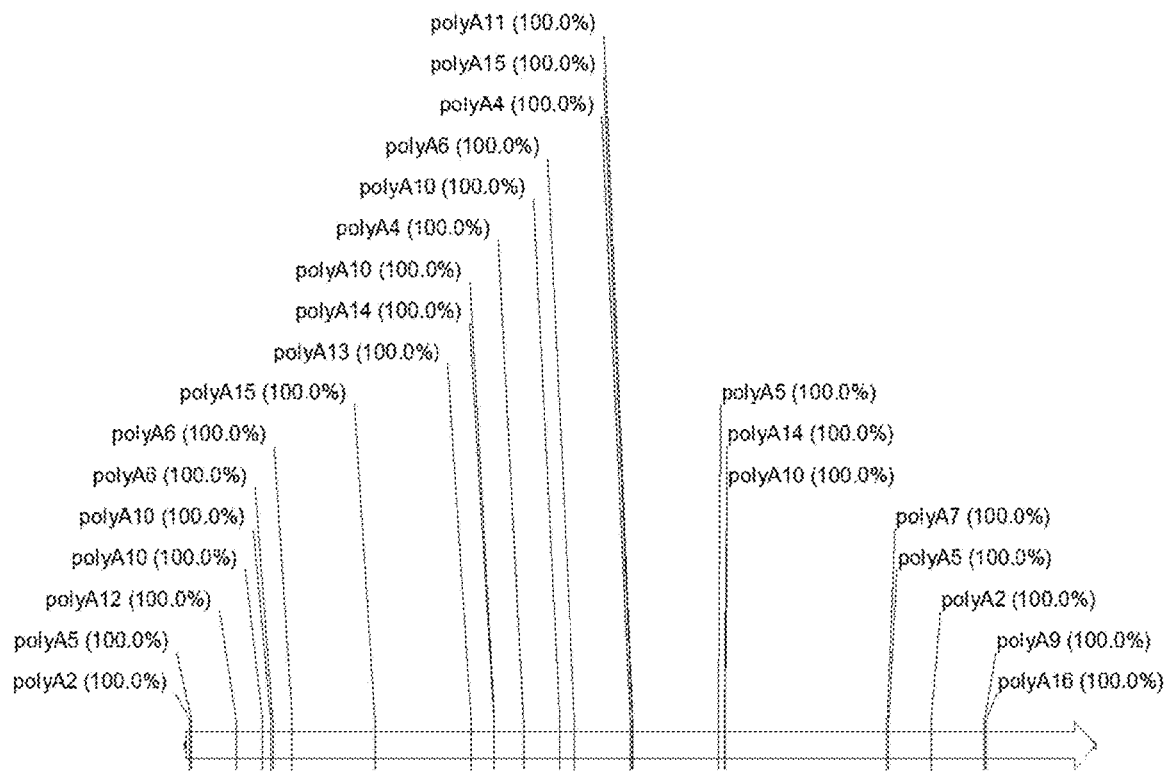
Figure 4B:
Figure 4C:
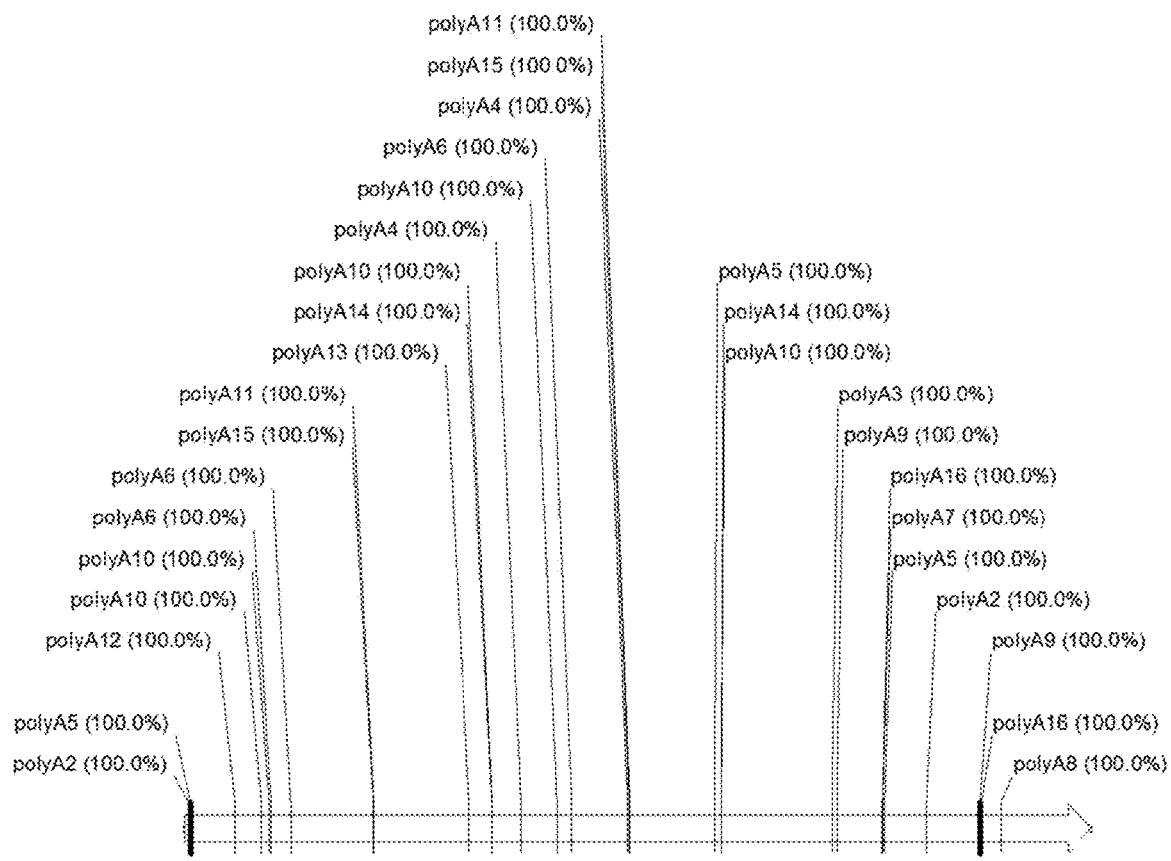

A second AT rich *Bacillus thuringiensis* gene, Axmi100 (US20100005543) was also modified. As for Axmi028, for expression in plants, the C-terminal crystal domain was removed. This truncated wild-type coding sequence, as described in SEQ ID NO: 4 (100-WT, FIG. 4A), contains 25 polyadenylation motifs. A codon-optimized Axmi100 sequence was synthesized (US20100005543) which lacks 24 of the 25 wild-type polyadenylation motifs (100-opt or SEQ ID NO: 5, FIG. 4B). This sequence, optimized for maize expression, however has 5 additional polyadenylation motifs not present in the wild-type sequence. A further sequence, as described in SEQ ID NO: 6 (100-opt+pA FIG. 4C), was synthesized where the 24 putative polyadenylation motifs were reintroduced into this optimized 100-opt sequence at the same nucleic position as identified in the wild type coding sequence. This sequence conserves the amino-acid sequence of Axmi100 and contains no cryptic splice site, polyA or polyT motifs (cryptic splice sites GGTAAG, GGTGAT, GTAAAA and GTAAGT and/or polyA and polyT sequences and/or 7 or more repeated base pairs).

Figure 5A:
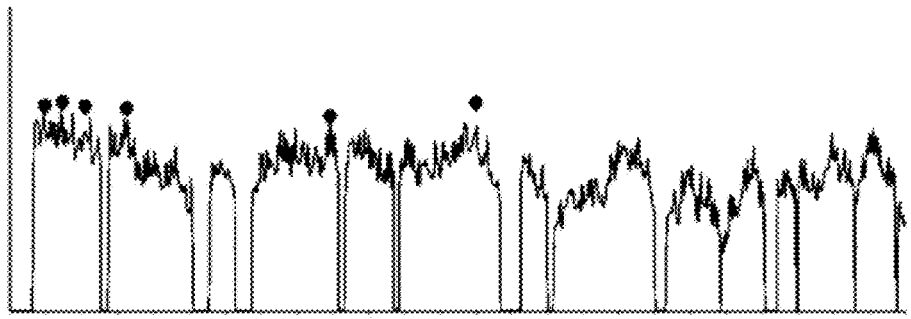
Figure 5B:
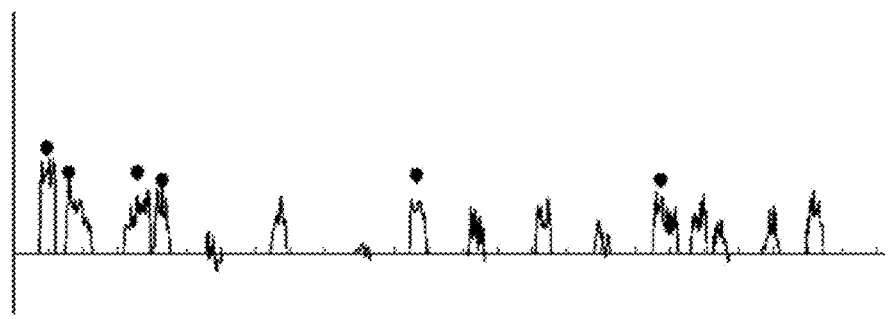
Figure 5C:
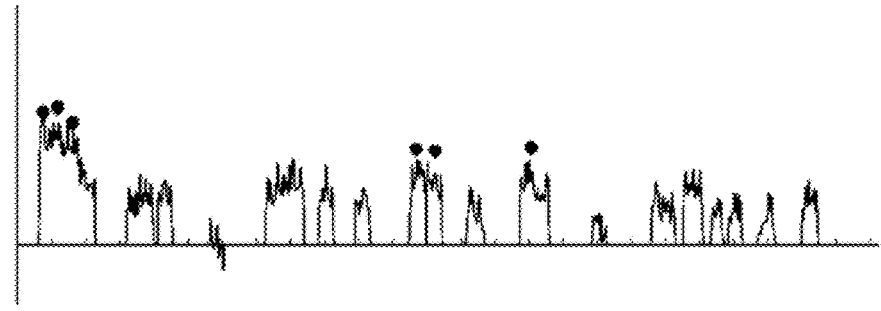
Figure 5D:
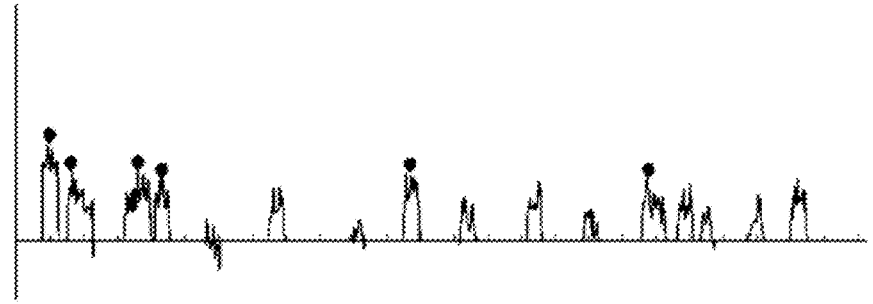

The PASPA algorithm was applied to the 100-WT, 100-opt and 100-opt+pA sequences using parameters defined for Rice. FIGS. 5A through 5D show the output of this analysis. It can be seen that the likelihood of premature polyadenylation as predicted by PASPA is greatest for the 100-WT sequence (FIG. 5A) and least for the 100-opt sequence (FIG. 5B). However the 100-opt+pA sequence (FIG. 5C) has a significant reduction in the likelihood of premature polyadenylation compared to the 100-WT sequence.

Example 2

Transient Expression Testing of Genes Optimized in Regions Flanking Polyadenylation Motifs in Maize and Tobacco Axmi028

Figure 6A:
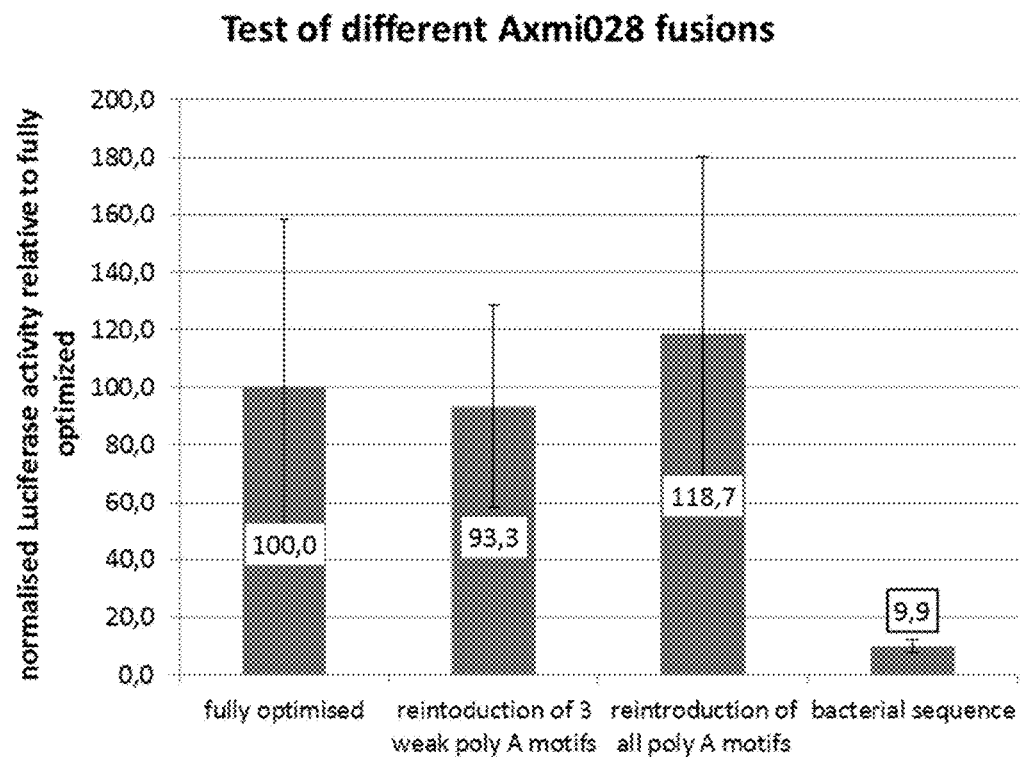

Two transient systems were employed. The first was an indirect assay system where the three different Axmi028 sequences (028-WT, 028-opt and 028-opt+pA) were fused in frame to the reporter firefly luciferase gene (LUC) and placed under the control of the constitutive maize Ubiquitin promoter (SEQ ID NO: 7, SEQ ID NO: 8 and SEQ ID NO: 9). The rationale is that any premature polyadenylation in the Axmi028 sequence will terminate the transcript preventing the possibility to create a transcript containing the full Axmi028+Luc fusion. A reduction in Luc signal from the 028-WT-Luc or 028-opt-pA-Luc fusion genes compared to the 028-opt-Luc control may then be attributed to an increased occurrence of premature polyadenylation. Plasmids containing these fusions are co-bombarded into maize leaf tissue with a control 35S-*Renilla* luciferase construct. 24 hrs later the luminescence of the firefly and *Renilla* luciferases is measured and the signal from the firefly luc normalised using the control *Renilla* luc signal. The normalised firefly luc signal from the 028-WT-Luc gene is then compared to that from the 028-opt-Luc and 028-opt-pA-Luc genes (FIG. 6A).

The second transient system is by agro-infiltration of binary plasmid constructs containing Axmi028 versions into the tobacco *N. benthamiana*. The 028-WT, 028-opt and 028-opt+pA genes driven from the constitutive viral CsVMV promoter (Verdaguer et al (1996)) are cloned into an SB11-derived binary vector (Komari et al (1996)) that also contains the fluorescent reporter gene AnCyan (CloneTech) expressed from the constitutive maize Ubiquitin promoter forming the plasmids 028-WT+Cyan, 028-opt+Cyan and 028-opt+pA+Cyan. These three binary vectors plus the empty SB11+Cyan control are transferred into the *agrobacterium* strain LBA4404 (pSB1)) according to Komari et al (1996). Agro-infiltration is performed with these 4 strains essentially as described by Leckie and Steward (2011). Four leaves of five plants are infiltrated, each leaf being infiltrated with the four strains in different parts of the leaf. After 3 days the zones expressing AnCyan are visualised, then excised. The zones infiltrated with the same agrobacterial strain in each plant are pooled and frozen in liquid nitrogen. Samples are taken for the measurement of transcript levels of the Axmi28 gene and the AnCyan gene by QRT-PCR and for Western analysis using antibodies against Axmi028 and AnCyan. Primer pairs for QR-PCR analysis are designed in the 3' region of the coding sequences of the Axmi028 gene sequences. The transcript expression of 028-WT/AnCyan is then compared to that of 028-opt/AnCyan and to that of 028-opt+pA/AnCyan in order to determine the effect of the termination of transcription by the use of cryptic polyadenylation motifs prior to the position of the primers used for the QRT-PCR reaction.

Similar results can be obtained when the level of Axmi028 protein, normalised for AnCyan protein expression, is compared between the three Axmi028 constructs.

Additional gene constructs were made where Axmi028 versions each have an additional N-terminal His TAG and a C-terminal C-Myc TAG allowing visualization of the Axmi028 proteins in Western blots using HisTAG or C-MycTAG antibodies. These Axmi028 versions are 028-h(WT)m (SEQ ID NO: 17), 028-h(opt)m (SEQ ID NO: 18) and 028-h(opt+pA)m (SEQ ID NO: 19). The 028-h(WT)m, 028-h(opt)m and 028-h(opt+pA)m genes driven from the constitutive viral CsVMV promoter (Verdaguer et al (1996)) were cloned into an SB11-derived binary vector (Komari et al (1996)) that also contains the beta glucuronidase (GUS) reporter gene (Jefferson et al, 1987)) expressed from the constitutive maize Ubiquitin promoter forming the plasmids 028-WT+GUS, 028-opt+GUS and 028-opt+pA+GUS. These three binary vectors plus the empty SB11+GUS control were transferred into the *agrobacterium* strain LBA4404 (pSB1)) according to Komari et al (1996). As described above transient assays are performed in *N. benthamiana*. Protein and RNA Samples are also extracted from 20 to 25 immature maize embryos co-cultivated for 7 days with the agrobacterial strains containing the different Axmi028+GUS constructs. To compensate for potential differences in T-DNA delivery during co-cultivation between the different samples GUS fluorimetrical activity assays using 4-methylumbelliferyl-beta-D-glucuronide (MUG) were performed on each protein sample. Protein amounts used in Westerns were then adjusted to give an equal GUS activity per sample. As for the transient expression analysis in *N. benthamiana*, analysis of these samples allows the comparison of expression of the different Axmi028 versions.

Axmi100

Figure 6B:
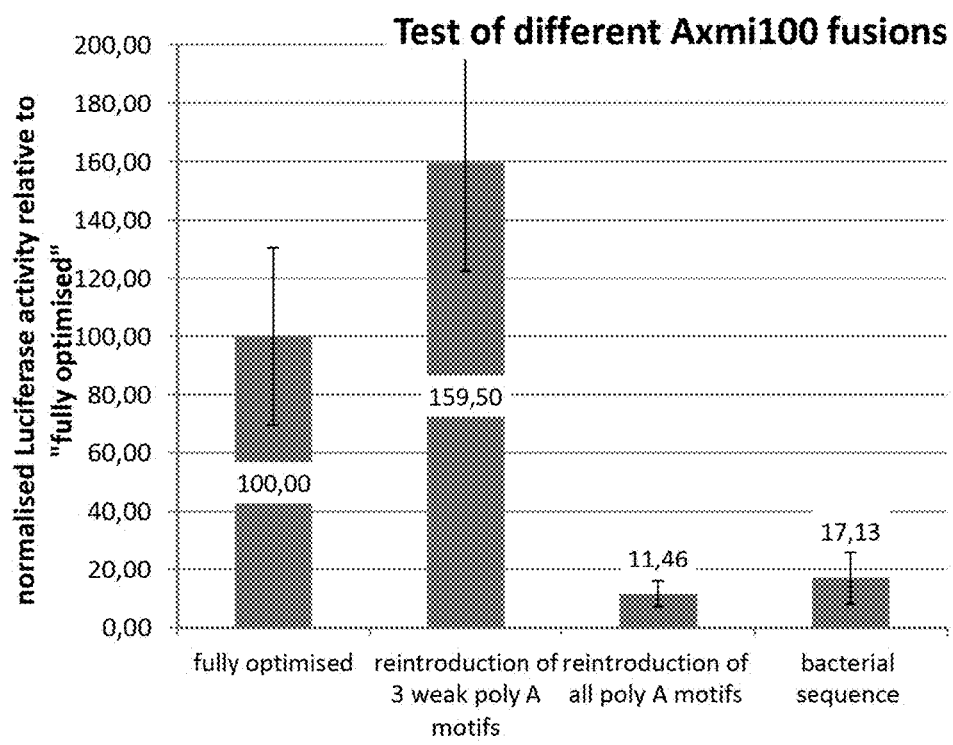

In an identical fashion as described above for Axmi028 the 100-WT, 100-opt and 100-opt+pA sequences are tested by transient assays in maize (SEQ ID NO: 10, SEQ ID NO: 11 and SEQ ID NO: 12) and tobacco. The expression of 100-WT is thus compared to that of 100-opt and to that of 100-opt+pA (FIG. 6B). Western blot analysis was made on the same samples by using a polyclonal antibody raised against Axmi100 protein. The result are in line with the result depicted in FIGS. 6A and 6B: the presence of polyadenylation signals makes it possible to obtain good expression of the protein, better than the expression of the optimized protein in which no polyadenylation have been added, and the expression of the optimized protein in which all wild-type polyadenylation have been added, whereas the wild-type protein is not properly expressed (data not shown).

The Axmi100 versions are also expressed as N-terminal His-Tag and C-terminal C-Myc Tag versions; 100-h(WT)m, 100-h(opt)m and 100-h(opt+pA)m (SEQ ID NO: 20, SEQ ID NO: 21 and SEQ ID NO: 22) in transient assays in tobacco and in immature maize embryos. The expression of 100-h(WT)m is thus compared to that of 100-h(opt)m and to that of 100-h(opt+pA)m.

Example 3

Stable Expression in Maize of Genes Optimized in Regions Flanking Polyadenylation Motifs Axmi028

Figure 7A:
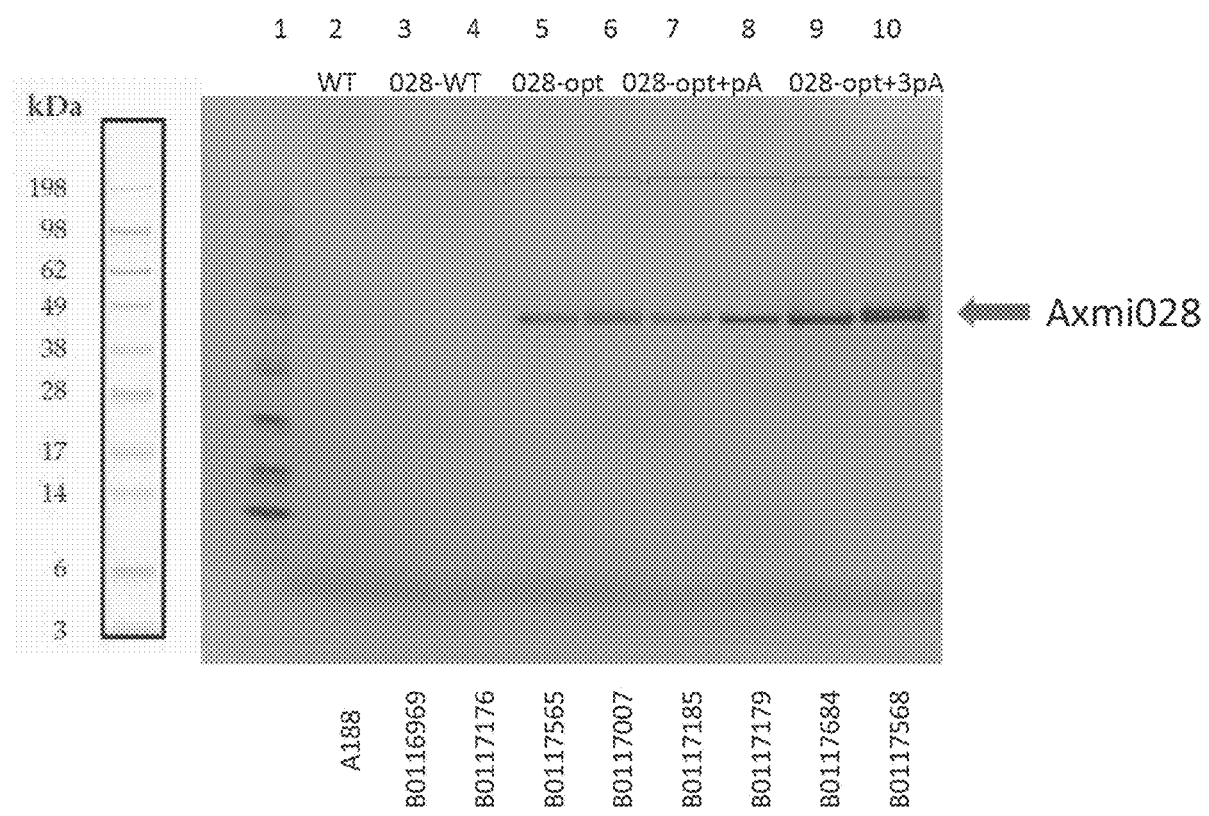

The strains described in example 2 (028-WT+GUS, 028-WT+Cyan, 028-opt+GUS, 028-opt+Cyan, 028-opt+pA+GUS and 028-opt+pA+Cyan) are transformed into maize essentially as described by Ishida et al (1996). A minimum of 10 individual, single copy transformants with an intact T-DNA, are produced for each construct. QRT-PCR and Western analyses are performed on TO leaf material. Leaf Axim028 expression and protein levels of the 028-WT plants are compared to the 028-opt and 028-opt+pA transformants as in the previous example (FIG. 7A).

Axmi100

Figure 7B:
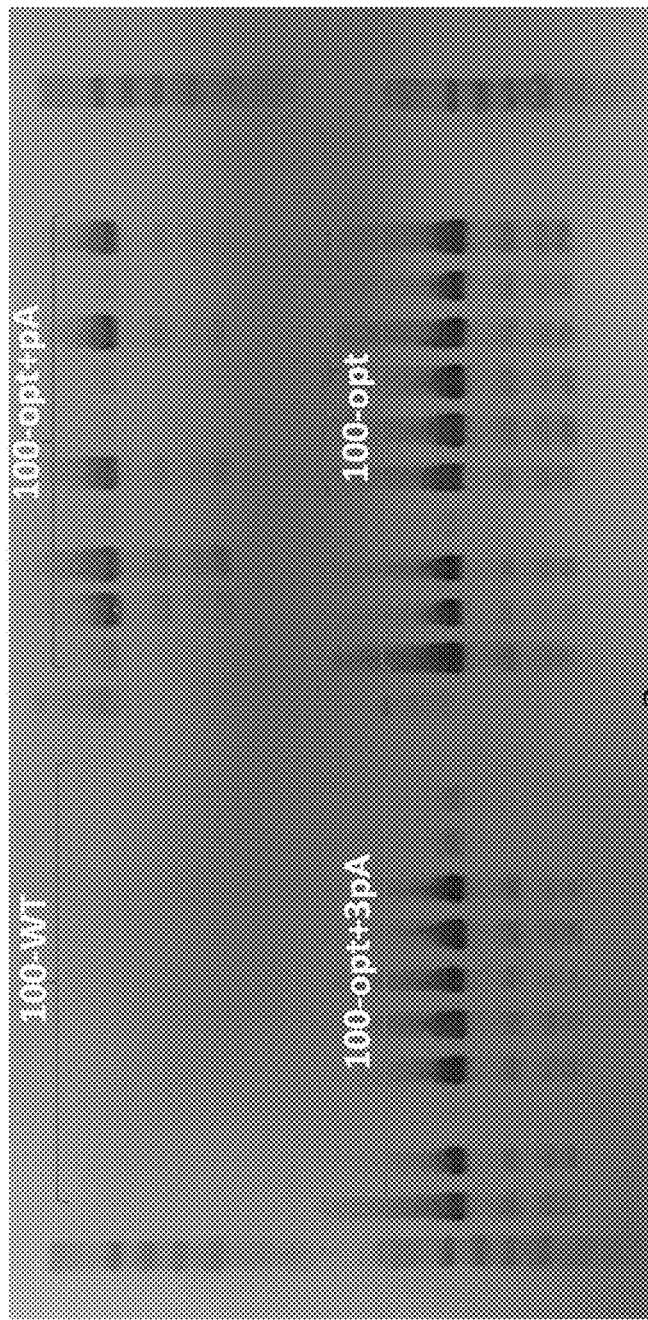

As described above for Axmi028, the different versions of Axmi100 are transformed into maize. Leaf Axmi100 expression and protein levels of the 100-WT plants are compared to the 100-opt and 100-opt+pA as in the previous example (FIG. 7B).

Example 4

Identification of Weak Polyadenylation Motifs that can Remain in Codon-Optimized Sequences A further improvement to the above procedure is to leave only weak polyadenylation motifs in the optimized sequence. Although reintroducing all polyadenylation motifs identified in Table 1 in the optimized sequence significantly improves expression to levels similar to that obtained by a fully optimized sequence the procedure may not be optimal in all cases. This is since as the number of polyadenylation motifs increases in the wild-type sequence the more of the sequence cannot be optimized and the more potential exists for undesirable sequences created at the junctions of optimized and polyadenylation sequences. An in silico approach was used to identify weak and strong polyadenylation sequences in maize. This approach is based on the idea that strong polyadenylation motifs will be under-represented in the coding sequences of maize genes and particularly so in highly expressed genes. Conversely weak polyadenylation motifs should not be under-represented. However the occurrence of a motif may also be dependent on the amino-acids it can encode. Motifs that 'encode' amino-acids used frequently and with codons frequently used for that amino-acid will be overrepresented. Thus keeping the 'weak' motifs that are the most over-represented compared to the theoretical calculation should select motifs that both:

a) Are not strong polyadenylation signals
b) Are frequently used since they encode amino-acids that are frequently used/or codons that are frequently used in maize.

TABLE 1 occurrence of polyadenylation motifs in maize coding sequence
Motif Occurrence in Maize CDS v3

| Motif | PolyA code | Theoretical | Real | % Real |
|---|---|---|---|---|
| ATGAAA | polyA8 | 10081 | 21568 | 214% |
| AATCAA | polyA5 | 10081 | 16116 | 160% |
| AAAATA | polyA12 | 8265 | 12978 | 157% |
| AAGCAT | polyA9 | 12297 | 18669 | 152% |
| AACCAA | polyA3 | 12297 | 15522 | 126% |
| ATAAAA | polyA7 | 8265 | 9660 | 117% |
| AATAAT | polyA2 | 8265 | 9297 | 112% |
| AATAAA | polyA1 | 8265 | 9276 | 112% |
| AATACA | polyA15 | 10081 | 10519 | 104% |
| ATACAT | polyA11 | 10081 | 9945 | 99% |
| ATATAA | polyA4 | 8265 | 7009 | 85% |
| CATAAA | polyA16 | 10081 | 7884 | 78% |
| ATTAAA | polyA13 | 8265 | 6364 | 77% |
| AATTAA | polyA14 | 8265 | 6167 | 75% |
| ATTAAT | polyA10 | 8265 | 5771 | 70% |
| ATACTA | polyA6 | 10081 | 6638 | 66% | a) Analysis of CDSs in Maize CDS Database v3:

First the entire predicted coding regions of maize were analysed (maize CDS database v3, ftp://ftp.ensemblgenomes.org/pub/release-27/plants/fasta/zea_mays/cds/). The predicted number of each polyadenylation motif was determined in this dataset using the observed size of the dataset (63279365 bp) and the base-pair composition of this dataset (54.95% GC). Then the actual number of occurrences was determined and the ratio of real/predicted occurrences calculated (see Table 1). Results show that some polyadenylation motifs are significantly under-represented and some significantly overrepresented.

Figure 1B:
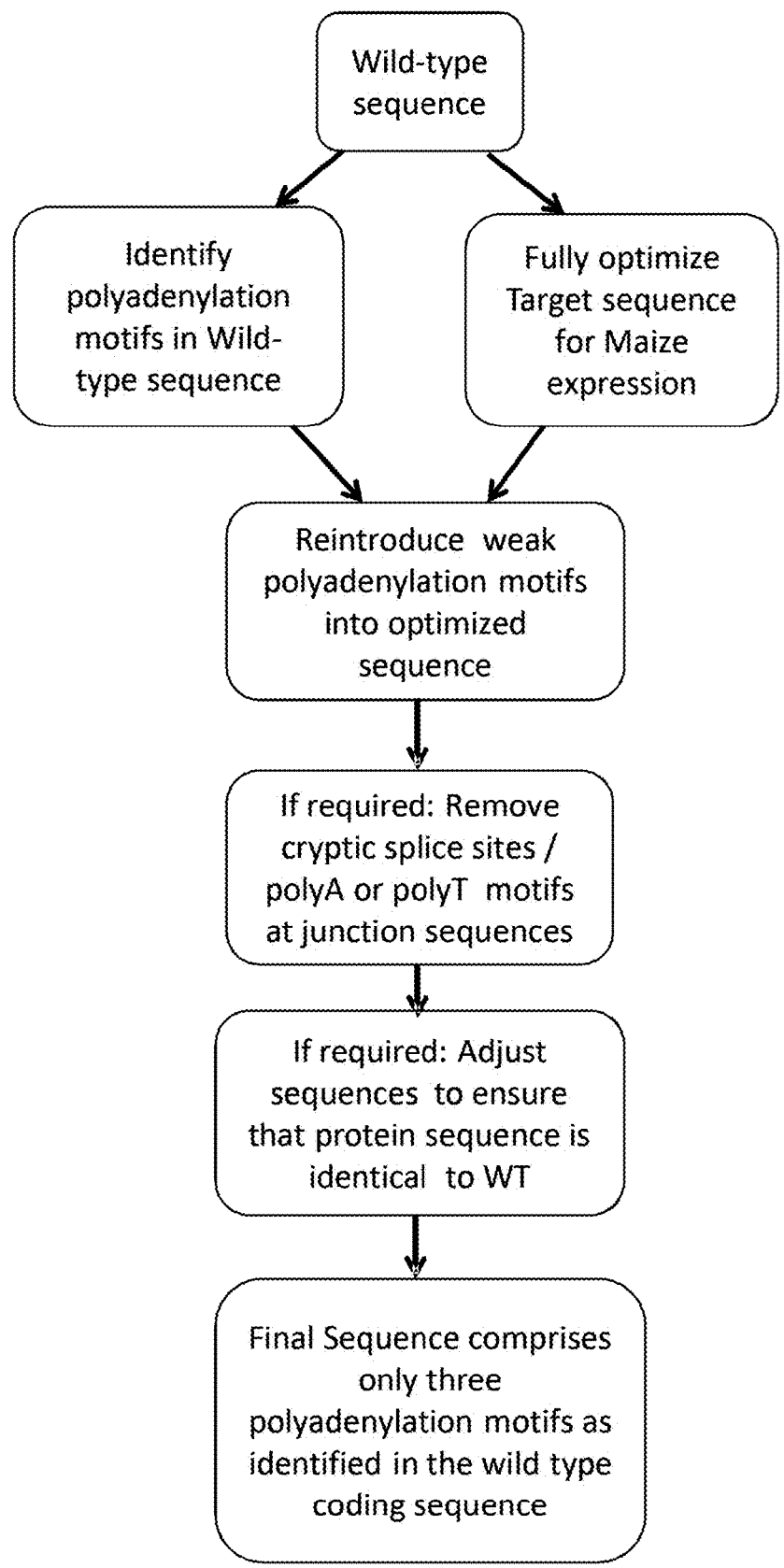
Figure 1C:
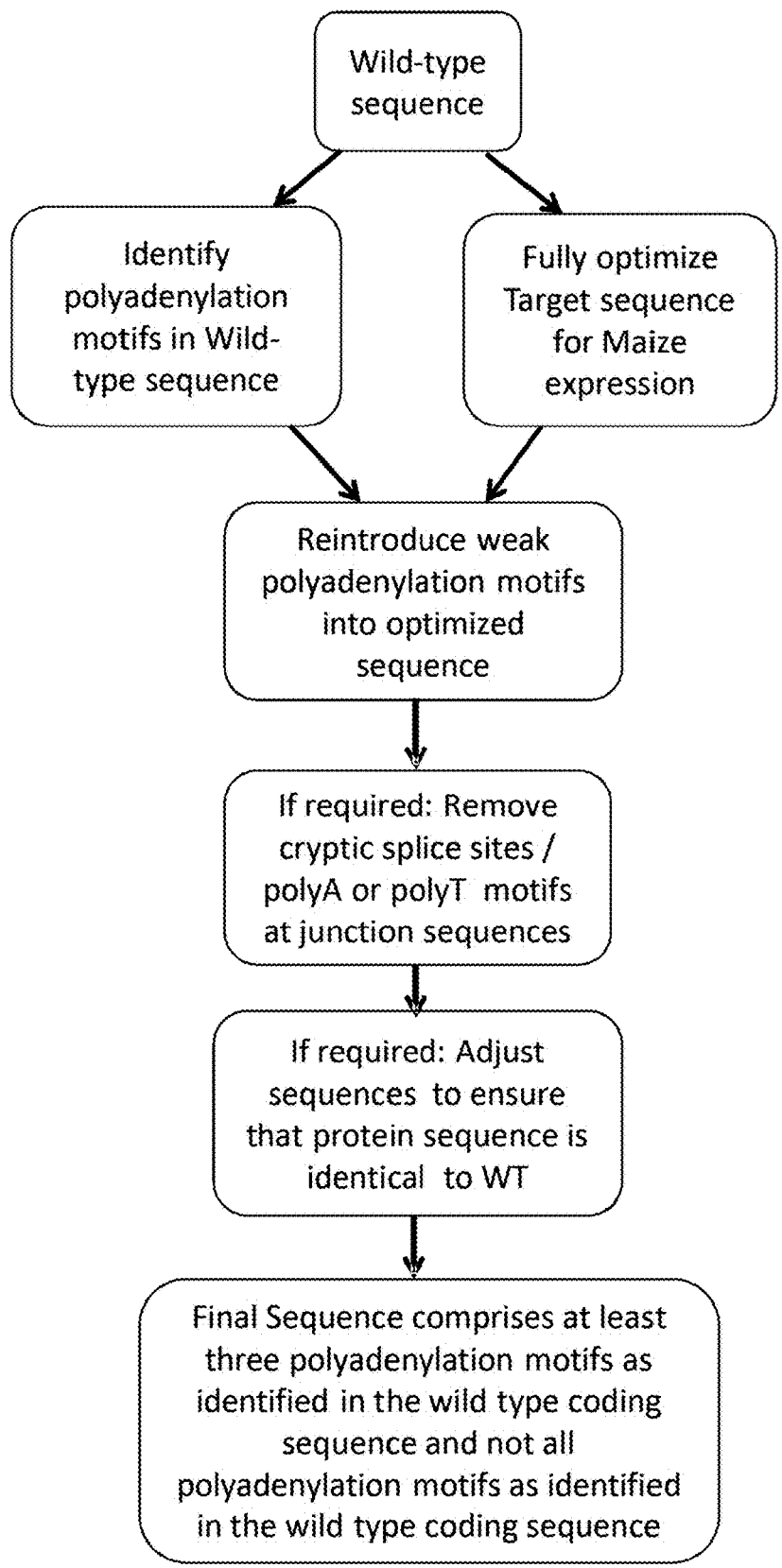

In the maize CDSv3 dataset 4 motifs are 150% or more over-represented. Those that are over-represented are candidates for sequences that are weak polyadenylation motifs and sequences that allow good gene expression. These polyadenylation sequences can be left within optimized sequences with a low probability that they will compromise gene expression. This protocol is outlined in FIG. 1B.

b) Analysis of CDS in Monocotyledons:

A crop-specific search for polyadenylation motifs as listed in table 1 was performed to define those motifs that occur with high levels in the CDS of the respective crop of interest. For that purpose CDS of 2 defined corn lines (B73, AGPv3.22) were analyzed postulating that, as in the previous example, the CDS contain codons that are frequently used to encode certain amino acids in the crop. Polyadenylation motifs that are present within codons of the CDS are not strong, but only minor-functional or likely non-functional. So those naturally occurring motifs can remain in any transgene as they would not influence its stable expression in the crop of interest and will be referred to as crop-specific weak motifs.

First the presence of polyadenylation motifs was analyzed in those different corn datasets. For count checks, Oligo-Counter (http://webhost1.mh-hannover.de/davenport/oligo-counted, Tümmler laboratory at Hannover Medical School, Germany) and J Browse (Skinner et al, Genome Res. 2009. 19: 1630-1638) were used to check motif distributions in the genomes. Those counts were normalized to the total number of predicted transcript per CDS dataset.

Table 2 is showing the percentage of CDS that contain the given polyadenylation motif in for B73 and AGPv3.22 data set. To facilitate the comparison, the column "motif occurrence maize CDSv3" from table 1 is added. It represents in percentage the actual motif occurrence in the entire maizev3 dataset divided by the theoretical occurrence in the dataset. The distribution of polyadenylation motifs was very similar in all corn datasets with little variations in their rankings. It is interesting to note that the top 5 polyadenylation motifs ATGAAA, AAGCAT, AACCAA, AATCAA and AAAATA occur in corn transcripts with relatively high frequency (>10% of CDS containing these motifs in dataset B73). This result is consistent with the frequencies found in experiment described above in section a).

Even though this analysis is not considered as providing an exhaustive list of all the weak polyadenylation motifs, it can be concluded that the 5 polyadenylation motifs identified are confirmed as weak motifs in corn.

In addition to the corn datasets, another monocotyledon crop Sorghum bicolor (Sbicolor_255_v2.1) was analyzed (Table 2). Analogously to corn these CDS sets were analyzed for their total abundance of polyadenylation motifs counts (see table 2). Those counts were normalized to the total number of predicted transcript per CDS dataset. Remarkably, the two different monocot crops show very similar relative abundance of all polyadenylation motifs with the top five most abundant motifs being exactly the same.

According to those data the polyadenylation motifs ATGAAA, AAGCAT, AACCAA, AATCAA and AAAATA can remain in any transgene expressed in monocotyledons as they would not influence its stable expression in the crop of interest and will be referred to as monocot-specific weak polyadenylation motifs.

Interestingly, the six strongest ATAAAA, CATAAA, ATACTA, ATTAAA, AATTAA, and ATTAAT polyadenylation motifs are also consistent amongst monocotyledons.

c) Comparison between monocotyledons and dicotyledons weak polyadenylation motifs:

In addition to the monocotyledons datasets, a dicotyledon crop Beta vulgaris (RefBeet-1.2) was analyzed. Table 2 shows that B. vulgaris presents a similar distribution of motifs from the weakest to strongest motifs. One motif AATAAT was found more frequently in the CDS dataset then in those of monocotyledons CDSs. However, there is a clear overlap in the most abundant motifs between all crop datasets analyzed.

These data suggest that the three polyadenylation motifs ATGAAA, AAGCAT and AATCAA can likely remain in any transgene expressed in flowering plants.

The overall data shows that the identification of the five motifs ATGAAA, AAGCAT, AACCAA, AATCAA and AAAATA as weak polyadenylation motifs is robust in the plant kingdom.

ATGAAA show highest abundance across all genes and remained even in optimized sequences to a high percentage. In addition to those two motifs, the motif AAAATA also shows high abundance in the set of genes analyzed.

According to these data these polyadenylation motifs are unlikely to influence transgene expression in any crop of interest.

TABLE 2

Occurrence of polyadenylation motifs in monocotyledons and dicotyledons. The results shown in column "motif occurrence in maize CDSvs" is an extraction from table 1.

|  | B73 | AGP v 3.22 | maize CDSv3 |  | S. bicolor 255v2.1 |  | Ref Beet 1.2. |
| --- | --- | --- | --- | --- | --- | --- | --- |
| ATGAAA | 13.72 | 34.10 | 214.00 | ATGAAA | 44.40 | ATGAAA | 78.70 |
| AAGGAT | 12.24 | 29.52 | 152.00 | AAGCAT | 38.65 | AAGCAT | 50.34 |
| AACCAA | 12.02 | 24.54 | 126.00 | AACCAA | 31.81 | AACCAA | 44.36 |
| AATCAA | 11.82 | 25.48 | 160.00 | AATCAA | 34.04 | AATCAA | 63.11 |
| AAAATA | 10.88 | 20.52 | 157.00 | AAAATA | 26.06 | AAAATA | 44.16 |
| ATAAAA | 8.12 | 15.27 | 117.00 | ATAAAA | 19.71 | ATAAAA | 36.30 |
| ATACAT | 8.05 | 15.73 | 99.00 | ATACAT | 20.31 | ATACAT | 28.90 |
| AATACA | 7.84 | 16.63 | 104.00 | AATACA | 21.14 | AATACA | 32.22 |
| AATAAA | 7.59 | 14.67 | 112.00 | AATAAA | 19.06 | AATAAA | 33.00 |
| AATAAT | 7.02 | 14.70 | 112.00 | AATAAT | 20.11 | AATAAT | 45.21 |
| ATATAA | 5.93 | 11.08 | 85.00 | ATATAA | 14.29 | ATATAA | 27.18 |
| CATAAA | 5.85 | 12.47 | 78.00 | CATAAA | 15.61 | CATAAA | 24.80 |
| AATTAA | 5.15 | 9.75 | 75.00 | AATTAA | 12.29 | AATTAA | 29.23 |
| ATTAAA | 4.87 | 10.06 | 77.00 | ATTAAA | 12.60 | ATTAAA | 30.86 |
| ATACTA | 4.71 | 10.50 | 66.00 | ATACTA | 13.63 | ATACTA | 24.49 |
| ATTAAT | 4.59 | 9.13 | 70.00 | ATTAAT | 11.02 | ATTAAT | 28.55 | d) Analysis of Polyadenylation Motifs in Transgenes Expressed in Planta

In order to assess the presence of polyadenylation motifs in transgenes expressed in planta, 21 bacterial gene sequences and 5 gene sequences from eukaryotic organisms were analyzed. Those genes were shown to be expressed in planta. The total number of polyadenylation motifs was counted to identify those motifs in transgenes that were described as functional and/or expressed in planta (demonstrated either via analysis of transgene expression levels or via new phenotypes detected in transgenic plants). Based on those numbers of polyadenylation motifs counted in the transgenes, the abundance of any motif was calculated (number of motifs/number of genes analyzed). According to their calculated abundance across genes, species of origin & expressing crop the polyadenylation motifs were grouped: Signals with high abundance (≥50% in all genes analyzed) are rated as non-functional or very weak polyadenylation signals, those signals with medium abundance (≥25% in all genes analyzed) are rated as minor functional or weak polyadenylation signals. Signals with low abundance (≥0% in all genes analyzed) are rated as functional or strong polyA signals.

To assess if specific motifs were deleted in genes optimized for transgene expression in planta with higher frequency, the percentage of polyadenylation motifs that remained after optimization was calculated. Even though this analysis is not considered to provide an exhaustive identification of all weak polyadenylation motifs existing in plants, the retention of motifs in addition to high abundance in this variety of genes is a valuable indication for their weak impact on transcript stability. The two motifs AATCAA and Example 5

Transient Expression Testing of Genes that are Maize Codon-Optimized but Contain a Minimum of Three Polyadenylation Motifs at the Wild-Type Position a) Transient Expression System as Performed in Example 2: Axmi028

Figure 2D:
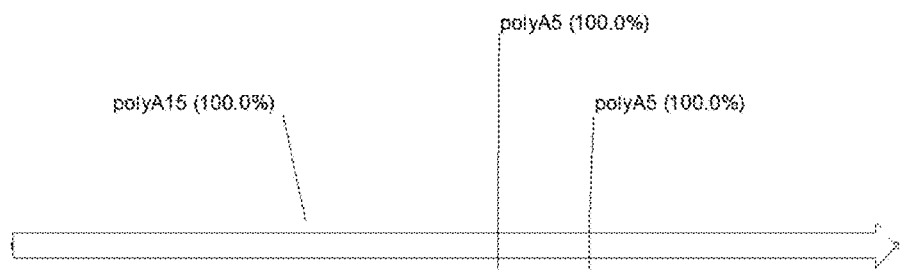

The Amxi028 wild-type but C-terminus truncated sequence was examined for the presence of weak polyadenylation motifs that can remain in the optimized sequence. Two ATGAAA and four AATCAA motifs were found, these are the most overrepresented motifs in the maize CDSv3 database. The optimized sequence already has an AATACA motif present at its wild-type position of 626 bp. This motif is neither underrepresented nor overrepresented in the maize CDS v3 dataset (104% of real/theoretical). Two of the four AATCAA motifs were introduced in the optimized sequence (positions 1036 bp and 1232 bp) giving in total three weak motifs that are identified in the wild-type position in the modified optimized coding sequence. This sequence 028opt+3pA as described in SEQ ID NO: 13 (FIG. 2D), does not comprise any of the strongest ATAAAA, CATAAA, ATACTA, ATTAAA, AATTAA, and ATTAAT polyadenylation motifs. It was analyzed by PASPA (FIG. 3D) and found to give an identical probability curve of polyadenylation as the fully optimized sequence (FIG. 3B). This example shows that the addition of weak motifs at their wild-type position in the optimized coding sequence has no effect on the level of predictability of the polyadenylation motifs as compared to that of the modified optimized sequence.

Figure 8:
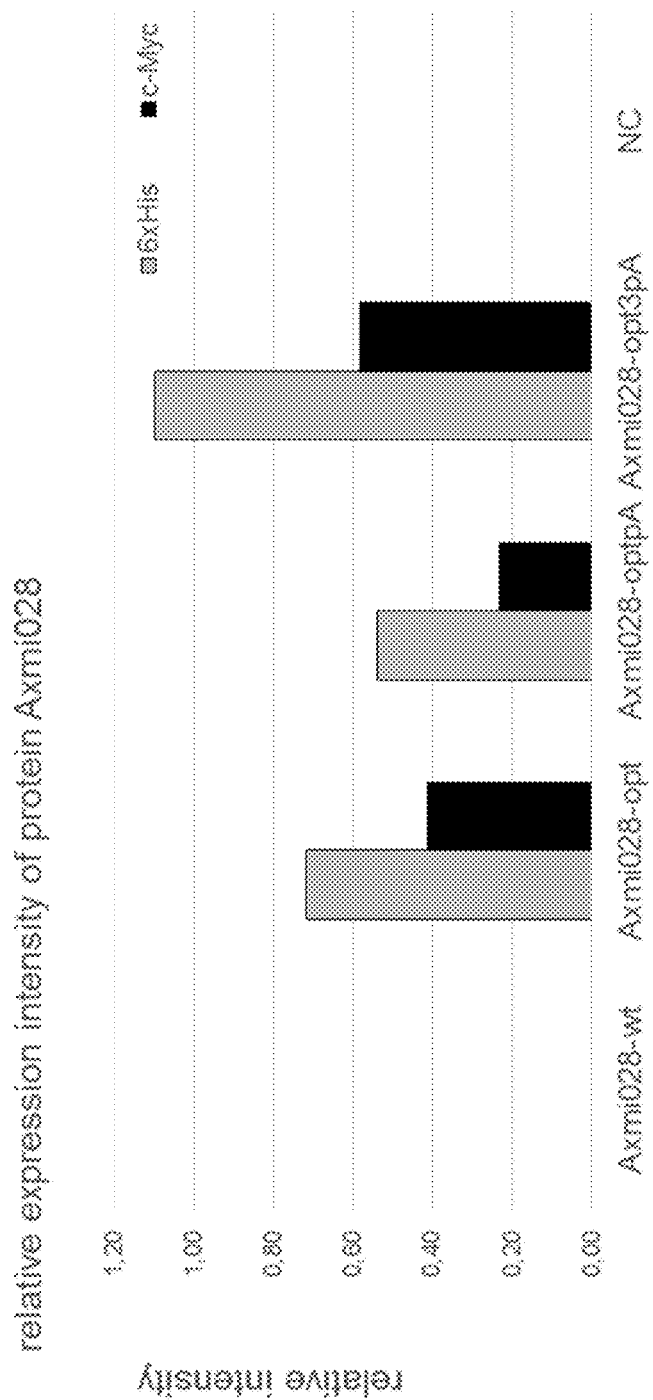
FIG. 8 depicts the relative expression intensity of the full length protein Axmi028 in maize protoplast transient assay. Within every lane the intensity of the detected c-Myc and His tags signals was set into relation to the nptII signal as calculated via the software Image Lab 5.2.1, BioRad.

This 028-opt+3pA sequence is analyzed in the maize (SEQ ID NO: 15) and tobacco and maize embryo transient testing systems (SEQ ID NO: 23) as described in examples 2 and 3. The level of RNA and protein expression obtained from the 028-opt+3pA sequence is then compared to that obtained from the 028+opt sequence.

b) Transient Expression System of the Axmi028 Gene in Maize Protoplasts:

Different Axmi028 versions were transformed into maize protoplasts by transient transfection. The 028-WT, 028-opt, 028-optpA and 028-opt3pA genes driven from the doubled version of constitutive viral 35S promoter (Guilley et al. 1982) are cloned into an pD35-derived vector (http://www.dna-cloning.com/) that adds a N-terminal His tag and a C-terminal Myc tag to each of the Axmi028 versions. It also contains the nptII neomycin phosphotransferase gene referring resistance to kanamycin expressed from the constitutive nos promoter (Depicker et al. 1982) forming the plasmids pD35-nH-cM-Axmi028-wt, pD35-nH-cM-Axmi028-opt, pD35-nH-cM-Axmi028-optpA, pD35-nH-cM-Axmi028-opt3pA (SEQ ID NO: 29, SEQ ID NO: 30, SEQ ID NO: 31, SEQ ID NO: 32, respectively). These four vectors plus a control vector expressing no Axmi028 but a reporter gene td-tomato (SEQ ID NO: 33) are transfected into corn protoplasts of corn line A188 according to the protocol of PEG-mediated transformation of plant protoplasts (Sheen, 2002). 48 h post transfection protoplasts were harvested by centrifugation, total protein was analyzed for the presence of Axmi028 versions by Western analysis by using a primary antibody anti-6X His IgG labeled with fluorescent dye CF680 (N-terminal His-tag detection via filter Alexa 680), a primary antibody anti-c-Myc-Cy3 labeled with fluorescent dye Cy3 (C-terminal Myc-tag detection via filter Alexa 546) and a nptII antibody with an secondary HRP-conjugated antibody for nptII detection as an internal control. The level of Axmi028 protein, normalised for nptII protein expression, is compared between the four Axmi028 constructs. FIG. 8 depicts the relative expression intensity of Axmi028 protein. Detection of the full-length Axmi028 versions is made via the N-terminal His tag (detection: fluorescence filter Alexa680) and the C-terminal Myc tag (detection: fluorescence filter Alexa546). Detection of nptII (detection: chemiluminescence) as internal transformation control was possible in all samples. Within every lane the intensity of the detected c-Myc and 6His signals was set into relation to the nptII signal as calculated via the software Image Lab 5.2.1, BioRad.

Conclusions on Axmi028 Transient Assays:

FIG. 6A shows that in the transient 028-Luc maize assay the expression of luciferase from the 028-WT-Luc sequence is 10% of that from the 028-opt-Luc sequence. The addition of 3 or all polyA motifs to the optimized sequence did not reduce expression of luciferase compared to that obtained from the 028-opt-Luc sequence.

FIG. 8 shows the protein expression of Axmi028-WT, 028-opt, 028-optpA and 028-opt3pA in corn protoplasts after transient transformation. Signal detection was only possible for the optimized versions but not for the WT. The addition of 3 polyadenylation motifs to the optimized sequence did not reduce expression compared to that obtained from the 028-opt sequence. In this assay, the addition of 3 polyadenylation motifs gives higher protein expression levels than the expression of 028-opt and 028-opt-pA. In contrast the expression of 028-opt-pA was lower than that of 028-opt.

Axmi100

Figure 4D:
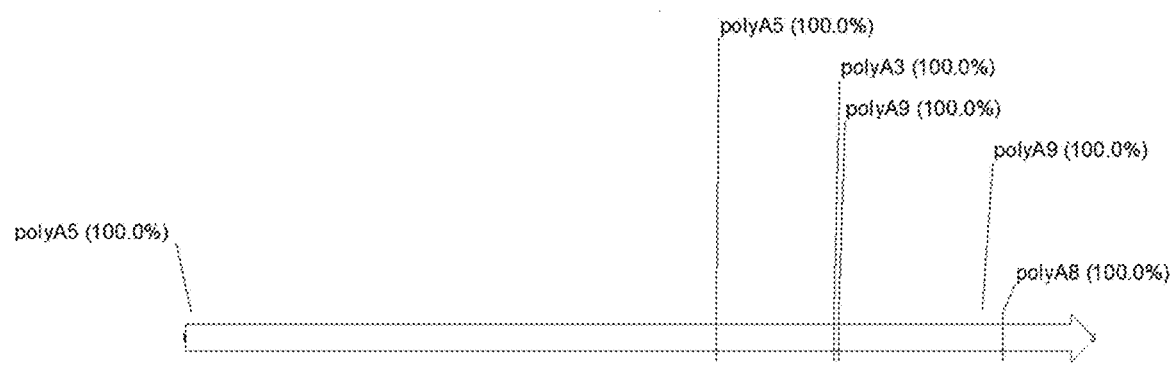

The Ami100 wild-type but C-terminus truncated sequence was examined for the presence of weak polyadenylation motifs that can remain in the optimized sequence. Three AATCAA motifs were found, these are overrepresented motifs in the maize CDSv3 database. The optimized sequence already has an AAGCAT motif present at its wild-type position of 1788 bp. This motif is overrepresented in the maize CDS v3 dataset (152% of real/theoretical). The first two of the three AATCAA motifs were introduced in the optimized sequence (positions 13 bp and 1192 bp) giving three weak polyadenylation motifs identified in the optimized coding sequence at the wild-type position. This sequence 100opt+3pA as described in SEQ ID NO: 14 (FIG. 4D) finally comprises 6 weak polyadenylation motifs and does not comprises any of the strongest ATAAAA, CATAAA, ATACTA, ATTAAA, AATTAA, and ATTAAT polyadenylation motifs. It was analyzed by PASPA (FIG. 5D) and as for Axmi028+3pA, found to give an identical probability curve of polyadenylation as the fully optimized sequence (FIG. 5B).

This 100-opt+3pA sequence is analyzed in the maize (SEQ ID NO: 16) and tobacco and maize embryo transient testing systems (SEQ ID NO: 24) as described in examples 2 and 3. The level of RNA and protein expression obtained from the 100-opt+3pA sequence is then compared to that obtained from the 100-opt sequence.

Western blot analysis was made on the same samples by using a polyclonal antibody raised against Axmi100 protein. The result are in line with the result depicted in FIGS. 6A and 6B: the presence of polyadenylation signals makes it possible to obtain good expression of the protein, better than the expression of the optimized protein in which no polyadenylation have been added, and the expression of the optimized protein in which all wild-type polyadenylation have been added, whereas the wild-type protein is not properly expressed (data not shown).

Conclusion on Axmi100 Expression in Transient Assay:

FIG. 6B shows that in the transient Axmi100-Luc assay the expression of luciferase from the 100-WT-Luc sequence is 17% of that from the 100-opt-Luc sequence. The addition of 3 polyA motifs to the optimized sequence did not reduce expression of luciferase compared to that obtained from the 100-opt-Luc sequence. However the addition of all the polyA motifs reduced luciferase expression to 11% of the 100-opt-Luc sequence.

Western Blot, which looks at the protein quantity rather than at the activity, confirms the results shown in FIG. 6B.

Example 6

Stable Expression Testing of Genes that are Maize Codon-Optimized but Contain a Minimum of Three Polyadenylation Motifs Axmi028

The strains described in example 2 and 5 (028-WT+GUS, 028-WT+Cyan, 028-opt+GUS, 028-opt+Cyan, 028-opt+pA+GUS, 028-opt+pA+Cyan, 028-opt+3pA+GUS and 028-opt+3pA+Cyan) are transformed into maize essentially as described by Ishida et al (1996). A minimum of 10 individual, single copy transformants with an intact T-DNA, are produced for each construct. QRT-PCR and Western analyses are performed on T0 leaf material. Leaf Axim028 expression and protein levels of the 028-WT plants are compared to the 028-opt and 028-opt+3pA transformants, The Western blot analyses on maize leaf protein extracts from plants transformed with Axmi028+GUS constructs (FIG. 7A) were performed with an antibody against the C-Myc TAG ([9E10]—Chip Grade ab32" (abcam)). No Axmi028 protein could be detected in plants transformed with the 028-WT gene. Axmi028 protein expression could be observed in plants transformed with the 028-opt, 028-opt+3pA and 028-opt+pA sequences. This expression seemed highest in plants transformed with 028-opt+3pA.

Axmi100

As described above for Axmi028, the different versions of axmi100 are transformed into maize. Levels of Lepidopteran resistance in 100-opt and 100-opt+3pA transformed plants are compared to levels of 100-WT transformants in leaf feeding assays.

Figure 9A:
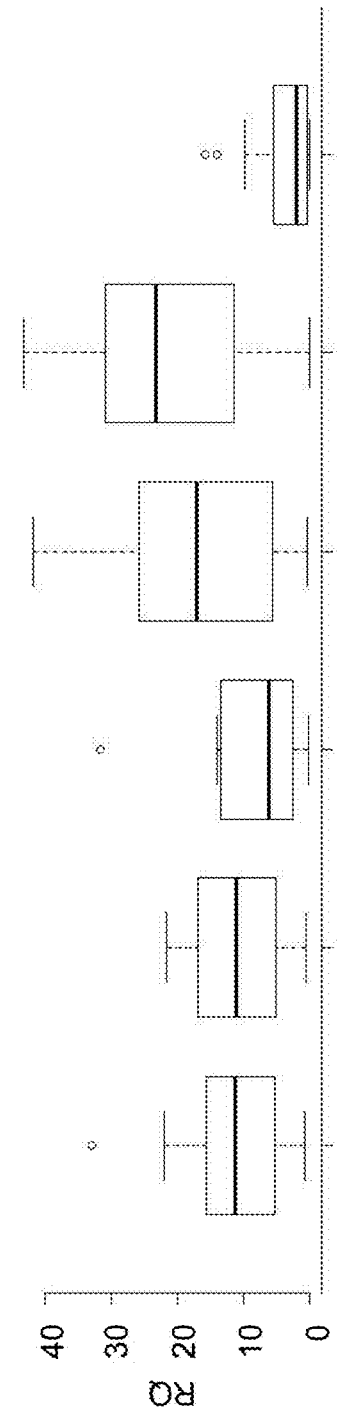
FIG. 9A and FIG. 9B show the RNA expression level by QRT-PCR of Axmi028 and Axmi100 optimized genes in maize transformants.
Figure 9B:
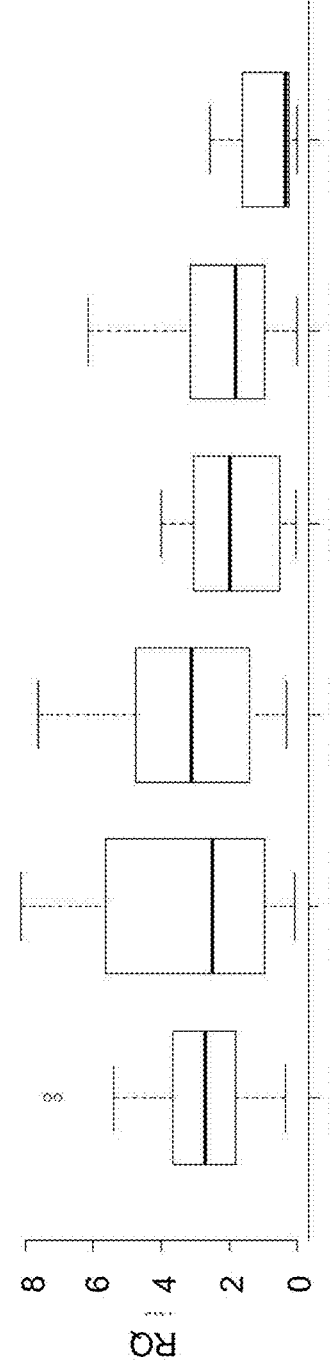

Western blot analysis on maize leaf protein extracts from plants transformed with Axmi100+GUS constructs (FIG. 7B) were performed with an Axmi100 polyclonal antibody. No Axmi100 protein could be detected in plants transformed with the 100-WT gene. Axmi100 protein expression could be observed in plants transformed with the 100-opt, 100-opt+3pA and 100-opt+pA sequences. Expression seemed least robust in 100-opt+pA transformants where only 5 out of 10 transformed plants expressed significant levels of Axmi100 protein. RT-QPCR analyses using 3' and 5' primer pairs (SEQ ID 25-28) also showed that transcript levels of 100-opt+pA in maize transformants were lower than those obtained in 100-opt and 100-opt+3pA transformants (FIGS. 9A and 9B).

It can be concluded from these results that gene optimization is necessary to obtain Axmi028 and Axmi100 protein expression. The addition of weak polyadenylation motifs does not impair protein expression. The presence of 3 or a few more weak polyadenylation motifs in the optimized sequences does not impair protein expression or can improve expression compared to the optimized gene sequence. However the re-introduction of all the polyA motifs into the optimized sequence can reduce the chance of obtaining a protein expression level equivalent to that obtained from the optimized gene.

REFERENCES

Campbell and Gowri (1990). Codon usage in higher plants, green algae and cyanobacteries. Plant Physiol. 92:1-11.

Colgan D F, Manley J L. (1997). Mechanism and regulation of mRNA polyadenylation. Genes Dev. 11(21):2755-66.

Guilley H, Dudley R K, Jonard G, Balazs E, Richards K E: Transcription of Cauliflower mosaic virus DNA: detection of promoter sequences, and characterization of transcripts. Cell. 1982, 30: 763-773.

Lu A, Diehn S and Cigan M (2015). Maize Protein Expression. In Recent Advancements in Gene Expression and Enabling Technologies in Crop Plants. Editors; Kasi Azhakanandam, Aron Silverstone, Henry Daniell and Michael R. Davey. Springer ISBN 978-1-4939-2201-7; ISBN 978-1-4939-2202-4 (eBook); DOI 10.1007/978-1-4939-2202-4.

Graber J H, Cantor C R, Mohr S C, Smith T F. (1999) In silico detection of control signals: mRNA 3'-end-processing sequences in diverse species. Proc Natl Acad Sci USA. 96:14055-60.

Ishida Y, Saito H, Ohta S, Hiei Y, Komari T, Kumashiro T. (1996) High efficiency transformation of maize (*Zea mays* L.) mediated by *Agrobacterium tumefaciens*. Nature Biotechnol. 14, 745-50.

Jefferson R A, Kavanagh, T A and Bevan, M W (1987). GUS fusions: beta-glucuronidase as a sensitive and versatile gene fusion marker in higher plants. EMBO J. 6: 3901-3907.

Ji G, Li L, Li Q Q, Wu X, Fu J, Chen G, Wu X. (2015) PASPA: a web server for mRNA poly(A) site predictions in plants and algae. Bioinformatics 31:1671-3.

Joshi C P. (1987) Putative polyadenylation signals in nuclear genes of higher plants: a compilation and analysis. Nucleic Acids Res. 15(23):9627-40.

Komari T, Hiei Y, Saito Y, Murai N, Kumashiro T. (1996). Vectors carrying two separate T-DNAs for co-transformation of higher plants mediated by *Agrobacterium tumefaciens* and segregation of transformants free from selection markers. Plant J. 10:165-74.

Leckie B M, Neal Stewart C Jr. (2011). Agroinfiltration as a technique for rapid assays for evaluating candidate insect resistance transgenes in plants. Plant Cell Rep. 30(3):325-34.

Mogen B D, MacDonald M H, Graybosch R, Hunt A G. (1990) Upstream sequences other than AAUAAA are required for efficient messenger RNA 3'-end formation in plants. Plant Cell. 2(12):1261-72.

Murray E E et al. (1989) Codon usage in plant genes. Nucleic Acids Res. 17:477-498

Sanfacon H, Brodmann P, Hohn T. (1991) A dissection of the cauliflower mosaic virus polyadenylation signal. Genes Dev. 5(1):141-9.

Sheen, J. 2002, A transient expression assay using *Arabidopsis mesophyll* protoplasts. http://genetics.mgh.harvard.edu/sheenweb/

Tzanis G et al (2011). PolyA-iEP: A data mining method for the effective prediction of polyadenylation sites. Expert Syst. Appl. 38(10) 12398-12408.

Verdaguer B, de Kochko A, Beachy R N, Fauquet C. (1996). Isolation and expression in transgenic tobacco and rice plants, of the cassava vein mosaic virus (CVMV) promoter. Plant Mol Biol. 31:1129-39

Wu X et al (2012). Comprehensive recognition of messenger RNA polyadenylation pattern in plants. African journal of biotechnology, vol 11(14), pp 3215-3234.

The invention claimed is:

1. A method of making an expression cassette comprising a nucleic acid molecule having a coding sequence encoding a non-plant protein for transforming a plant, comprising the steps of:
   a) identifying a coding sequence that encodes a non-plant protein;
   b) identifying each polyadenylation motif sequence from among AAAATA, AACCAA, AAGCAT, AATAAA, AATAAT, AATACA, AATCAA, AATTAA, ATAAAA, ATACAT, ATACTA, ATATAA, ATGAAA, ATTAAA, ATTAAT and CATAAA, and its nucleic acid position in said coding sequence;
   c) optimizing said coding sequence by codon substitution, including by recoding the nucleic acid molecule such that the codon usage reflects that used in the plant, wherein the optimized coding sequence encodes for said non-plant protein, wherein said optimization step provides an optimized coding sequence in which one or more polyadenylation motif sequences have been removed, and wherein said optimization step does not result in adding to said coding sequence any polyadenylation motif from among the AATTAA, ATACTA, ATATAA, ATTAAA, ATTAAT and CATAAA motifs;
   d) modifying said optimized coding sequence to obtain a modified gene sequence by introducing in the optimized gene sequence at least one polyadenylation motif sequence selected from among AAAATA, AACCAA, AAGCAT, AATAAA, AATAAT, AATACA, AATCAA, ATAAAA, ATACAT and ATGAAA, so as to obtain a modified coding sequence that comprises at least three but not all polyadenylation motifs identified in step b), wherein said modifying step does not result in adding to said coding sequence any polyadenylation motif from among the AATTAA, ATACTA, ATATAA, ATTAAA, ATTAAT and CATAAA motifs, resulting in said modified coding sequence comprising more polyadenylation motifs than the optimized sequence, and said modified coding sequence is encoding said non-plant protein;
   e) synthesizing a nucleic acid molecule having the modified coding sequence as obtained in step d; and
   f) operably linking a promoter and a terminator to said nucleic acid molecule to obtain an expression cassette for expression in plant.

2. The method of claim 1 wherein each polyadenylation motif introduced within said optimized sequence in step d) is a wild-type polyadenylation motif identified in step b), and is introduced at a nucleic acid position corresponding to its position within the coding sequence as identified in step b).

3. The method of claim 1 wherein the polyadenylation motif sequence introduced in step d) is chosen amongst motifs ATGAAA, AAGCAT, AACCAA, AATCAA or AAAATA.

4. The method of claim 2 wherein the polyadenylation motif sequence introduced in step d) is chosen amongst motifs ATGAAA, AAGCAT, AACCAA, AATCAA or AAAATA.

5. The method of claim 1 wherein the modified coding sequence comprises three to ten polyadenylation motifs.

6. The method of claim 2 wherein the modified coding sequence comprises three to ten polyadenylation motifs.

7. The method of claim 1, wherein said coding sequence is encoding a prokaryotic protein.

8. The method of claim 1, wherein said coding sequence is encoding an insecticidal *Bacillus thuringiensis* protein.

9. The method of claim 1, further comprising the steps of transforming a plant cell with the expression cassette and regenerating a plant from the transformed plant cell.

10. The method of claim 2, further comprising the steps of transforming a plant cell with the expression cassette and regenerating a plant from the transformed plant cell.

* * * * *